(12) United States Patent
Southwell et al.

(10) Patent No.: US 10,279,174 B2
(45) Date of Patent: *May 7, 2019

(54) STIMULATION DEVICE AND METHOD FOR TRANSCUTANEOUS ELECTRICAL STIMULATION

(71) Applicant: GI THERAPIES PTY LTD, Melbourne, Victoria (AU)

(72) Inventors: Bridget Rae Southwell, Gordon (AU); Rod Wiebenga, Kew East (AU); David Fisher, Pymble (AU)

(73) Assignee: GI Therapies Pty Ltd, Melbourne, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,822

(22) Filed: Nov. 20, 2017

(65) Prior Publication Data

US 2018/0133468 A1    May 17, 2018

Related U.S. Application Data

(63) Continuation of application No. 15/027,953, filed as application No. PCT/AU2014/000969 on Oct. 10, 2014, now Pat. No. 9,827,418.

(30) Foreign Application Priority Data

Oct. 11, 2013  (AU) ................................ 2013903922
Oct. 11, 2013  (AU) ................................ 2013903926

(51) Int. Cl.
*A61N 1/32*     (2006.01)
*A61N 1/22*     (2006.01)
(Continued)

(52) U.S. Cl.
CPC ............. *A61N 1/321* (2013.01); *A61N 1/048* (2013.01); *A61N 1/0452* (2013.01);
(Continued)

(58) Field of Classification Search
USPC ......................................... 607/41
See application file for complete search history.

(56) References Cited

U.S. PATENT DOCUMENTS 4,381,012 A    4/1983   Russek
4,690,144 A    9/1987   Rise et al.
(Continued)

FOREIGN PATENT DOCUMENTS

GB         960682       6/1964
JP         02-206475    8/1990
(Continued)

OTHER PUBLICATIONS

Chase et al., 2005, Pilot Study Using Transcutaneous Electrical Stimulation (Interferential Current) to Treat Chronic Treatment-Resistant Constipation and Soiling in Children, Journal of Gastroenterology and Hepatology, 20:1054-1061.
(Continued)

*Primary Examiner* — Nicole F Lavert
(74) *Attorney, Agent, or Firm* — Knobbe Martens Olson & Bear LLP

(57) ABSTRACT

A device for transcutaneous electrical stimulation is provided. The device comprises circuitry configured to generate transcutaneous stimulation signals. The device also comprises a first signal output component for electrically connecting to a first electrode connector to deliver generated transcutaneous stimulation signals. The first signal output component comprises a first four-pole electrical connector part. The device further comprises a second signal output component for electrically connecting to a second electrode
(Continued)

connector to deliver generated transcutaneous stimulation signals. The second signal output component comprises a second four-pole electrical connector part. The device further comprises a controller to selectively control output of the stimulation signals to selected pairs of poles across the first and second four-pole electrical connector parts. Each selected pair of poles comprises one pole from the first four-pole electrical connector part and one pole from the second four-pole electrical connector part.

20 Claims, 34 Drawing Sheets

(51) Int. Cl.
    *A61N 1/04* (2006.01)
    *A61N 1/36* (2006.01)

(52) U.S. Cl.
    CPC ......... *A61N 1/0456* (2013.01); *A61N 1/0484* (2013.01); *A61N 1/22* (2013.01); *A61N 1/323* (2013.01); *A61N 1/36007* (2013.01); *A61N 1/36014* (2013.01)

(56) References Cited

U.S. PATENT DOCUMENTS

| | | | |
|---|---|---|---|
| 5,562,717 | A | 10/1996 | Tippey et al. |
| 5,871,534 | A | 2/1999 | Messick et al. |
| 6,445,955 | B1 | 9/2002 | Michelson et al. |
| 6,728,577 | B2 | 4/2004 | Minogue et al. |
| 8,000,792 | B1 | 8/2011 | Dechev et al. |
| 8,019,426 | B2 | 9/2011 | Moore et al. |
| 9,789,308 | B2 | 10/2017 | Southwell et al. |
| 9,827,418 | B2 | 11/2017 | Southwell et al. |
| 9,861,816 | B2 | 1/2018 | Southwell et al. |
| 2004/0030267 | A1 | 2/2004 | Orten |
| 2005/0055054 | A1 | 3/2005 | Yu |
| 2005/0075678 | A1 | 4/2005 | Faul |
| 2005/0278001 | A1 | 12/2005 | Qin et al. |
| 2006/0009815 | A1 | 1/2006 | Boveja |
| 2006/0089683 | A1 | 4/2006 | Hagglof et al. |
| 2006/0184211 | A1 | 8/2006 | Gaunt et al. |
| 2006/0195153 | A1 | 8/2006 | Diubaldi et al. |
| 2007/0055337 | A1 | 3/2007 | Tanrisever |
| 2007/0150034 | A1 | 6/2007 | Rooney |
| 2007/0156183 | A1 | 7/2007 | Rhodes |
| 2007/0255085 | A1 | 11/2007 | Kishawi et al. |
| 2008/0077192 | A1 | 3/2008 | Harry |
| 2008/0147143 | A1 | 6/2008 | Popovic et al. |
| 2008/0208287 | A1* | 8/2008 | Palermo ............... A61N 1/0452 607/48 |
| 2008/0249591 | A1 | 10/2008 | Gaw et al. |
| 2009/0048642 | A1 | 2/2009 | Goroszeniuk |
| 2009/0157149 | A1 | 6/2009 | Wahlgren et al. |
| 2009/0182393 | A1* | 7/2009 | Bachinski ............ A61N 1/0428 607/59 |
| 2010/0049027 | A1 | 2/2010 | Teschner et al. |
| 2010/0152817 | A1 | 6/2010 | Gillbe |
| 2011/0230701 | A1* | 9/2011 | Simon ................. A61N 1/36021 600/9 |
| 2011/0295339 | A1 | 12/2011 | Carroll |
| 2012/0029591 | A1* | 2/2012 | Simon ...................... A61N 1/40 607/42 |
| 2012/0116477 | A1 | 5/2012 | Crowe et al. |
| 2013/0123568 | A1* | 5/2013 | Hamilton ........... A61N 1/36003 600/13 |
| 2016/0250463 | A1 | 9/2016 | Southwell et al. |
| 2017/0182318 | A1 | 6/2017 | Fisher et al. |
| 2017/0348526 | A1 | 12/2017 | Southwell et al. |

FOREIGN PATENT DOCUMENTS

| | | |
|---|---|---|
| JP | 08-501946 | 3/1996 |
| JP | 10-179768 | 7/1998 |
| JP | 2001-170190 | 6/2001 |
| JP | 2001-238967 | 9/2001 |
| JP | 2007-037853 | 2/2007 |
| JP | 2008-307382 | 12/2008 |
| JP | 2009-136585 | 6/2009 |
| WO | WO 08/137162 | 11/2008 |
| WO | WO 11/026166 | 3/2011 |
| WO | WO 12/116407 | 9/2012 |
| WO | WO 15/051405 | 4/2015 |
| WO | WO 15/051406 | 4/2015 |

OTHER PUBLICATIONS

Clarke et al., 2009, Decreased colonic transit time after transcutaneous interferential electrical stimulation in children with slow transit constipation, Journal of Pediatric Surgery, 44(2):408-412.

Clarke et al., 2009, Improvement of quality of life in children with slow transit constipation after treatment with transcutaneous electrical stimulation. J Pediatr Surg, 44: 1268-1273.

Clarke et al., 2012, Transabdominal electrical stimulation increases colonic propagating pressure waves in paediatric slow transit constipation. J Pediatr Surg. 47(12):2279-2284.

De Paepe et al., 2002, The role of pelvic-floor therapy in the treatment of lower urinary tract dysfunctions in children, Scand J Urol Nephrol. 36(4):260-267 (abstract).

Ismail et al., 2009, Daily transabdominal electrical stimulation at home increased defecation in children with slow-transit, J Pediatr Surg, 44: 2388-2392.

Kajbafzadeh et al., 2012, Transcutaneous interferential electrical stimulation for management of neurogenic bowel dysfunction in children with myelomeningocele. Int J Colorectal Dis, 27:453-458.

Koklu et al., May 2010, Clinical trial: interferential electric stimulation in functional dyspepsia patents—a prospective randomized study, Aliment Pharmacol Ther, 31:961-968.

Leong et al., 2001, Long-term effects of transabdominal electrical stimulation in treating children with slow-transit constipation, Journal of Pediatric Surgery, 46:2309-2312.

Queralto et al., Interferential Therapy: a new treatment for slow transit constipation. A pilot study in adults. Colorectal Dis 2012: 15: e35-e39.

Sikiru et al., Nov.-Dec. 2008, Transcutaneous electrical nerve stimulation (TENS) in the symptomatic management of chronic prostatitis/chronic pelvic pain syndrome: a placebo-control randomized trial, International Braz J Urol., 34(6):708-713.

Southwell, 2013, Medical devices to deliver transcutaneous electrical stimulation using interferential current to treat constipation, Expert Rev. Med. Devices, 19(6):701-704.

Southwell, B. Treatment of slow transit constipation in children. Fifth European Paediatric Motility Meeting, J Pediatr Gastroenterol Nutr 2011; 53: Suppl 2 s 551-3.

Stillman et al., 2006, Strengthening of the pelvic floor muscles using transcutaneous magnetic nerve stimulation: a review of the literature. Australian and New Zeland Continence Journal. 12(2):31-40.

Veiga ML, Lordêlo P, Farias T, Barroso U Jr. Evaluation of constipation after parasacral transcutaneous electrical nerve stimulation in children with lower urinary tract dysfunction—a pilot study. J Pediatr Urol. 2013; 9(5):622-6.

Vitton et al., 2009, Transcutaneous Posterior Tibial Nerve Stimulation for Fecal Incontinence in Inflammatory Bowel Disease Patients: A Therapeutic Option?, Inflammatory Bowel Diseases, 15(3):402-405.

Yik et al., 2011, Slow-transit constipation with concurrent upper gastrointestinal dysmotility and its response to transcutaneous electrical stimulation. J Pediatr Surg Int, 27(7):705-711.

Yik et al., 2012, Home transcutaneous electrical stimulation to treat children with slow-transit constipation, Journal of Pediatric Surgery, 47:1285-1290.

(56) References Cited

OTHER PUBLICATIONS

Yik et al., 2012, The impact of transcutaneous electrical stimulation therapy on appendicostomy operation rates for children with chronic constipation—a single—institution experience, Journal of Pediatr Surg, 47: 1421-1426.

Yik et al., 2013, Home Transcutaneous Electrical Stimulation (TES) Therapy to Treat Children with Anorectal Retention (AR): A Pilot Study. Gastroenterology, 144(5):S364.

Yik et al., 2013, Treatment Resistant Slow-Transit Constipation (STC) in Children Can Be Improved With Home-Based Transcutaneous Electrical Stimulation. Gastroenterology, 144(5):S399.

Chase et al., Abstract for oral presentation on "Daily transcutaneous electrical stimulation (using interferential current) at home increased defecation in children with slow transit constipation: a pilot study," Neurogastroenterology and Motility 2009, Joint International Meeting, Chicago Aug. 27-30, Abstract published on Jul. 1, 2009, p. 3.

Ismail et al., Daily transcutaneous electrical stimulation at home increased defecation in children with slow transit constipation: a pilot study, 42nd Annual Meeting of Pacific Association of Pediatric Surgeons, May 10-14, 2009, Hong Kong, abstract, pp. 216-217.

Ismail et al., J Pediatr Surg website screen capture showing article preview with publication date of Dec. 2009 for article Daily transabdominal electrical stimulation at home increased defecation in children with slow-transit, J Pediatr Surg, 44: 2388-2392 (retrieved on Jul. 28, 2017, from: http://www.jpedsurg.org/article/S0022-3468(09)00640-X/pdf).

Ismail et al., PubMed website screen capture showing article preview with publication date of Dec. 2009 for article "Daily transabdominal electrical stimulation at home increased defecation in children with slow-transit," J Pediatr Surg, 44: 2388-2392 (retrieved on Jul. 28, 2017, from: http://www.sciencedirect.com/science/article/pii/S002234680900640X).

Ismail et al., ScienceDirect website screen capture showing article preview with publication date of Dec. 2009 for article "Daily transabdominal electrical stimulation at home increased defecation in children with slow-transit," J Pediatr Surg, 44: 2388-2392 (retrieved on Jul. 28, 2017, from: http://www.sciencedirect.com/science/article/pii/S002234680900640X).

* cited by examiner

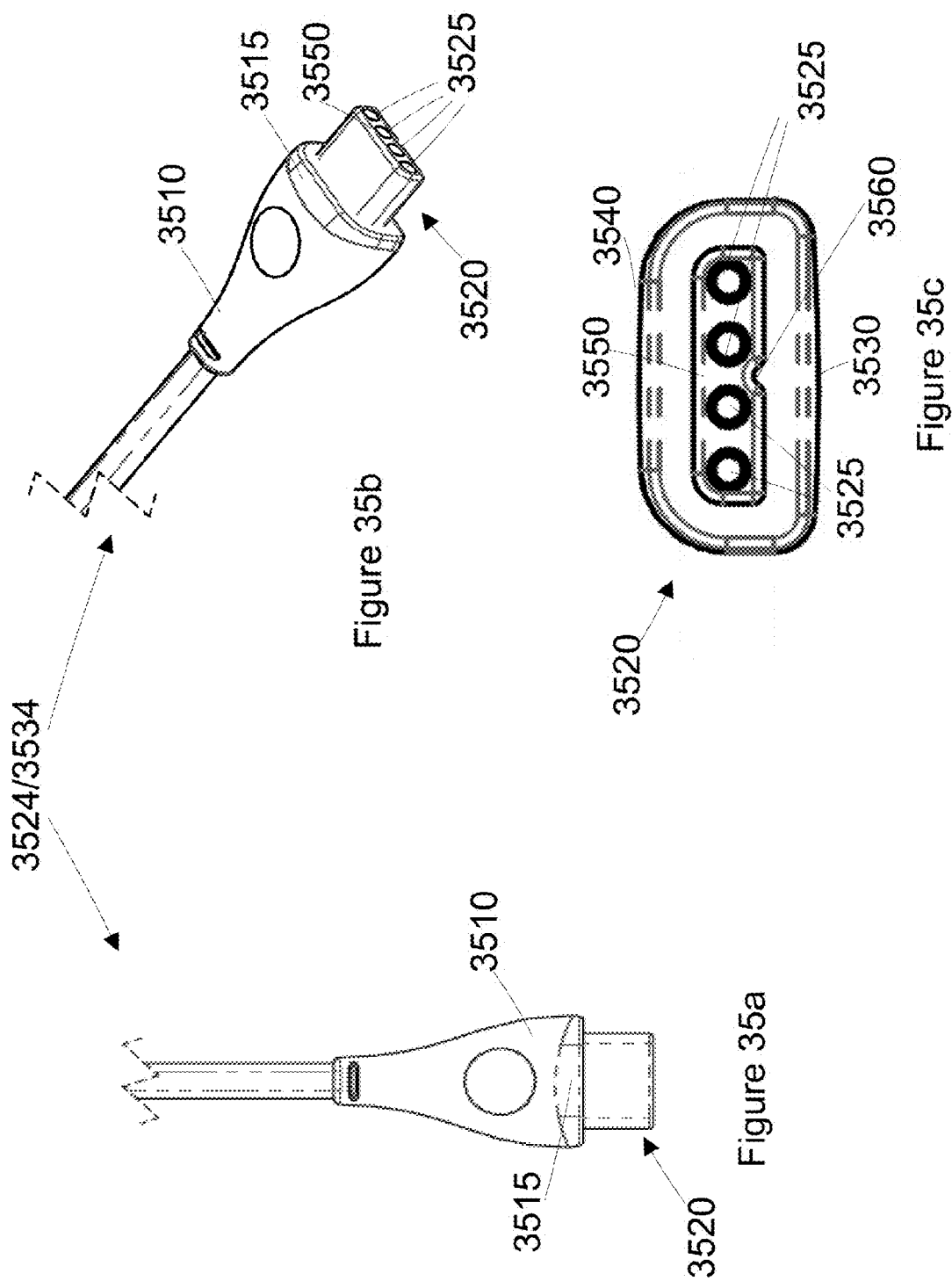

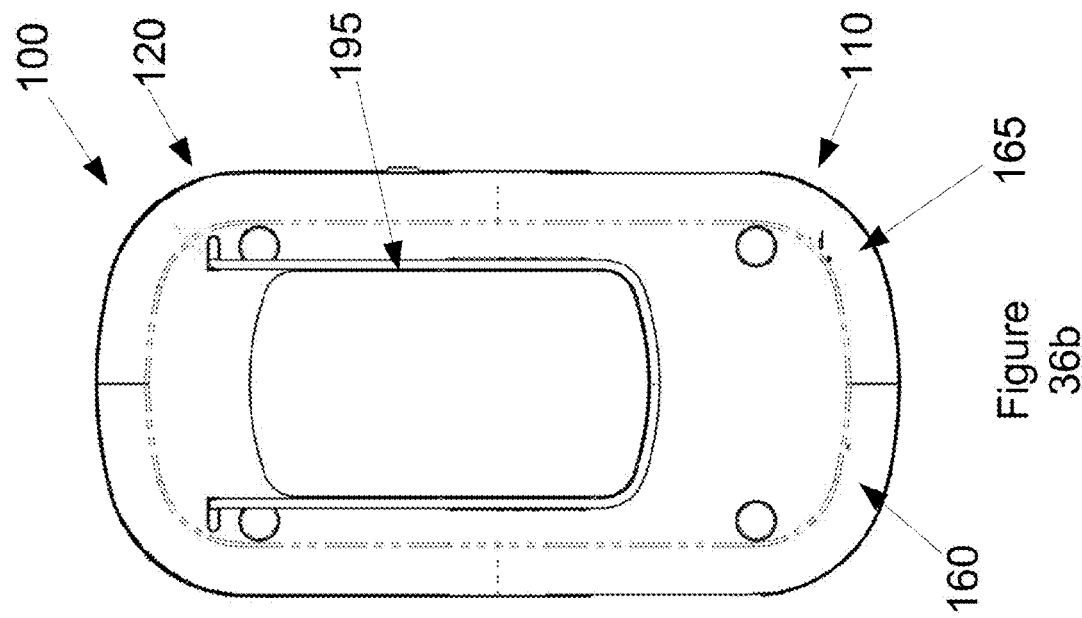
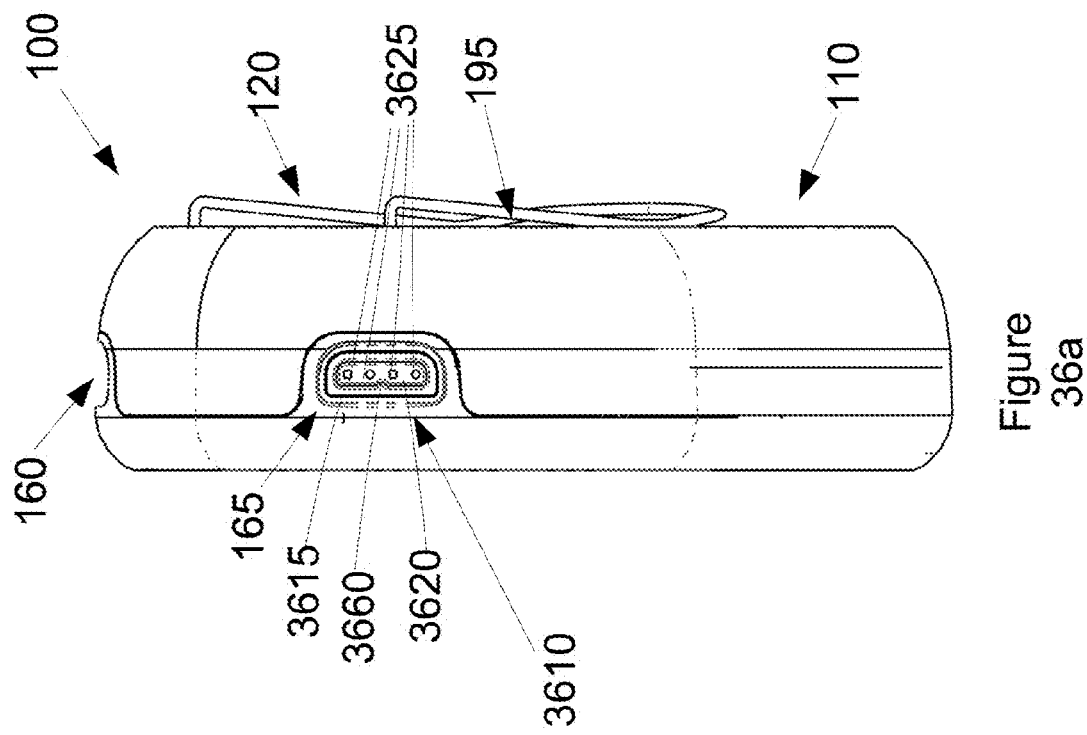

STIMULATION DEVICE AND METHOD FOR TRANSCUTANEOUS ELECTRICAL STIMULATION

CROSS-REFERENCE TO RELATED APPLICATIONS

This application is a continuation of U.S. patent application Ser. No. 15/027,953, filed Apr. 7, 2016, now U.S. Pat. No. 9,827,418, which is a U.S. national phase of PCT/AU2014/000969, filed Oct. 10, 2014, which claims priority to AU App. No. 2013903922, filed Oct. 11, 2013, and to AU App. No. 2013903926, filed Oct. 11, 2013, each of which is hereby incorporated by reference in its entirety for all purposes. Any and all applications for which a foreign or domestic priority claim is identified in the Application Data Sheet as filed with the present application, or any correction thereto, are hereby incorporated by reference under 37 CFR 1.57.

TECHNICAL FIELD

Described embodiments generally relate to methods and systems for transcutaneous stimulation. In particular, described embodiments are directed to methods, devices and systems for transcutaneous stimulation in the lumbar and/or abdominal region to treat one or more dysfunctions associated with a body's ability to evacuate waste.

BACKGROUND

Waste elimination dysfunction of the gastrointestinal tract can take many forms. For example, intestinal incontinence or constipation can occur. Treatment systems exist for treating constipation by providing electrical stimulus via subcutaneously implanted electrodes positioned around the lower bowel. Electrical stimulation provided using such electrodes can be used to sequentially activate muscle fibres around the bowel to force a peristaltic action to occur. However, such treatment systems are undesirably invasive. Further, while such systems may have an immediate effect in assisting to evacuate the bowel, they do not necessarily address the cause of the constipation. Importantly, this effect has not been described as long lasting, or having an effect beyond the immediate time of electrical stimulation.

Intractable constipation and soiling are extremely common in the community, in both the young and the old, and available treatments are generally uncomfortable, can cause social distress for sufferers and are a significant drain on the health care system. Individuals that suffer from constipation and soiling who are young or old may also have psychological issues. In addition, constipation may be a side effect of some kinds of medication, such as opiates. Most laxative therapies are designed to either soften the stool or stimulate the bowel by chemicals in the lumen. Patients with chronic constipation or intractable constipation may have failed other treatment methods including pharmaceutical treatment. Patients on therapies for other diseases in which constipation is a side effect of the medication may not be able to be co-administered pharmaceutical treatments for constipation. Non-invasive, non-drug-based treatment methodologies may be desired in some cases.

Sometimes constipation may be unrelated to diet or medications, and can be due to poor motility in the whole colon. A newly identified disorder, which is known as slow-transit constipation (STC), is not uncommon amongst children who fail standard medical therapy, and such children often have signs of colonic dysfunction even at birth.

Some devices exist for delivering transcutaneous stimulation and/or treating faecal waste evacuation dysfunction. However, various drawbacks exist with such devices.

It is desired to address or ameliorate one or more shortcomings or disadvantages or shortcomings associated with existing faecal waste evacuation treatment devices, systems, methods or regimes, or to at least provide a useful alternative thereto.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

Some embodiments relate to a device for transcutaneous electrical stimulation, comprising:
  circuitry configured to generate transcutaneous stimulation signals;
  a first signal output component for electrically connecting to a first electrode connector to deliver generated transcutaneous stimulation signals, the first signal output component comprising a first four-pole electrical connector part;
  a second signal output component for electrically connecting to a second electrode connector to deliver generated transcutaneous stimulation signals, the second signal output component comprising a second four-pole electrical connector part; and
  a controller to selectively control output of the stimulation signals to selected pairs of poles across the first and second four-pole electrical connector parts, wherein each selected pair of poles comprises one pole from the first four-pole electrical connector part and one pole from the second four-pole electrical connector part.

Some embodiments relate to a device for transcutaneous electrical stimulation, comprising:
  circuitry configured to generate transcutaneous interferential current stimulation signals;
  at least one first signal output component for electrically connecting to a first bank of stimulation electrodes; and
  at least one second signal output component for electrically connecting to a second bank of stimulation electrodes; and
  wherein the device is configured to deliver generated transcutaneous interferential stimulation signals to the first bank for a first set period of time, and subsequently to the second bank for a second set period of time when the first and second signal output components are electrically connected to the respective first and second banks of the stimulation electrodes.

The transcutaneous stimulation signals may comprise interferential current stimulation signals for application to a front body region including the lower abdomen and pelvic area and a back body region including the lumbar and sacral area. The first and second signal coupling components may each define respective sockets for receiving a mating jack of respective electrode connectors and for transmitting stimulation signals across a set of channels. In some embodiments, there may be at least two channels. In some other embodiments, there may be at least four channels.

The device may be substantially free of external user operatable controls other than a means of turning the device on an off, a means to control the intensity of the transcutaneous stimulation signals, and a means to turn on and off a sound generating component.

The device may comprise communication circuitry configured to allow communication with an external computing device. The device may be configured to allow configuration of electrical stimulation parameters of the device by the external computing device via the communication circuitry. The electrical stimulation parameters may include: a maximum current intensity setting to be applied in the transcutaneous electrical stimulation; aduration of transcutaneous electrical stimulation; and a sequence of electrode pairs to which the transcutaneous electrical stimulation is to be applied.

The device may further comprise isolation circuitry to electrically isolate a power supply unit of the device from the signal output components. The device may further comprise a microcontroller, a memory unit and at least one user interface component.

The device may be configured to deliver the transcutaneous electrical stimulation according to at least one stored configuration parameter stored in the memory unit. The device may be configured so that, when commencing the transcutaneous electrical stimulation, the current of the stimulation is initially zero and is automatically increased over time until it reaches a pre-set stimulation level or is stopped by user input and can then be modified by user input.

The device may be configured to monitor an impedance between pairs of output terminals of the first and second signal output components, and to produce a pad fault signal when the impedance is above a predetermined threshold level.

The device may further comprise means to generate at least one of visual, aural, and tactile notifications.

Some embodiments relate to a method performed in a device configured to generate transcutaneous interferential current stimulation for delivery to a first set of at least four electrodes on a front of a torso and a second set of at least four electrodes on a back of the torso, the method comprising:
  selecting two pairs of electrodes, wherein each selected pair of electrodes comprises one electrode from the first set of electrodes and one electrode from the second set of electrodes;
  delivering transcutaneous stimulation signals to the selected electrodes from the first set of electrodes; and
  at the same time as delivering transcutaneous stimulation signals to the selected electrodes from the first set of electrodes, delivering transcutaneous interferential current stimulation signals to the selected electrodes from the second set of electrodes.

Some embodiments relate to a stimulation device for transcutaneous electrical stimulation, comprising:
  a housing having a first end and an opposite second end;
  circuitry configured to generate transcutaneous stimulation signals; and
  first and second signal coupling components for connection to respective electrode connectors to deliver the transcutaneous stimulation signals;
  wherein each of the first and second signal coupling components is located at the first end of the housing, wherein the first signal coupling component has a first coupling axis and the second signal coupling component has a second coupling axis, and wherein the first and second coupling axes are disposed at an angle relative to each other.

The angle may be between about 120° and about 60°. The angle may be between about 100° and about 80°. The angle may be about 90°.

The housing first end may comprise first and second opposed corner portions and first and second coupling axes extend through the first and second corner portions. The first and second corner portions may define respective recesses for receiving at least a part of respective electrode connectors.

Some embodiments relate to a stimulation device for transcutaneous electrical stimulation, comprising:
  a housing having a first end and a second end;
  a screen display;
  circuitry configured to generate transcutaneous stimulation signals;
  first and second signal coupling components for connection to respective electrode connectors to deliver the transcutaneous stimulation signals, the coupling components being at the first end; and
  a coupling portion, to couple the device to a wearer, the coupling portion being connected to the housing at the first end;
  wherein the coupling portion allows the device to hang in an inverted position in which the display is upside-down so that when the second end of the device is pivoted upwardly away from the wearer, the display is right-side-up from the wearer's perspective.

The first signal coupling component may have a first coupling axis and the second signal coupling component may have a second coupling axis, and first and second coupling axes may be disposed at an angle relative to each other.

The angle may be between about 120° and about 60°. The device may further comprise user controls at the second end. The coupling portion may comprise a clip.

The coupling portion may cooperate with a receiving portion of an electrode carrier to allow the device to be pivoted so that the second end can be swung from below the first end upwards and away from the body of the wearer.

BRIEF DESCRIPTION OF DRAWINGS

Embodiments are described in further detail below, by way of example and with reference to the accompanying drawings, in which:

FIGS. 35a, 33b and 35c show top, perspective and end views of an alternative connector that may plug into some embodiments of the device of FIG. 1;

FIG. 36a shows a perspective side view of the device of FIG. 1; and

FIG. 36b shows a back view of the device of FIG. 1.

DETAILED DESCRIPTION

Described embodiments generally relate to methods and systems for transcutaneous stimulation. In particular, described embodiments are directed to methods, devices and systems for transcutaneous stimulation in the lumbar and/or abdominal region to treat one or more dysfunctions associated with a body's ability to evacuate waste, in particular waste associated with disorders of the gastrointestinal tract.

Described embodiments generally relate to improvements and further developments to embodiments described in earlier International Patent Application PCT/AU2012/000212, published as International Patent Publication No. WO 2012/116407, the entire contents of which are herein incorporated by reference. International Patent Publication No. WO 2012/116407 discusses various methods and regimes for treating a waste evacuation dysfunction by administering transcutaneous electrical stimulation (TES) to a patient. In some embodiments, the stimulation generation device 100 described herein is configured to generate and transmit transcutaneous electrical stimulation in accordance with the teachings of WO 2012/116407 to treat a waste evacuation dysfunction. For example, the stimulation generation device 100 may be configured to provide a stimulation current across a 1KΩ load with a peak-to-peak magnitude of less than about 40 mA and greater than zero mA. The current may be provided at a carrier frequency of between about 1 kHz and about 10 kHz, with a modulated frequency of about 20 Hz to about 300 Hz. Alternatively, the carrier frequency may be about 4 kHz and the modulated frequency may be about 80 Hz to 150 Hz, or 80 Hz to 160 Hz in some embodiments. Furthermore, the electrical stimulation may comprise interferential electrical current stimulation.

In some embodiments, the stimulation generation device 100 may be configured to provide transcutaneous electrical stimulation to first and second electrode connector assemblies 220, 230 for at least one treatment period per day over a treatment term of at least one week, and/or for two or three treatment periods per day. In some embodiments the treatment period may be between about 10 minutes and about 90 minutes, or between about 20 minutes and about 60 minutes.

Figure 1:
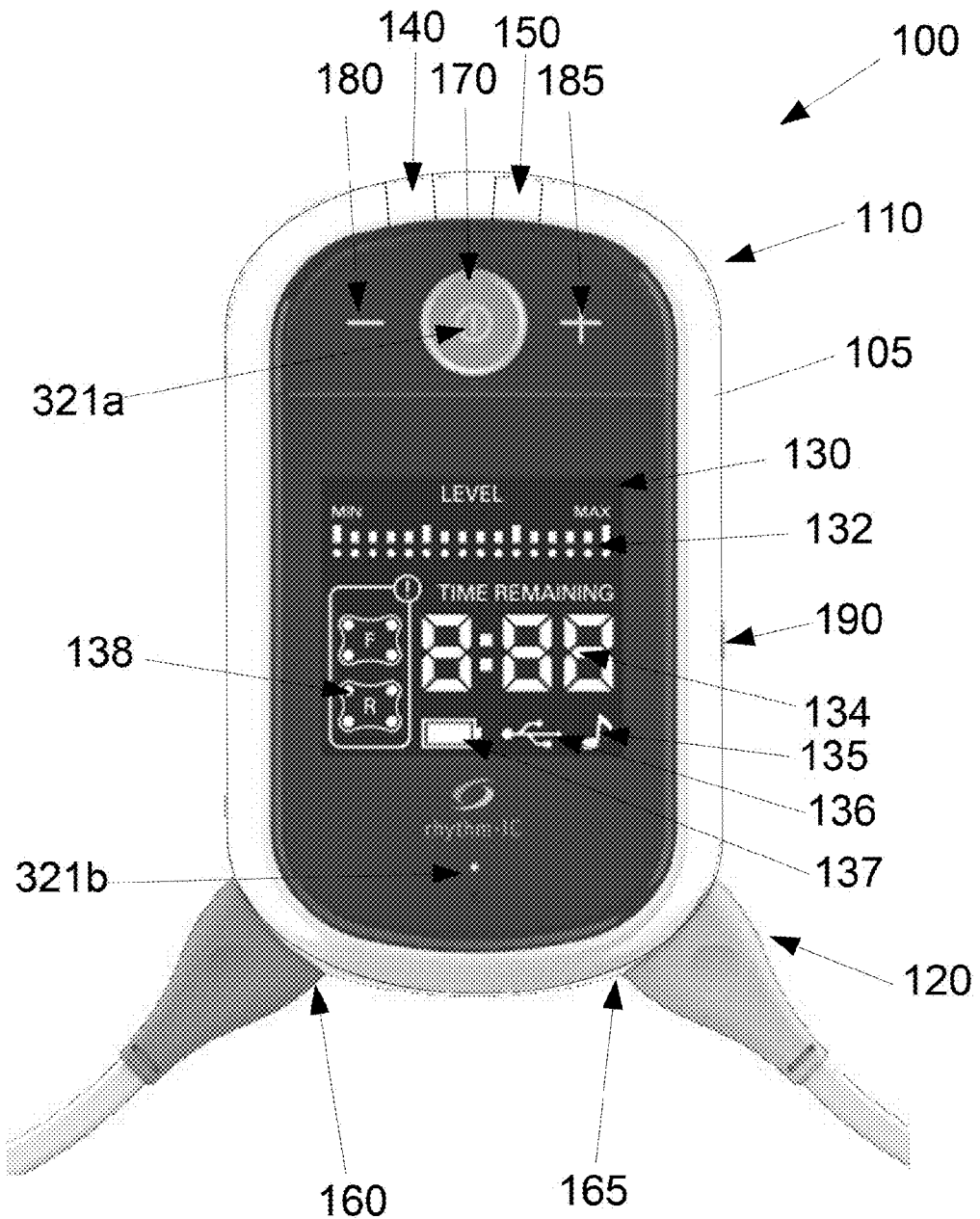
FIG. 1 shows a front view of a stimulation device according to some embodiments.

FIG. 1 shows a stimulation device 100 according to some embodiments. Described embodiments of device 100 are generally directed towards the use of the device to drive stimulation signals onto electrode connectors for electrical communication of the signals to electrode pads that are to be worn on the body of a patient, for the treatment of one or more dysfunctions associated with a body's ability to evacuate waste, in particular disorders associated with waste evacuation of the gastrointestinal tract.

In some embodiments, the device 100 is used in a method of treatment of faecal evacuation disorders, such as and not limited to: constipation, slow transit constipation, functional faecal retention, rectal faecalomas, anal retention or irritable bowel syndrome with constipation, for example.

Stimulation device 100 comprises a housing 105 with a top end 110, a bottom end 120, and a display portion, which may be a screen such as LCD segment display screen 130 or a touch screen. In some embodiments, screen 130 may be a standard LCD screen, such as a 4.8" colour LCD screen, for example. Top end 110 and bottom end 120 extend along, and are positioned at opposite ends of, a long axis of the housing

105. The housing 105 houses internal components of the device 100, such as its electronics and other components, as described further below. Stimulation device 100 may further include other outputs, such as a speaker or piezoelectric buzzer to produce sound, or a motor to provide tactile vibration to the user. Stimulation device 100 may also have inputs such as accelerometers, GPS modules, microphones or cameras. Stimulation device 100 may be a handheld device generally of a size and shape easily held in one hand of the user. The device 100 may further be lightweight and robust, with the exterior being of a smooth construction with few sharp edges or projections. The device 100 may generally be designed for easy portability and handling.

Screen 130 is configured to be human-readable when stimulation device 100 is oriented such that top end 110 is (from the viewer's perspective) above bottom end 120.

Figure 2:
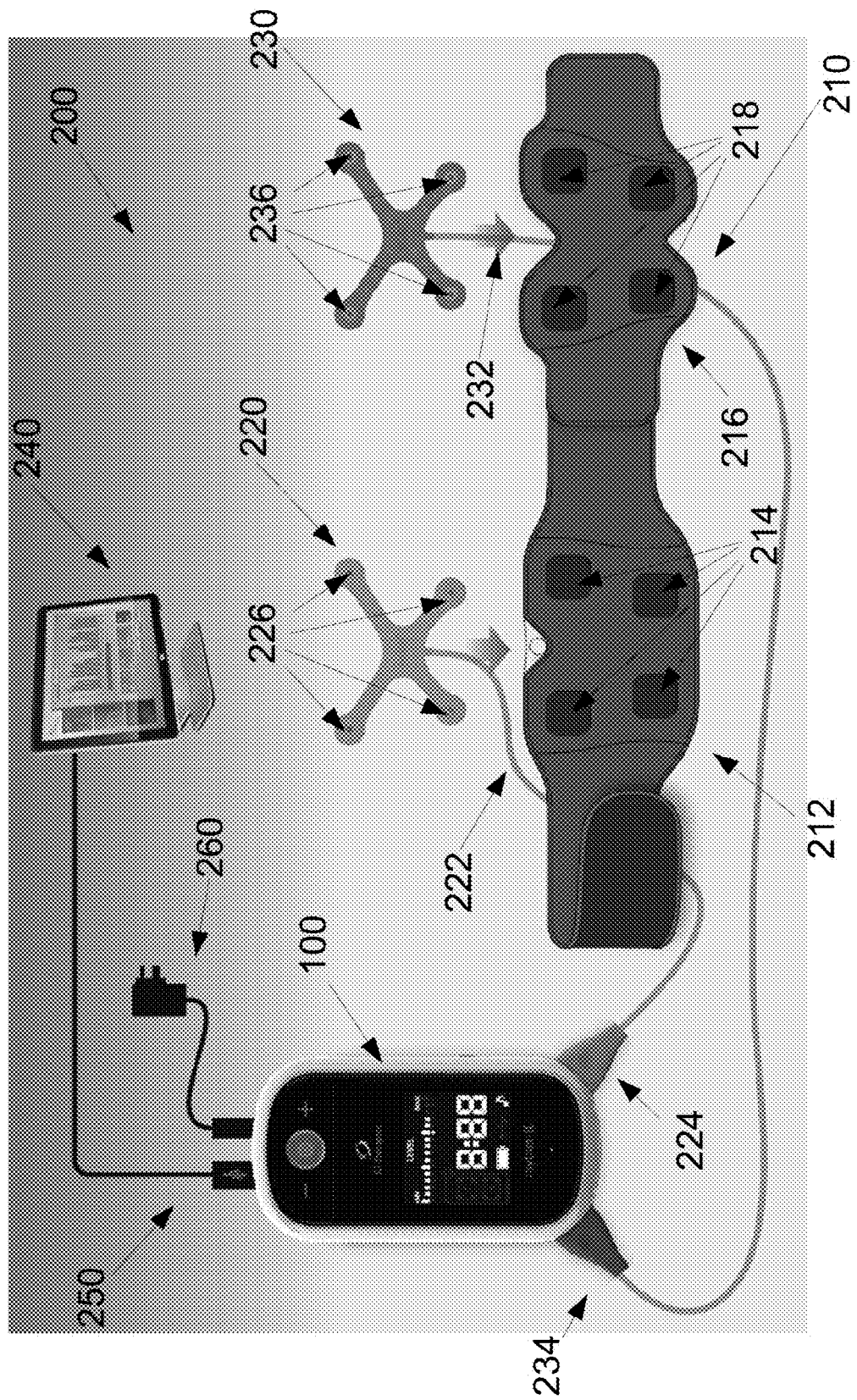
FIG. 2 shows a stimulation system including the stimulation device of FIG. 1.

Stimulation device 100 has connector inputs 160 and 165 located at and extending within corner portions of bottom end 120, and may be configured to deliver stimulation signals to electrodes electrically coupled to the connector inputs 160 and 165 (e.g. by connector jacks 224, 234 shown in FIG. 2). In some embodiments, connector inputs 160 and 165 may be positioned at an angle of about 90° to each other. The connector inputs 160 and 165 may respectively comprise sockets to receive respective connector jacks 224, 234 and the housing 105 may define recesses (not shown) at the corner portions of bottom end 120 within which the sockets extend inwardly of the housing 105. Plastic moulded end parts of the jacks can be at least partially received within the recesses. This configuration reduces the risk of the connector jacks coming loose from connector inputs 160 and 165 due to horizontal or vertical strain when the device is worn on the patient's body in the "upside-down" orientation where top end 110 is below bottom end 120.

In some embodiments, connector inputs 160 and 165 may be positioned at another angle to each other, such as an angle of between about 120° and about 60°, or of between about 100° and about 80°. In some embodiments, the angle may be about 90°. In some embodiments, the connector inputs 160 and 165 may be positioned at the corners of the bottom end 120 of device 100.

Stimulation device 100 may further include a clip 195 (see FIGS. 36a and 36b) that attaches to a belt or waistband of the user. In some embodiments, the clip may be a loop of wire that extends from bottom end 120 partly down the length of the body of device 100 and back to bottom end 120. The belt may be any conventional belt, or a belt specifically designed to hold stimulation device 100. The waistband may be a waistband of a garment such as a pair of pants or shorts, or a skirt. In some embodiments, another means of attachment to the body of a patient, or to a garment worn on the body of a patient, may be used. This may be a means of attachment to the patient's belt, waistband, or other garment. In some embodiments, the means may include multiple strips of mating Velcro, a series of snaps or buttons. Alternatively, the means of attachment may be a specially-designed belt or holster including a custom pocket designed to receive stimulation device 100 or clip 195. When the device is worn on the body of a patient, the device may be worn such that top end 110 hangs below bottom end 120. When worn in this way, device 100 hangs in an orientation where screen 130 is upside-down (with top end 110 below bottom end 120) and facing away from the body of the user.

To read screen 130, the user can flip device 100 upward about a pivot point, being the flap or portion on garment 210 (FIG. 2) from which device 100 is hanging. Flipping the free end (top end 110) of device 100 in this way allows an orientation of device 100 whereby the screen 130 is facing more towards the body of the user and is right-side up (with top end 110 away from the body and bottom end 120 close to the body) for normal viewing by the user. Thus, the top end 110 can swing freely about its attachment point to the garment 210 while the bottom end 120 is held close to the body. When the person wearing the garment 210 and the device 100 sits down, there may be a natural tendency for the device 100 to change orientation so that the display screen 130 become inverted enough (from its normal downwardly hanging position) to be readily readable by the person.

Stimulation device 100 may be configured so that when it is being worn in an orientation where top end 110 is held close to the user's body and bottom end 120 is swinging freely below top end 120, the display shown by screen 130 appears upside-down to an observer looking at the user. When stimulation device 100 is flipped up by the user about the pivot at the bottom end 120, the display shown on screen 130 may appear right-side-up to the user as the user glances down at the device 100.

In some embodiments, screen 130 may be configured to change the orientation of the data it displays based on input from an accelerometer, so that any text or images on screen 130 are the correct way up for reading or viewing regardless of the orientation of stimulation device 100.

Stimulation device 100 may include an internal power source, such as a battery pack, allowing it to be portable. Stimulation device 100 may further include a power input 150 to receive the connector of an external power source, which may be a plug pack to be plugged into a mains power source. The external power source may be used as a way of charging the internal power supply. Stimulation device 100 may further include a USB port 140 for the receipt of a USB cable for communication to external computing devices.

Stimulation device 100 may include input means such as buttons, a touch screen, or switches. In some embodiments, stimulation device 100 has a minimal number of buttons, such as only 3, 4 or 5 buttons. This makes the device relatively easy to use and less confusing for the user. In the illustrated embodiment, stimulation device 100 has power button 170, treatment level decrease button 180 and treatment level increase button 185, as well as volume slide switch 190. This allows the user to power the device on and off, to adjust the level of stimulation administered, and to turn the volume of notifications and alarms on and off.

LCD segment display screen 130 provides a visual means of communicating the status of various settings of stimulation device 100 to the user. LCD segment display screen 130 may have between 60 and 90 segments, and in some embodiments may have in the order of 73 segments. Treatment level display bar 132 shows the level of treatment being administered by the device, with the amount of the bar illuminated indicating the relative strength of the stimulation pulses. Time remaining display 134 is made up of several seven segment displays arranged to display a time in hours and minutes. These displays can also be configured to display scrolling characters, which may be used to display messages to the user, such as when a treatment cycle has finished, or a greeting message when the device is powered on, for example. Sound indicator 135 may be illuminated when the sound is turned on by switch 190, and turned off when the sound is off. USB connection indicator 136 may be illuminated when a USB connection is detected through USB port 140, and turned off when there is no USB connection. Battery indicator 137 may be illuminated when the battery power is sensed as being low, indicating that the device battery should be charged by connecting to a power supply through power input 150. In some embodiments, a replaceable battery may be used, and battery indicator 137 may be illuminated when the device battery should be replaced. The battery symbol may be displayed as full during the treatment stage. Pad fault indicator 138 may be illuminated when stimulation device 100 senses that at least one of the front and back electrode connector assemblies 220/230 is disconnected from the device.

Device 100 may further include LEDs as an additional method of visual communication with the user. In the illustrated embodiment, LED 321a may be a green LED used to illuminate power button 170 to indicate that the device is on. LED 321b may be a yellow LED used to indicate that the device is administering treatment. In some embodiments LED 321b may be of a different colour, such as orange.

FIG. 2 shows a stimulation delivery and monitoring system 200 according to some embodiments. System 200 includes stimulation device 100, which is electrically couplable to a back electrode connector assembly 220 and a front electrode connector assembly 230 by back and front electrode connection cables 222 and 232. Back and front electrode connector cables 222 and 232 connect to device 100 through back and front cable connectors 224 and 234, via connector inputs 165 and 160. In some embodiments, the stimulation generation device 100 is arranged to transmit electrical potential to the back and front electrode connector assemblies 220 and 230 via the connector inputs 165 and 160 and the back and front cable connectors 224 and 234.

Back and front electrode connector assemblies 220 and 230 may be attachable to a garment to be worn by a patient being treated. In the illustrated embodiment, the garment may be a belt 210, consisting of a back belt portion 212 and a front belt portion 216, attachable to each other by a temporary fastening means such as Velcro tape, allowing for an adjustment in size to match the body of the wearer. Back and front electrode connector assemblies 220 and 230 each have multiple electrode connectors 226 and 236. In some embodiments, each electrode connector assembly may have two, four or six electrode connectors 226/236. Back and front electrode connectors 226 and 236 are removably couplable to back and front belt portions 212 and 216 by mating snap connector parts (not shown) coinciding with back and front belt electrode placement pads 214 and 218.

Stimulation device 100 may be electrically couplable to an external power source, which may be an AC/DC plug pack 260 to plug into a mains power supply. The external power source may be used to recharge any batteries that are used to operate the device. AC/DC plug pack 260 may be electrically coupled to stimulation device 100 by a cable plugged into power input 150 of the device. Stimulation device 100 may further be electrically couplable to a computing device 240, which may be a desktop computer, laptop computer, tablet, smartphone, or other device. The coupling may be by connection with USB cable 250 between USB port 140 on the stimulation device, and a USB port on computing device 240. This connection may allow for communication between stimulation device 100 and computing device 240 via USB protocol, allowing for the adjustment of treatment settings, and the monitoring of the history of treatment given by stimulation device 100.

In some embodiments, device 100 logs data and records treatment history into an on-chip memory which may later be accessible by computing device 240. Such data may include information about a treatment session, such as the treatment duration, the date the treatment was administered, the time the treatment was administered and the intensity of the stimulation signals delivered during treatment. Communication between stimulation device 100 and computing device 240 may alternatively be achieved through a wireless protocol, such as Bluetooth or Wi-Fi, or through an alternative wired communication protocol. Alternatively, communication between stimulation device 100 and computing device 240 may be effected via an intermediate device, such as a handheld computing device (like a smart phone). Furthermore, the communication may be achieved via a telecommunications network, or via the Internet.

Figure 3:
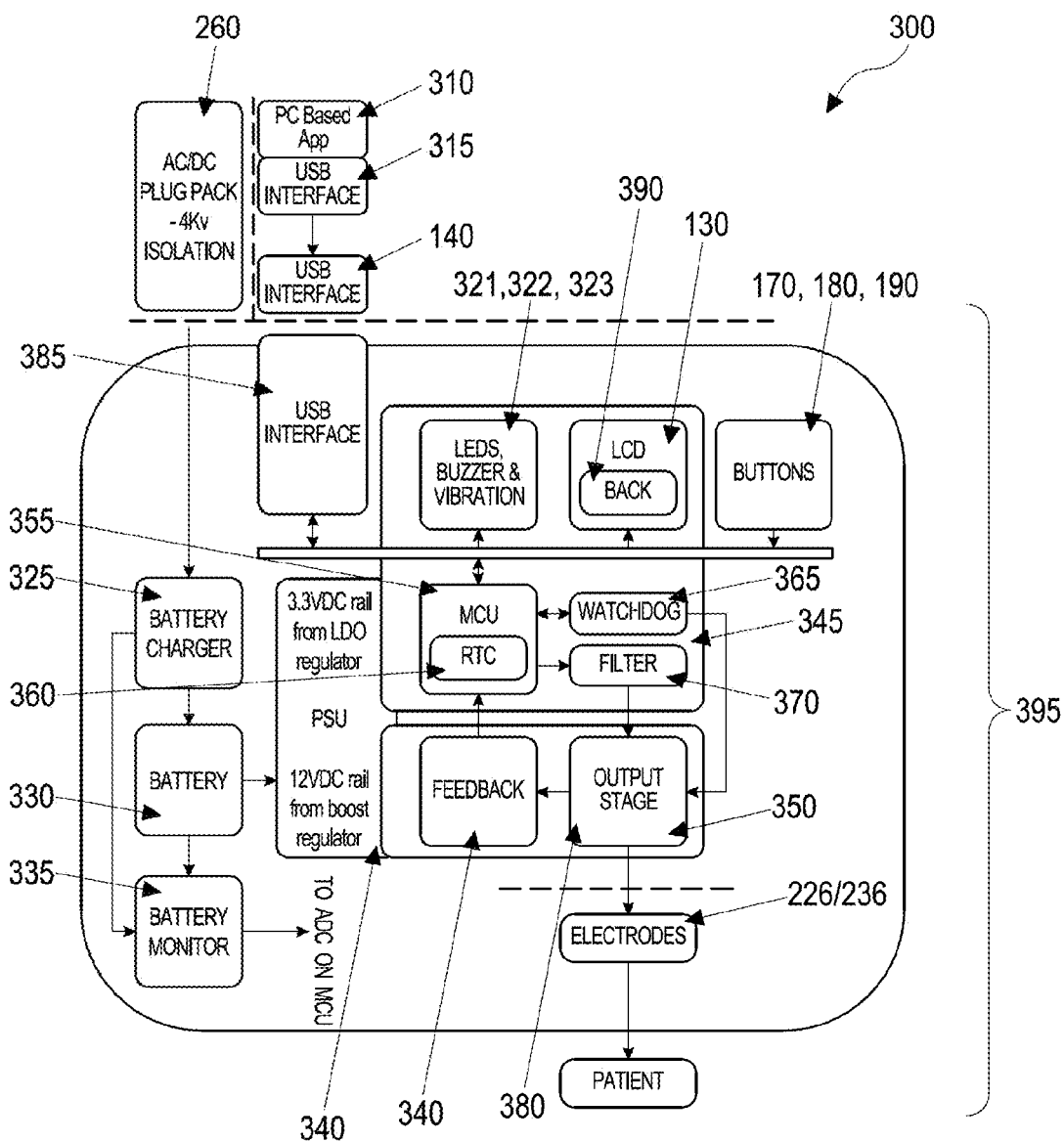
FIG. 3 shows a block diagram of the electrical components of the stimulation device of FIG. 1.

FIG. 3 shows a block diagram of electronic circuitry 300 contained within housing 105 of some embodiments of the stimulation device 100. AC/DC plug pack 260 is electrically coupled to battery charger 325. Plug pack 260 may be in the range of 4.5 to 5.5V. Battery charger 325 charges battery 330, which may be by trickle charging or by high current charging. Battery charger 325 may be connected to battery 330 through a charge management controller within battery charger 325. Potential voltage ripple may be filtered by a capacitor, which may be in the order of 10 µF in some embodiments. Battery charger 325 may be the Linear Technologies LTC4001 in some embodiments.

Battery charger 325 provides charging data to battery monitor 335. Battery monitor 335 monitors the battery voltage through a voltage divider, which may consist of two 150 kΩ resistors in some embodiments. The resultant voltage, equivalent to half of the battery voltage, is then presented to an ADC port of microcontroller 355.

Battery charger 325 may have overvoltage and reverse polarity protection circuitry, which may allow charging between the ranges of 4.5 to 5.5V, but inhibit voltages above 6V and up to a practical working voltage of 12V from reaching the charger. This may be implemented using an overvoltage protector such as the Linear LTC4360-2 or the Linear LTC4361-2.

Battery 330 supplies power supply unit 340, which may consist of two voltage rails 345 and 350. Rail 345 may be a 3.3 VDC rail supplied from a low drop-out or a Buck/Boost regulator, and is used to supply the logic and microcontroller 355. Rail 350 may be a 10 VDC rail or a 12 VDC rail in some embodiments, supplied from a boost regulator, and may be used to supply output stage 380. The boost converter may be configured to supply any voltage between 10 VDC and 15 VDC. Device 100 may include power plug protection to detect whether or not AC/DC plug pack 250 is connected to battery charger 325. In some embodiments, this data may be sent to microcontroller 355, which may disable the boost converter supplying 10 VDC or 12 VDC rail 350 when AC/DC plug pack 250 is connected, to disable electrode connectors 226 and 236 from delivering stimulation pulses while device 100 is charging. In some other embodiments, the stimulation pulses may be disabled in hardware through an external power plug connection input.

Microcontroller 355 may be from the STM32F1 family of microcontrollers, and may include peripheral support for a UART for debugging purposes, a USB controller, real time clock 360, at least 2 digital-to-analogue converters (DACs), in the order of 2 to 6 analogue to digital converters (ADCs), and a serial peripheral interface for an LCD controller. Microcontroller 355 communicates with watchdog 365 to limit the likelihood of a system failure caused by a runaway controller. Watchdog 365 may perform functions including monitoring microcontroller 355, resetting microcontroller 355 if watchdog 365 is not serviced within an allowable time interval, latching a reset event to be visible to microcontroller 355 for logging reasons, and latching off output stage 380 during a reset event to prevent device 100 from continuing to deliver stimulation pulses through electrode connectors 225 and 236 until this is cleared by microcontroller 355. Watchdog 365 may be ST Microelectronics STWD100PY. This may be connected to hard reset circuitry to allow for a reset of the device when required. In some embodiments, watchdog 365 may be a watchdog internal to microcontroller 355.

Microcontroller 355 has access to memory (not shown) within the device 100. The memory may include ROM, RAM, flash, or other memory types. The memory may store instruction code, firmware image, configuration parameters and logged history data for device 100. Device 100 may make the contents of the memory available to computing device 240 when device 100 is connected to communicatively computing device 100, which might be through a physical connection with USB cable 250 in some embodiments.

A PC based application 310 may be run on a computing device 240 to communicate with device 100 through a USB interface. This communication may allow for a user using computing device 240 to set up settings of device 10, such as the treatment durations and levels. Computing device 240 may have USB interface 315, connectable through to USB port 140 of the device through a USB cable 250. USB port 140 is isolated from patient contacting part 395 of device 100 through an isolation component 385, which may be a 4Kv I-coupler in some embodiments, such that the USB interface is used for data exchange only. USB port may be required to be USB 2.0 compliant, and EMC compliant.

Microcontroller 355 may communicate to user interface components of device 100 such as LEDs 321, buzzers 322 and vibration motor 323, an LCD display 130 which may include backlight 390 and buttons 170, 180 and 185. LEDs 321 may be used to illuminate power button 170 when the device is on. A buzzer 322 may be used to play alerts and alarms to the user to indicate the start and/or end of treatment cycles. The chassis of device 100 may be designed to have an acoustic cavity to amplify the sound emitted from the buzzer 322. The buzzer 322 may be disabled by the user by switching volume slide switch 190. In addition or alternatively to the buzzer 322, a vibration motor 323 may be used to alert the user by vibrating the device. This may be used in conjunction with the buzzer 322, or may be turned on only when the device is in silent mode.

Microcontroller 355 controls the power supplied to output stage 380, driving this through its DACs. Output stage 380 may include circuitry configured to generate transcutaneous stimulation signals. Output stage 380 may have two output channels, which may be a 4 kHz channel and a 4 kHz plus 180 Hz channel. In some other embodiments, these may be a 4 kHz channel, and a channel sweeping between 4080 and 4160 Hz. Filter 370 may be used to achieve a flat frequency response in the pass band, which may be in the order of 3800 Hz to 4200 Hz, centred around 4000 Hz. Filter 370 may be a two stage, four pole filter, to provide a reasonably fast roll off with minimal component count. Output stage 380 receives input from filter 370 and may drive output transformers. There may be one transformer for each electrode connector 226 or 236. For example, where there are 4 electrodes, there may be 4 transformers. Where there are 4 transformers, in some embodiments only 2 transformers may be active at any given time. Further functions and operation of a 4 transformer design are described below with reference to FIG. 34.

The secondary winding of the transformers may include short circuit protection implemented by PTC (positive temperature coefficient) devices, other resettable fuses or resistors. These provide current limiting which reduce the impact of a short circuit condition. In some embodiments, the output current may be limited to 100 mA, for example. The operation of output stage 380 and the output transformers may further limit the maximum output voltage in open circuit or under very high impedance. In some embodiments, this may be limited to 500V, for example. Furthermore, output stage 380 and the output transformers may allow for other safety requirements to be met. For example, output stage 380 may limit the maximum current delivered into a 1KΩ load, which may be limited to 55 mA peak-to-peak in some embodiments. In some embodiments, the hardware of the device provides safety features to limit the harm to a patient that can be caused by the malfunction of the software or firmware of the device.

Output stage 380 supplies data to feedback circuitry 375, which communicates with microcontroller 355 to ensure the correct stimulation level is being delivered. Feedback circuitry 375 may allow for the detection of connectivity of electrode connectors 226 or 236, and alert the user and/or stop delivering stimulation signals when the electrodes become disconnected. This detection may be based in software, calculated using the magnitude of the generated sine wave by a DAC of microcontroller 355 and a measured RMS primary current, in some embodiments.

The design of the device 100 and system 200 is such that patient safety is assured by hardware. The firmware and software may also be configured to provide additional levels of safety to the patient.

The device 100 may minimise power consumption in two ways: utilising modes of microcontroller 355, such as Stop and Sleep modes of STM32 processor, whenever idle, and switching off peripheral devices whenever they are not in use. The microcontroller 355 may be put into Sleep mode whenever it is idle but its peripherals are in use (e.g. during treatment), to be woken via a facility such as the STM32 Wait-For-Interrupt facility. A low-priority thread (the Sleep Manager daemon) will when executed:

Disable the scheduler to prevent higher-priority threads from executing until the SysTick service has been re-enabled;
Disable the SysTick service;
Enter a low-power mode.

It is necessary to use an application thread (the daemon) to handle this rather than simply augment the system idle thread as RTX calls cannot be made from the Idle thread. The microcontroller 355 exits Sleep mode on interrupt from any of the following peripheral devices:

Real-Time Clock (RTC)—scheduled alarm;
External power applied/removed;
General Purpose Input Output (GPIO) Interrupt (for a button press);
USB SOF present.

On exit from the appropriate interrupt service routine, the processor 355 will resume normal execution. Servicing of the interrupt may have left a client thread in the runnable state, in which case it will be scheduled immediately; otherwise the Sleep Manager daemon thread will be scheduled (again). In the latter case, the microcontroller will immediately re-enter Sleep mode.

When the main Command thread detects that there is no application work to do, the Device will enter an even lower power mode, "stop". In this mode, as well as halting the CPU, the microcontroller 355 will stop clocking most internal peripherals. This state will be exited by one of four events:

RTC tick alarm (for servicing the watchdog)
Power button being pressed
External power being connected
USB receiving SOF indications.

Applications within the device 100 may be configured to ensure minimal power consumption by only enabling those peripherals (internal and external) as and when required. Thus, by the time the command thread enters stop mode, most peripherals will already be switched off. Microcontroller 355 may have modes to preserve the contents of Ram. For example, the STM32 Power modes to be used, Stop and Sleep, both preserve the contents of RAM. In some embodiments, power usage may be minimised by shutting down the core of microcontroller 355 when treatment is not being administered.

Device 100 may utilise the on chip real-time clock to provide a tick source for executing the OS and associated timers. The real-time clock can be set via the USB host communications interface either during manufacturing or by a clinician. A consequence of the processor sometimes entering Sleep mode is that the RTX SysTick interrupt will not occur and all RTX-based timers will not accurately reflect real time. The firmware must employ timers to manage its real-time obligations, such as timeouts, so the on-chip Real-Time Clock (RTC) will be used as the time source for all firmware operations.

The architecture of device 100 may employ concurrency to allow each communications interface to be managed in relative isolation from the rest of the firmware system. This may be handled by multithreading, with separate threads to handle the various communications sources. In the majority of cases, each thread will have an 'in-bound' message queue that other threads may use to communicate with it. The firmware complexities often associated with thread synchronisation will be handled primarily by isolating all thread interactions to a small number of utility classes, allowing the bulk of the code to be oblivious to the multithreaded environment.

Inter-Process Communication (IPC) mechanisms may be hidden behind the firmware interface for a given component, and thus the chosen IPC implementation may be free to change without affecting the abstract interface between any two components, i.e. a client will not know that a message queue is being used as the IPC mechanism. The architecture of device 100 may generally decouple the firmware components to give maximal flexibility with regard to how they are integrated together to form a working system. The firmware may be divided into layers of logical dependency such that a firmware component will have a compile-time dependence only on other components that reside in the same or lower layers of the architecture. There may also be a run-time decoupling of physical dependency between major architectural components, based on dependency injection. For example, where object A requires the services of object B, the service provided by object B will frequently be abstracted behind an interface and object A will be injected with an interface pointer (or reference) to the abstract service. Thus construction of B will be hidden from A, which will preserve A's flexibility to be provided with alternate implementations of the service. In keeping with this theme, use of the Singleton pattern will be kept to a minimum and where possible the location of such global resources will be injected into their clients, thus avoiding the need to search for them. This approach will allow a variety of different executable images to be built, with minimal code differences between firmware components common to different executable images. This should facilitate unit testing of individual components through stubbing of other components.

The firmware may be upgraded in the field, via the USB host communications interface. For this purpose, the architecture:
Ensures that there is sufficient memory to enable a second code image to be held temporarily
Ensures that the Flash memory can be reprogrammed by the Device firmware itself.

A new firmware image for the microcontroller 355 can be downloaded over USB and stored in a special area of the internal flash. The firmware will be restarted and the bootloader will detect the upgrade image in the secondary area, and re-program the primary internal flash of microcontroller 355 with the new firmware. On completion, the firmware will be restarted to boot the new firmware version. Should the transfer of firmware image from external to internal flash be interrupted, the bootloader will re-attempt the re-programming at the next power-up. The device 100 memory map identifies the storage and/or execution regions for the microcontroller 355 firmware. The upgrade facility may operate on a "complete" upgrade package, replacing the entire existing image with a new complete image.

External host communications are programmed to support:
Firmware upgrade;
Clinical configuration of treatment parameters;
Test result record transfer, including patient test results and fault log.

The firmware may operate based on a simple event handling model where each thread will wait on a set of event flags for an event to be signalled. The event sources can be internal as a result of IPC, i.e. a message being posted to a threads input queue or an external event where a device has asserted some condition of interest. In the latter case, the condition is detected by the associated device driver and translated into an internal event and dispatched to the appropriate thread. Taking the case of a device interrupt, the driver will handle the interrupt (satisfying the devices requirements) and shall then signal a client by setting the event flag supplied by the client at run-time. A similar mechanism is used when a driver is requested to complete an operation for which the client thread does not wish to block. Instead it requests that the driver set the specified event flag when the asynchronous operation is complete.

The event management mechanism is structured such that each thread can wait on up to sixteen separate events flags, thus at least sixteen separate events (although some events could be signalled by a combination of events). A priority scheme has allocated each firmware thread based on the frequency of key input events.

As an example, the device 100 hardware may provide the following memory resources:
96 KB on-chip RAM;
768 KB on-chip Flash.

In some embodiments, no external memory will be present, so the firmware design may be constrained to fit within the internally available resources. A 'two-region model' may be used for heap and stack and the on-chip RAM may be divided between these two regions:
the allocation of 'system objects' (threads, stacks, semaphores, etc.) that have a persistence roughly equal to the run-time of the product, i.e. they are created at power-up and never destroyed by the firmware;
A small amount of RAM will be used for statically-allocated data, primarily as required by the compiler and run-time library. During bootstrap, space will be reserved for the statically-allocated data (identified by the linker as read-only, zero-initialised or general read-write data). Driver objects and their associated buffers will be created in on-chip RAM from a special memory pool.

The on-chip RAM may also be used for:

The per-thread call stacks;

The system heap from which dynamic allocations will take place (for non-system objects).

While dynamic allocation cannot be eradicated from the firmware, it is required where possible that allocations be made once at initialisation time and never de-allocated. By moving to this more static model, it is expected that the memory utilisation will be easier to monitor and control, providing the essential data for any subsequent optimisations to take place.

The on-chip flash memory may be used for the storage and in-place execution of the bootloader and the main application program code. The flash may be accessed 'raw' with no real file system in place. While providing ease of development, a full blown file system would consume considerable resource and also prevent efficient use of the underlying flash memory. As such, wear-levelling must be considered and factored into the design of individual components which require flash access. Essentially three types of data/style of access may be used:

Program code: changing infrequently/wear-levelling not a concern;

Clinical settings: changing at low frequency/wear-levelling not a concern—as these are only changed by a clinician or health care practitioner, they are unlikely to be changed more than once a month or 36 times over the product lifetime;

Patient Test Results: changing at higher frequency/wear-levelling still not a concern—the Device allocates space for 180 treatment records, which are all erased by a clinician and subsequently filled up at the rate of once per treatment.

In all cases, the maximum number of erase/write cycles for each area is expected to be less than 100 over the lifetime of the product. Therefore, no wear-levelling is required.

To allow concurrent write/erase operations on data areas and program execution, a two-bank microcontroller is specified. The code image being executed is located in the second back, allowing slow operations (write and erase) to block accesses to the other bank without affecting normal driver operation. Components using the Flash which might be blocked by such data operations may be designed to avoid being blocked at inconvenient times.

Figure 4:
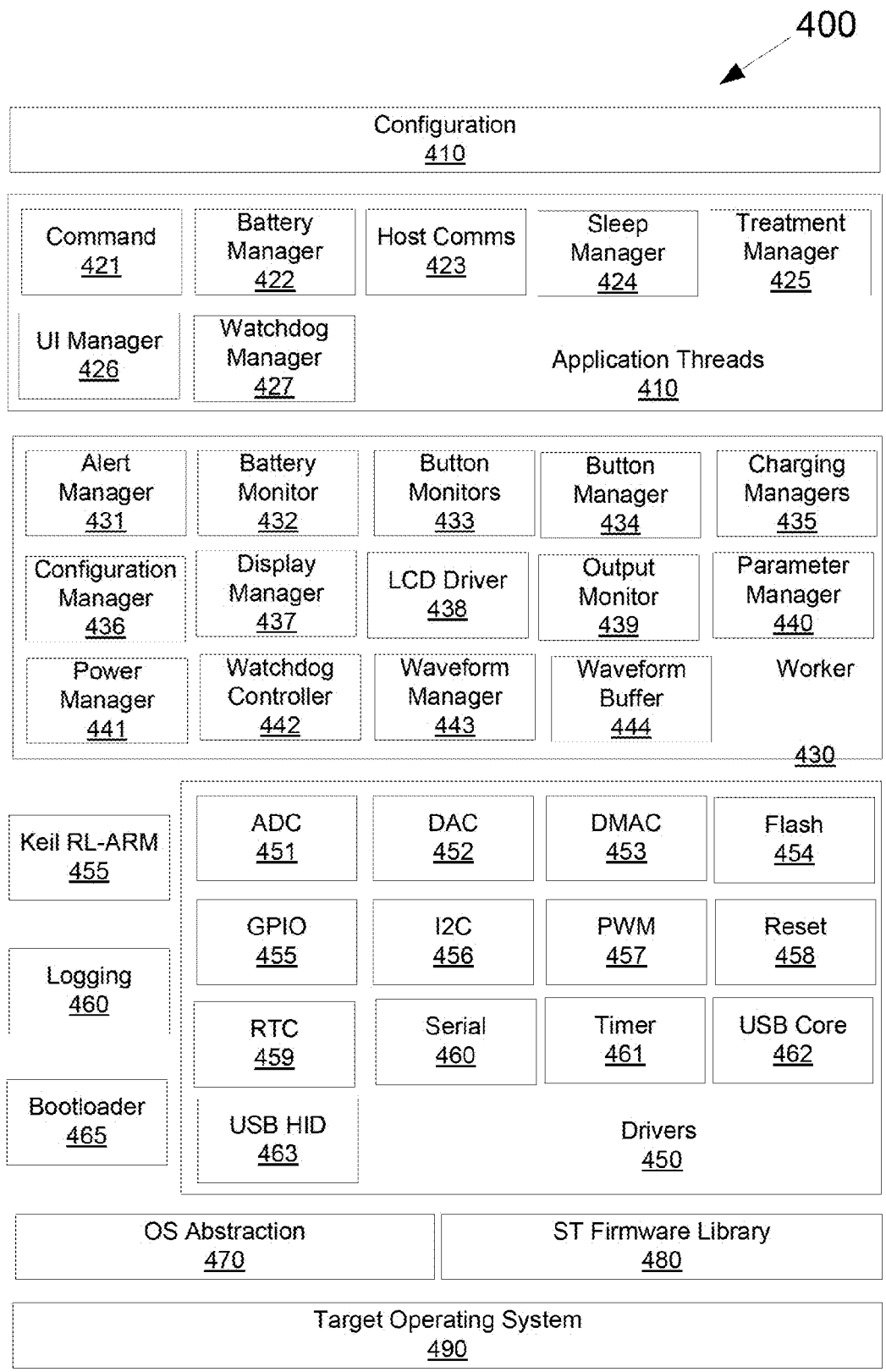
FIG. 4 shows a block diagram of the firmware components of the stimulation device of FIG. 1.

FIG. 4 shows a block diagram of firmware 400 of stimulation device 100. Firmware 400 runs on microcontroller 355 atop an operating system, which in some embodiments may be a real-time operating system (RTOS) such as the Keil RTX RTOS.

Configuration component 410 is responsible for determining the application firmware configuration to be executed, comprising the concrete objects instantiated behind key abstract interfaces as well as the threads to be run. The key abstract interfaces may relate to initialisation for a specific target operating system, the selection of drivers to be started and their specific implementations, and concrete instances of OS Abstraction components. Configuration component 410 has compile-time dependencies across the entire set of firmware components and allows many firmware components to be isolated from other firmware components by using a dependency injection design pattern to manipulate the dependencies.

At the application level, application threads 420 provide the core logic of the firmware and manage the therapy, power management, user interface and host communications. Command thread 421 provides the finite state machine model for the behaviour of device 100 and manages, from a high level, all interactions with peripheral devices. Battery manager thread 422 monitors the voltage level of battery 330 and the presence of a power source connected to battery charger 325, and runs the charging process. Host communications thread 423 handles communications with the external USB-connected host, which may be computing device 240, and provides a context for the protocol layers to function. Sleep manager thread 424 temporarily suspends microcontroller 355 when there is no work to do. Treatment manager thread 425 is a top-level thread for overall control of a treatment cycle. UI Manager thread 426 is responsible for all user interface input and output, including buttons 170, 180 and 185, LEDs 321, buzzers 322 and vibration motor 323, and LCD 130. Watchdog manager thread 427 is responsible for ensuring that other system components are working correctly and servicing the watchdog 365 at suitable intervals.

Worker components 430 are a group of components that perform the functions of the device 100, executing in the context of one (or more) of the application threads 420. Alert manager component 431 controls the non-visual output devices, which may include the buzzer 322 and the vibrator motor 323 in some embodiments. Battery monitor component 432 monitors the level of charge in battery 330. Button monitor components 433 make up part of UI manager thread 426, and each instance monitors a single button 170, 180 or 185, debouncing, classifying and signalling to the button manager component 434. Button manager component 434 oversees the multiple button monitor components 433, extracting the key events for each button 170, 180 and 185, detecting button combinations and reporting events to other system components. Charging manager component 435 control and monitor the battery charging process. Configuration manager component 436 orchestrates the final configuration process. Display manager component 437 controls the visual output devices, which in some embodiments may include LEDs 321 and the segmented LCD 130. LEDs 321 may be controlled directly, while LCD 130 may be controlled indirectly via LCD driver component 438. LCD driver component 438 generates sequences of I2C messages to configure the LCD display 130 and to then enable/disable the entire display and individual segments. Output monitor component 439 tracks the transcutaneous interferential current stimulation therapy being provided to the patient and identifies pad connection faults. Parameter manager component 440 controls access to and integrity of system parameters. Power manager component 441 puts device 100 into the lowest possible power mode when it is between uses. The working components may include a watchdog controller component 442 to provide access to external watchdog 365 to protect key execution areas. In some other embodiments, an internal watchdog may be used. Waveform manager component 443 is part of the treatment process that uses waveform buffer components 444 to control the frequency and strength of the generated waveforms. Waveform buffer components 444 are used by waveform manager component 443 to create and hold the digital representation of a sine wave.

Firmware drivers 450 all share a common abstract interface defined by the OS abstraction component 470 and have individual derived (abstract) classes specific to their function, as well as further derived classes for the platform-specific implementation. This organisation allows some operations to be performed on all drivers 450 (e.g. during system initialisation) and device-specific operations to be performed on drivers 450 by client threads that are oblivious to the specific operating system and hardware platform. Each driver 450 will provide an application program interface (API) that executes within the context of one or more client threads, as well as an Interrupt Service Routine (ISR) if required for the specific peripheral and shared data structures for communication between the ISR and the client thread. One or more instances of each driver class will be created as required. Client components will be injected by configuration component 410 with the driver objects they require.

ADC driver component 451 configures and reads the on-chip ADC peripheral. DAC driver component 452 configures and writes the on-chip DAC peripheral. DMAC driver component 453 configures and controls the Direct Memory Access Controllers. Flash driver component 454 reads, writes and erases functions for internal flash. GPIO driver component 455 controls the reading, writing and interrupt reporting for General Purpose Input Output (GPIO) signals. I2C driver component 456 writes configuration and control messages to the segmented LCD 130. PWM driver component 457 produces pulse-width modulated output on selected GPIO lines. Reset driver component 458 handles microcontroller 355 reset functions and the on-chip watchdog. RTC driver component 459 accesses on-chip real-time clock 360. Serial driver component 460 handles asynchronous communications via UART devices. Timer driver component 461 configures and manages the underlying timer implementation. USB core driver component 462 and USB HID driver component 463 give access to the USB peripheral.

Higher-layer components may reside atop these platform-specific drivers to bridge between application components and drivers.

Logging component 460 supports development by allowing configurable generation of execution trace messages which are output to a 'logging device', i.e. a serial port or a flash device. The firmware is divided into notional logging domains with each being assigned a logging threshold at start-up. The firmware executing within a logging domain can generate a log message at a specific level if that level exceeds the threshold configured for that domain. This allows for logging output to be generated at varying levels of detail to support debugging. In some embodiments logging may be able to be disabled, to reduce the run-time and code-space overheads where this may be particularly required.

Bootloader component 465 is responsible for initialising the platform. This may include establishing a run-time environment, completing any pending firmware upgrade operations, and verifying and booting the installed application. Bootloader component 465 keeps peripherals not required prior to application start-up in a low-power mode, i.e. reset, not clocked or off.

In some embodiments, firmware 400 may include Keil RL-ARM component 455, which may be a 3rd-party library that contains several middleware components. In some embodiments, the middleware components may include the RTX operating system. In some embodiments, firmware 400 may include alternative libraries and/or other middleware components.

OS abstraction component 470 provides abstract interfaces which isolate most of the firmware from the actual operating system and its underlying hardware. OS abstraction component 470 also includes implementations of those interfaces for target operating system 490, which may be Windows or RTX in some embodiments, and for the hardware platforms, which may include desktop PCs, STM32 platforms including evaluation boards, prototype TBCTD hardware and final TBCTD hardware.

In some embodiments, firmware 400 includes ST firmware library 480, being a Keil RTX-compatible ST Micro firmware library. Some embodiments may use alternative libraries compatible with other operating systems.

Target operating system 490 may be a 3rd-party Keil RTX Real-Time Operating System (RTOS) or Windows, or another operating system.

Figure 5:
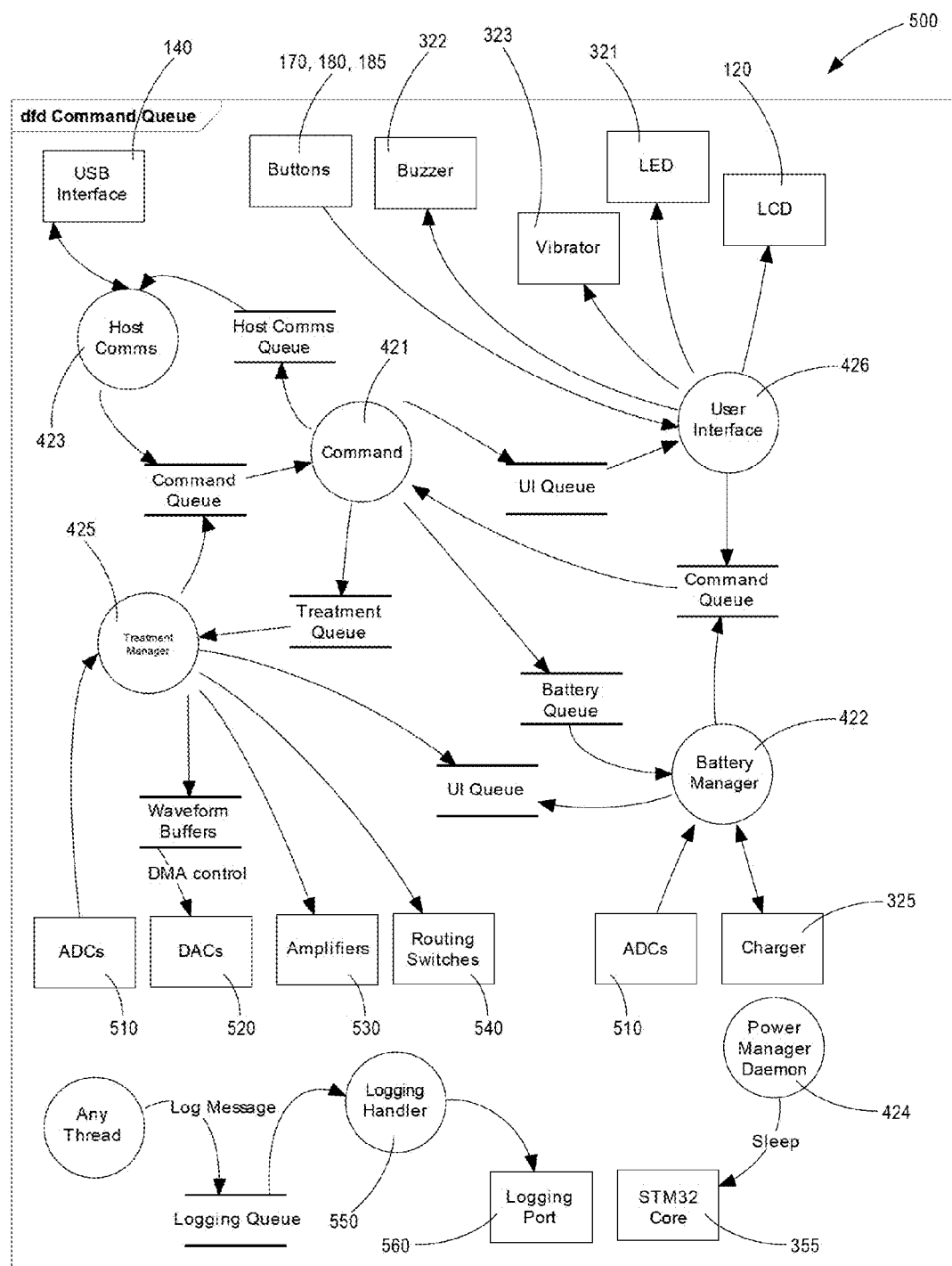
FIG. 5 shows a block diagram of the application threads and inter-process communication of the firmware of the device of FIG. 1.

FIG. 5 is a block diagram of the application threads and inter-process communication 500 of firmware 400 of device 100. Firmware may include a configuration thread (not shown). The configuration thread may be an initial thread launched by target operating system 490, and may serve to create all the necessary system resources and launch the application threads. Once the other threads have been started it may no longer be required and may be terminated by command thread 421. It is vital that this thread run at a priority higher than all others to ensure that it completes its execution before any other application thread is scheduled to run.

Command thread 421 provides a central control of device 100 and is stimulated by events being posted on its input queue and from timers created and maintained internal to the thread. Its primary tasks are: maintaining the system state; noting signals requesting or requiring state changes (e.g. charger being connected), selecting the highest-priority function to be run; stopping and starting applications; stopping the microcontroller to conserve power when the system is completely idle. Command thread 421 may receive messages and event status updates from a number of sources. For example, it may receive messages from battery manager thread 422 to communicate that the external charger is disconnected, or when charging is complete. It may receive messages from host communications thread 423 when the host communications become active or inactive, or when the firmware image is being updated. Treatment manager thread 425 may send messages to command thread 421 when a pad fault is detected, or when the pad status changes. Command thread 421 may also receive messages from user interface manager thread 426 to notify it of user input events (such as buttons 170, 180 or 185 being pressed) or of when output operations are complete. Command thread 421 may also receive asynchronous notifications, of events such as USB activity, activation of the power button, when AC/DC plug pack 260 is connected, timer ticks, and when the watchdog requires service.

Battery manager thread 422 may provide a number of services to device 100. These may include monitoring the voltage of the battery for the purpose of generating and reporting battery level/status alerts to clients, monitoring the connection and disconnection of the external power supply, and controlling the charging process. Battery manager thread 422 may receive a number of messages from other threads. For example, it may receive "start charging" or "stop charging" commands from command thread 421. It may also receive asynchronous notifications, of events such as when conversion is completed by an ADC, and of timer ticks. Battery manager thread 422 may be configured with settings to allow the battery 330 to maintain sufficient charge for up to 6 months to keep data, such as stimulation delivery data, in the device memory (not shown), in some embodiments. The battery 330 may be partitioned so that it does not go completely flat and can therefore maintain the clock and date functions in the data storage. In some other embodiments, the battery may be connected to microcontroller 355 via a voltage divider, to allow the core of microcontroller 355 to be shut down whenever treatment is not being administered, so that only the clock, date and data storage functions are maintained.

Host communication thread 423 handles all communications between device 100 and the external computing device 240 via the USB link 250. Host communication thread 423 may receive messages from command thread 421 when an operation succeeded or failed. Host communication thread 423 may also receive asynchronous notifications due to interrupt driven events, such as notifications from of USB activity, USB idleness, and whether messages were received via USB.

Sleep Manager thread 424 is the lowest priority thread in the system and executes when there is no higher-priority application work to be done, putting microcontroller 355 into its Sleep mode. This priority structure results in an automatic shutdown of device 100's CPU (but not its peripherals) into a low-power mode when there is no outstanding application work to be done. This thread essentially halts the system using the wait-for-interrupt command and thus the last instruction to get executed upon entry to the low-power mode will be within the context of this thread and likewise be the first instruction executed at exit from the low-power mode.

An even lower power mode, Stopped, may be used when the Device is completely idle; this stops the CPU and internal peripherals as well as powering-down external circuitry. These two schemes are complementary: one saving power during operations, the other saving power between operations.

Treatment manager thread 425 is the top-level thread for providing treatment, being the provision of stimulation signals to electrode connectors 226 and 236. Primarily, this thread decides when treatment starts and ends, and the parameters for the treatment; it then instructs other components to perform various aspects of the treatment process (generating frequencies at specific levels to specific pads); it also reports progress to the UI and records treatment record to Flash. It also implements the final treatment start level configuration stage, where a new patient selects a desired start treatment level. Treatment manager thread 425 may monitor the therapy being received by the patient to detect pad connection faults. If a fault is detected, treatment may be suspended and the patient may be alerted. Treatment manager thread 425 may receive messages from command thread 421 telling it to stop or start treatment, or informing it of user input events, such as button presses. Treatment manager thread 425 may further receive asynchronous notifications due to interrupt driven events. For example, some of these events may include completion of conversion or errors during conversion by DACs or ADCs, and notifications from the timer service based on duty cycle service timers, direction change timers, frequency change timers, output check timers and level change timers.

User interface manager thread 426 may comprise two main strands, being the UI manager and the display manager. The UI manager may be a top-level component, interfacing between all the UI threads and other modules, and performing some sequencing operations within the UI module. The display manager may run the visual UI. Inputs may come from various sources, and a number of output devices are under user interface manager thread 426's control. For example, UI manager thread 426 may display the elements and data requested in the specified formats; sequence animations if required; and drive the LCD power and backlight in accordance with the user settings, user interaction and as requested by the command thread 421. UI manager thread 426 may receive a number of messages from command thread 421, including requests to signal a specified treatment level, a specified reference level, a pad fault pattern (or no fault), a time period, a warning, power, battery level, a low battery condition, that treatment is complete, an error condition, a key-click, an at-limit condition, the introductory message, or that the default level has been set. It may also receive requests to enable LCD 130, to disable LCD 130, to enable LCD's backlight 390, to display a specified format, or to display a specified string of text. It may also receive messages and notifications from the UI alert manager and UI button manager threads.

The UI alert manager is a thread within the UI module. It runs the non-visual UI outputs, namely the audible buzzer 322 and the vibrator 323. It may be responsible for functions such as generating the required sequences; using the "mute" switch position to decide if audible output is required; and driving the two output devices.

The UI button manager thread is another thread within the UI module. It monitors the push buttons operated by the user, which are connected to GPIO (input) pins on the microcontroller 355. These inputs are de-bounced and gated, and then trigger event messages to other threads.

The UI LCD driver thread is a further thread within the UI module. It is responsible for sending configuration commands via the I2C driver, which may be sent at start-up, to configure the device for use; during device operations, to turn the display on and off; and during device operation, to turn individual segments on and off.

Watchdog manager thread 427 manages the on-chip watchdog by resetting it when commanded to do so. The thread simply blocks on a semaphore and this semaphore is posted by a client thread when it is time to service the watchdog. The watchdog strategy requires that this thread have a priority of one higher than sleep management thread 424 and the commanding thread be of a significantly higher priority in the process set and also be a thread that runs frequently. In some embodiments, command thread 421 may be the commanding thread. The resultant priority structure sees a high priority thread being required to run to activate the watchdog thread which itself is low priority and thus if the watchdog is being correctly maintained then one can be reasonably confident that neither deadlock nor priority inversion is taking place (for a significant period of time).

Logging thread 550 collects log messages on behalf of the other threads and writes to logging port 560 to output the log messages. The underlying device could log to a serial port or to flash for example—logging thread 550 is not concerned with the underlying implementation of logging port 560.

Competing with the application threads is the firmware executing within the various Interrupt Service Routines (ISR). Nested (parallel) interrupt handling may be used to ensure that the most time-critical interrupts are serviced in a timely manner.

Figure 6:
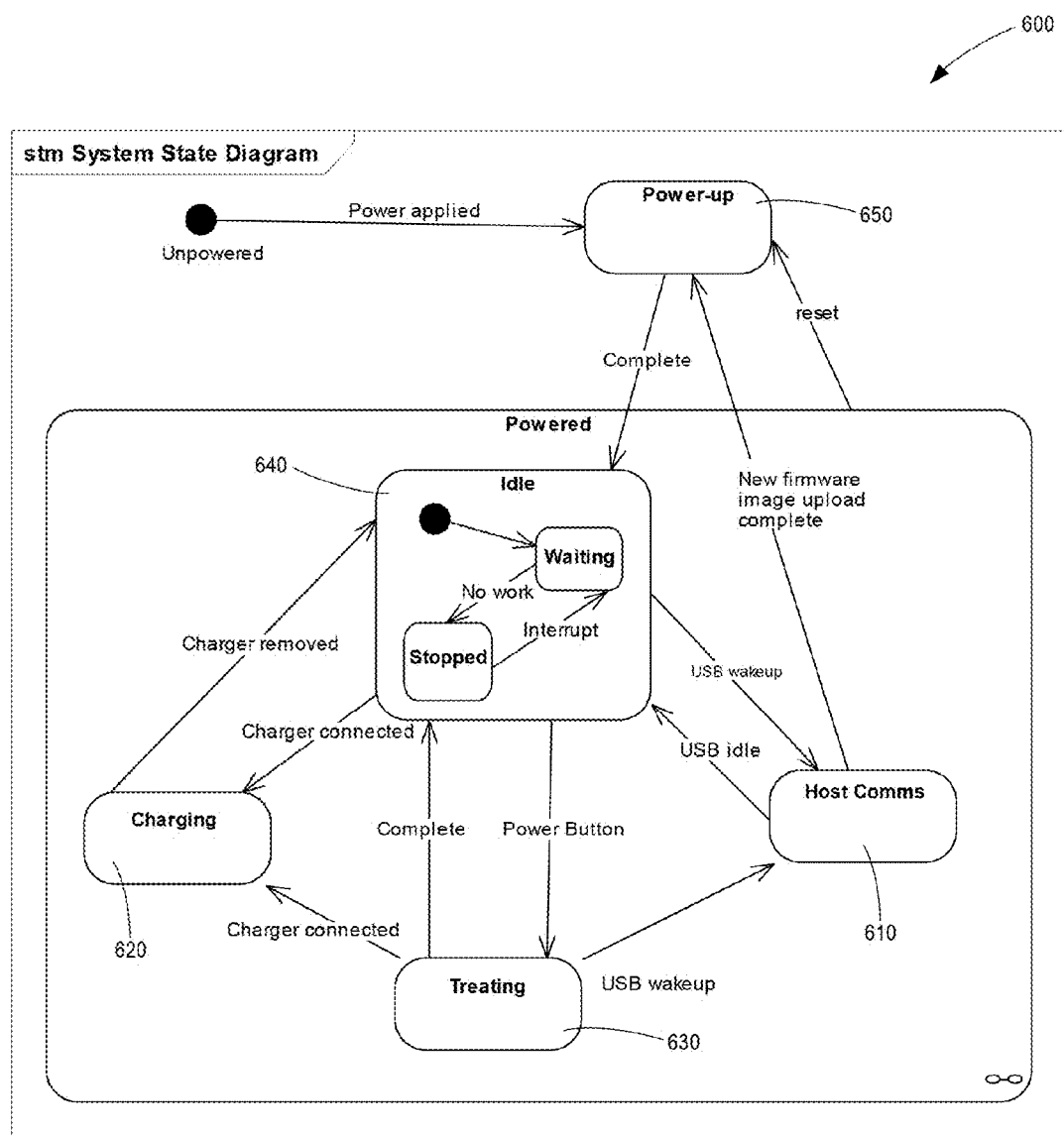
FIG. 6 shows a state diagram illustrating the system states of the device of FIG. 1.

FIG. 6 shows a state diagram illustrating the system states 600 of device 100. Device 100 may be configured such that firmware 400 operates in one of four mutually-exclusive modes, implemented by command thread 421. In some embodiments, these may be host connected mode 610, charging mode 620, treatment mode 630 and idle mode 640.

In host connected mode 610, device 100 may be inoperable to the user and may be under the control of a host application run on USB-connected computing device 240 for the purpose of retrieving test results, device information and configuration data from device 100; updating configuration data stored on the device 100; and transferring a new firmware image to device 100. In charging mode 620 device 100 may be connected to AC/DC plug pack 260. In treatment mode 630, device 100 may be supplying electrical stimulation signals to electrode connectors 226 and 236 in order to provide transcutaneous stimulation to a patient by way of treatment. In idle mode 640, device 100 may not be performing any tasks. In some embodiments, this mode may consist of two internal modes, being waiting mode 642 and stopped mode 644, which device 100 may transition between based on an interrupt event. Device 100 also enters power-up mode 650 when powered up or reset.

Figure 7:
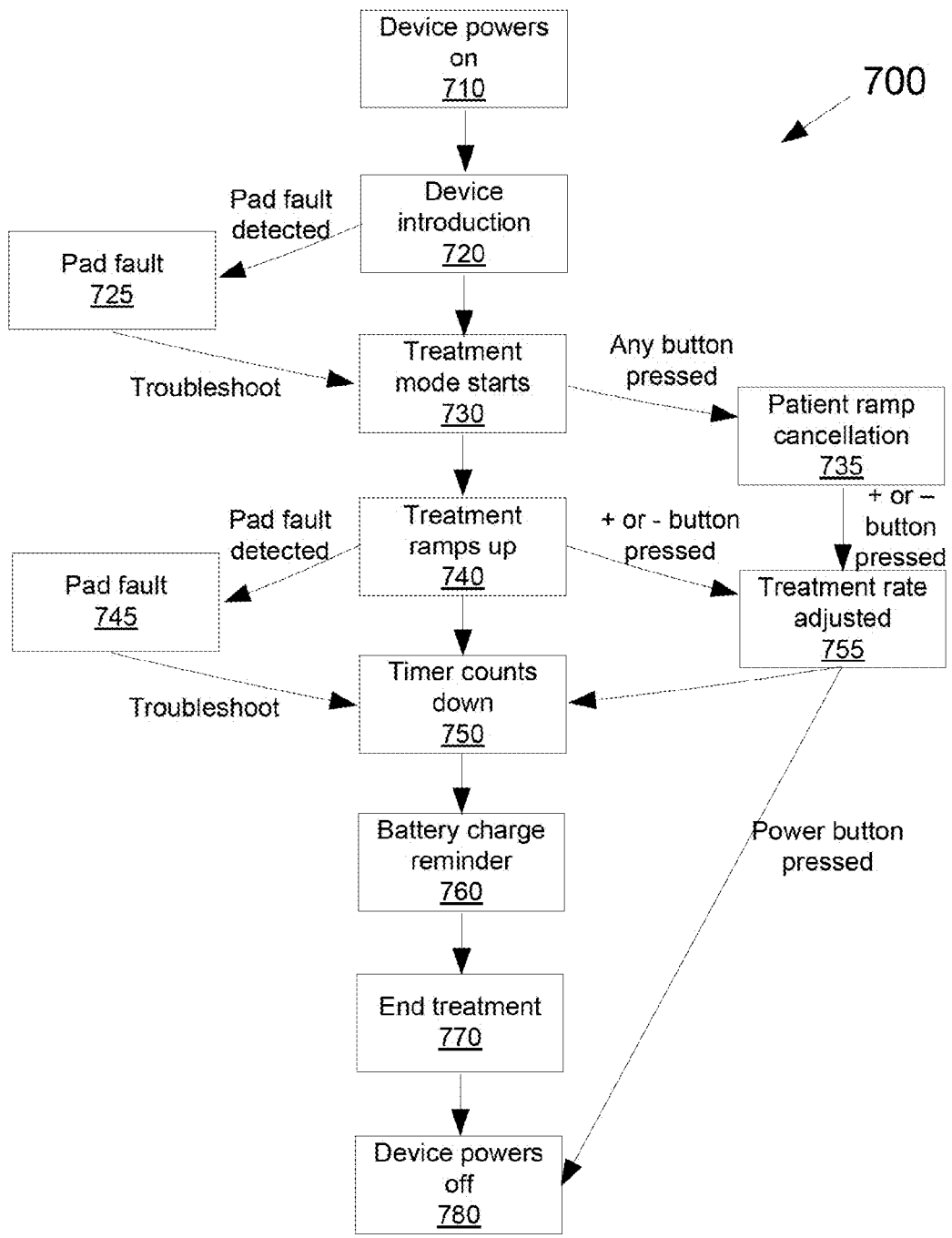
FIG. 7 shows a flow chart diagram illustrating the functions of the stimulation device of FIG. 1.

FIG. 7 is a flow chart diagram illustrating method 700 of using stimulation device 100. The device is powered up at step 710. In some embodiments, this may be done by holding power button 170 for a set duration of time. In some embodiments, this duration may be in the order of 3 seconds, for example. The device then moves to an introductory display at step 720. This may give the user visual, aural and/or tactile indication that the device has been powered on. For example, the buzzer 322 may be caused to emit a beeping noise, which may continue for a duration of around 1 second in some embodiments. Vibration motor 323 may be activated to cause the device to vibrate briefly. Furthermore or alternatively, the device may be caused to display a message. For example, the word "Hello" may be caused to be displayed and cycled on LCD 130 for a duration of around 4 seconds. LEDs 321 may illuminate. In some embodiments, LED 321*a* and LED 321*b* may illuminate, indicating that the device is powered on and that treatment is starting, respectively.

If a pad fault is detected by output monitor component 439, device 100 moves to step 725. Device 100 produces signals to indicate to the user that a fault has occurred. For example, pad fault indicator 138 may be illuminated, buzzer 322 may beep 3 times, and vibration motor 323 may cause a brief vibration. Treatment level display bar 132 and time remaining display 134 are turned off. These indicators prompt the user to troubleshoot, which may be by checking the connections and ensuring cable connectors 234 and 224 are properly plugged into connector inputs 160 and 165. Once the fault is rectified, device 100 progressed to step 730. If no pad fault was detected, device 100 moves directly from step 720 to 730.

At 730, treatment mode commences. This may be a normal treatment mode or a safety treatment or control lock mode, as set up using computing device 240 prior to the use of the device. In treatment mode, device 100 supplies stimulation signals to electrode connectors 226 and 236. Treatment level display bar 132 and time remaining display 134 are illuminating, showing a current treatment level, and the time remaining of the treatment period. The treatment level is the level of the current of the stimulation signals being delivered via electrode connectors 226 and 236. If the user presses any button, treatment ramp is cancelled at 735. Treatment level does not ramp up, but treatment continues at the current level. If the user does not press any buttons, device 100 progresses to step 740, and the treatment level steadily ramps up to a maximum level as set prior to use through computing device 240. In some embodiments, this ramp up may take a period of around 20 seconds, for example. Time remaining display 134 commences counting down the time of treatment remaining. In some embodiments, an initial treatment time of 1 hour may be set, and display 134 may count down each minute until 0 minutes are remaining.

If a pad fault is detected by output monitor component 439, device 100 moves to step 745. Device 100 produces signals to indicate to the user that a fault has occurred. For example, pad fault indicator 138 may be illuminated, buzzer 322 may beep 3 times, and vibration motor 323 may cause a brief vibration. Treatment level display bar 132 and time remaining display 134 are turned off. These indicators prompt the user to troubleshoot, which may be by checking the connections and ensuring cable connectors 234 and 224 are properly plugged into connector inputs 160 and 165. Once the fault is rectified, device 100 may progress to step 750. If no pad fault was detected, device 100 may move directly from step 740 to 750.

If the user presses the treatment level decrease button 180 or the treatment level increase button 185 from either step 735 or 740, device 100 enters step 755 and the treatment level is adjusted up or down depending on the button pressed. In some embodiments, the treatment level is adjusted by 1 level increment each time one of the buttons 180 or 185 are pressed. Some embodiments may have around 40 levels, with a maximum current of around 30 mA into a 1 kΩ load. Each level increment corresponds to about 0.75 or 1 mA for a body having 1 kΩ impedance, so while the change in stimulation intensity is intended to be about 0.75 or 1 mA for each level, it will in practice vary from that amount, depending on the patient receiving the stimulation. In some embodiments, where the device is in a control lock mode (which may be termed a safety mode), the treatment level may increase or decrease a maximum of three levels from the start level (i.e. resulting in a maximum intensity variation from the start level of around 2 mA to 3 mA). Each time a button 180 or 185 is pressed, the user may receive feedback that the button press was registered by device 100. For example, treatment level display bar 132 may display the new treatment level, and time remaining display 134 may be used to display a numeric treatment level for a period, which may be in the order of 2 seconds in some embodiments. Where device 100 is in safety mode or control lock mode, device 100 may give the user a visual, aural or tactile indication of when the maximum treatment level has been reached. For example, buzzer 322 may emit a short beep, and vibration motor 323 may cause device 100 to vibrate briefly. After a period of no buttons being pressed, which may be a period of 5 seconds, for example, device 100 moves from step 755 to 750. Alternatively, if the user holds power button 170 for a period, which may be a period of 3 seconds in some embodiments, device 100 may move to step 780 and power off.

From step 750, the treatment continues at the level reached during ramp up or set by the user, and the treatment time continues to count down. At step 760, when the treatment time is nearing to 0, such as when it reaches 1 minute, battery indicator 137 may flash to remind the user to charge the device. When the countdown reaches 0, at step 770, treatment ends. This may be indicated to the user in a number of ways. For example, buzzer 322 may emit 1 long beep, corresponding to vibration motor 323 vibrating for one long period. In some other embodiments, buzzer 322 may emit 2 short beeps and 1 long beep, corresponding to vibration motor 323 vibrating for 2 short periods followed by one longer period. Time remaining display 134 may be used to display a message to the user, which may be the word "End" in some embodiments. The device may stay switched on for a period of time, which may be 3 minutes in some embodiments, before automatically switching off. Alternatively, the user may be able to power off the device by holding power button 170 for a period of time, such as a period of 3 seconds, for example.

Figure 8:
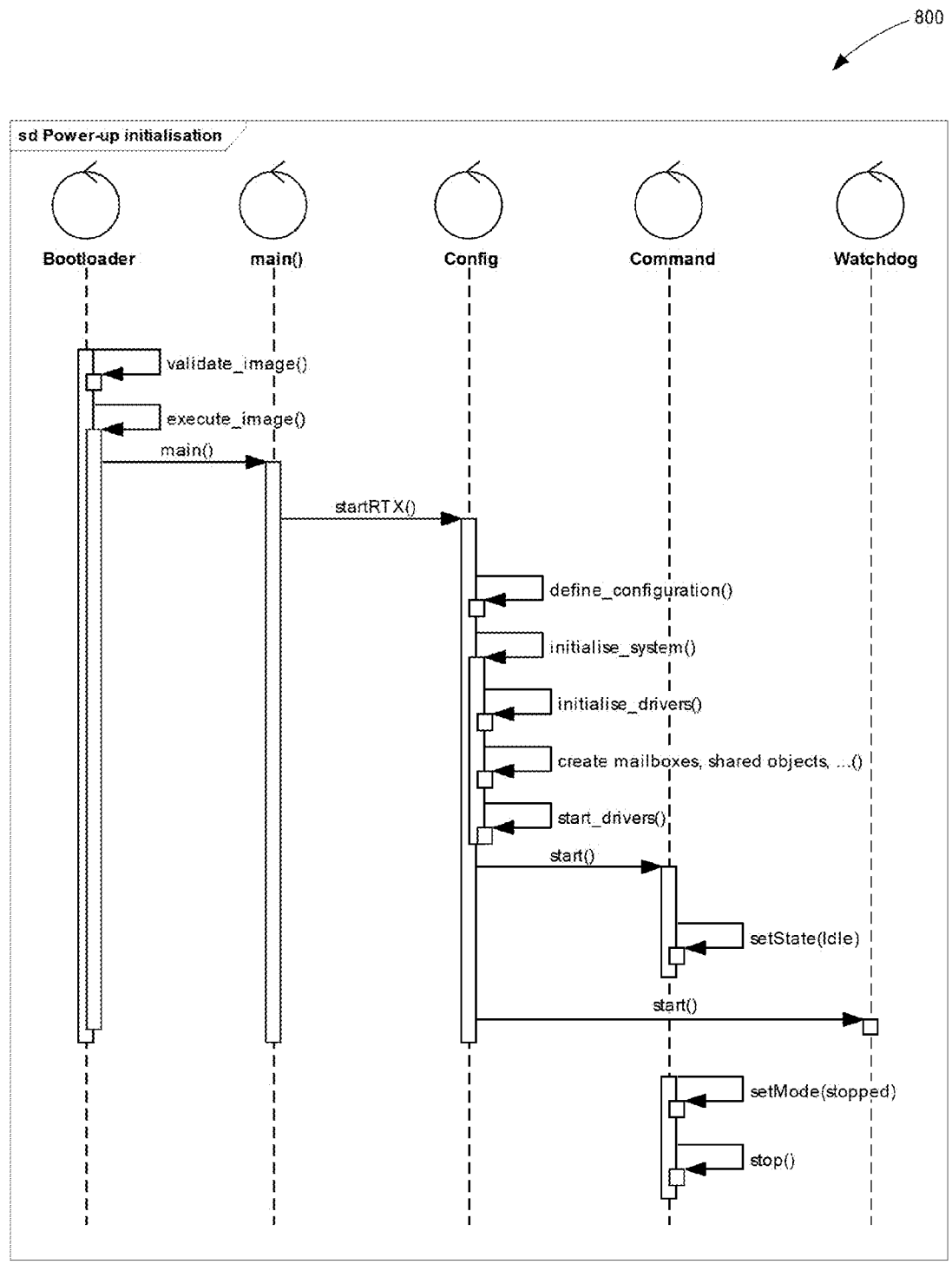
FIG. 8 is a sequence diagram of a power-up initialisation sequence for the firmware of the device of FIG. 1.

FIG. 8 is a sequence diagram of a power-up initialisation sequence 800 for device firmware 400. This sequence may be run when device firmware 400 is initialised. As device 100 is normally powered by its internal rechargeable battery 330 (even when it appears to be "switched off"), this sequence seldom takes place. It may occurs when either power is first applied to device 100 during manufacturing, external power is connected after battery 330 has run flat, firmware 400 is recovering following a serious failure (e.g. watchdog expiry); or firmware 400 is restarted on command (e.g. after loading a new firmware image).

Figure 9:
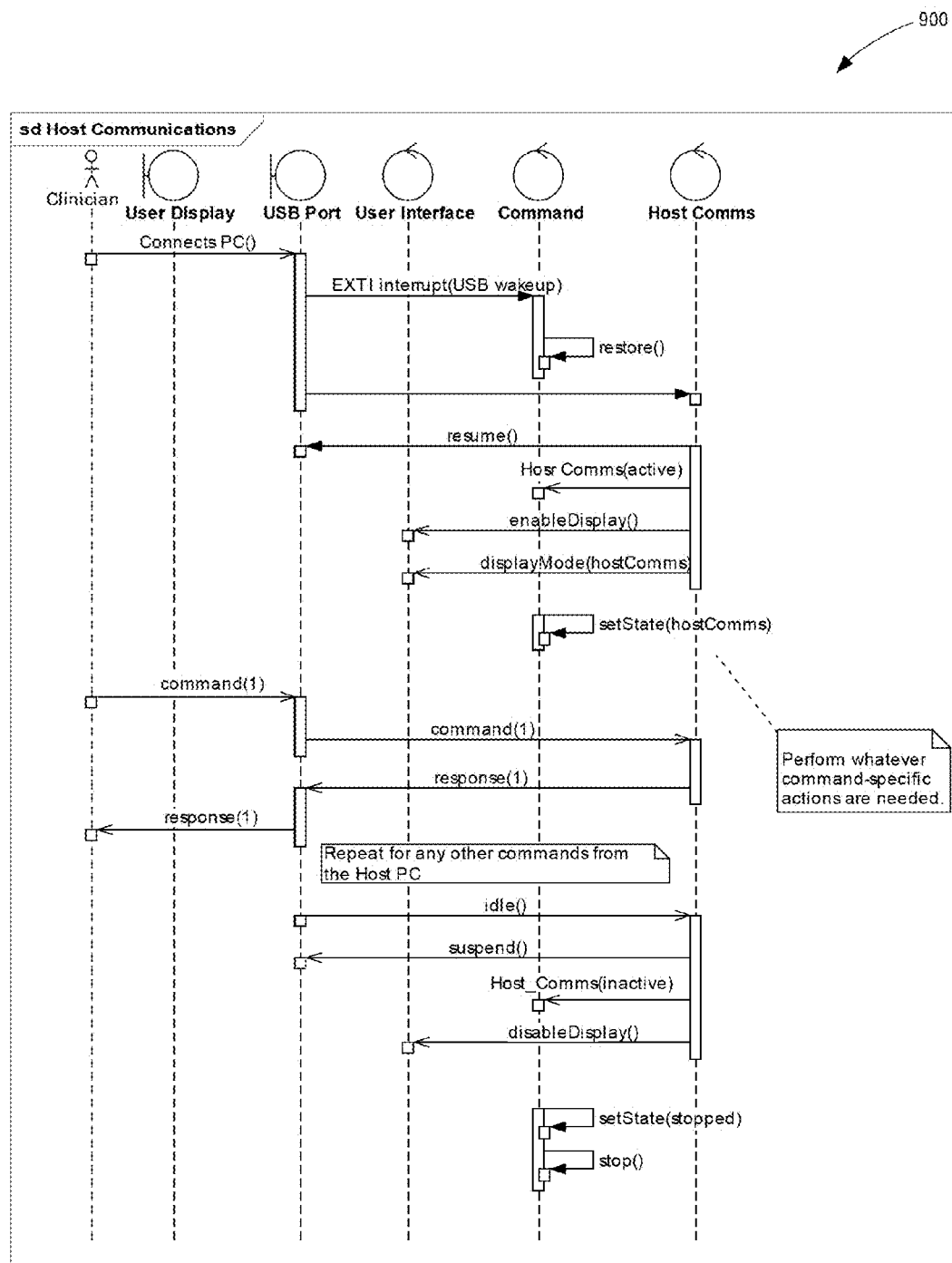
FIG. 9 is a sequence diagram of a host communication mode sequence for the firmware of the device of FIG. 1.

FIG. 9 is a sequence diagram of the host communication mode sequence 900 for device firmware 400. Host communications mode 900 may be used by clinicians to set the operating parameters for subsequent treatments. Host communications mode 900 may be entered by connecting device 100 to computing device 240 using USB cable 250. As soon as the communications link becomes active, device 100 will wake-up or stop its current activity and enter host communications mode 900.

Figure 10A:
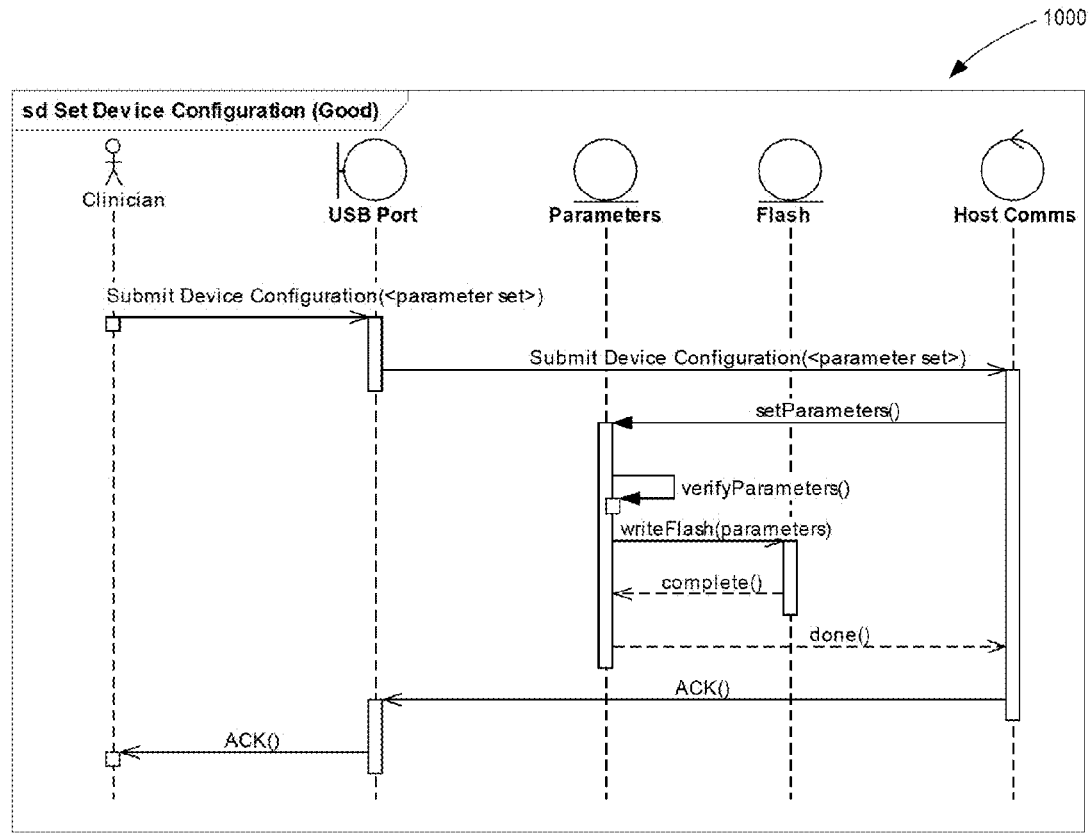
FIGS. 10a and 10b are sequence diagrams of a set device configuration sequence for the firmware of the device of FIG. 1.
Figure 10B:
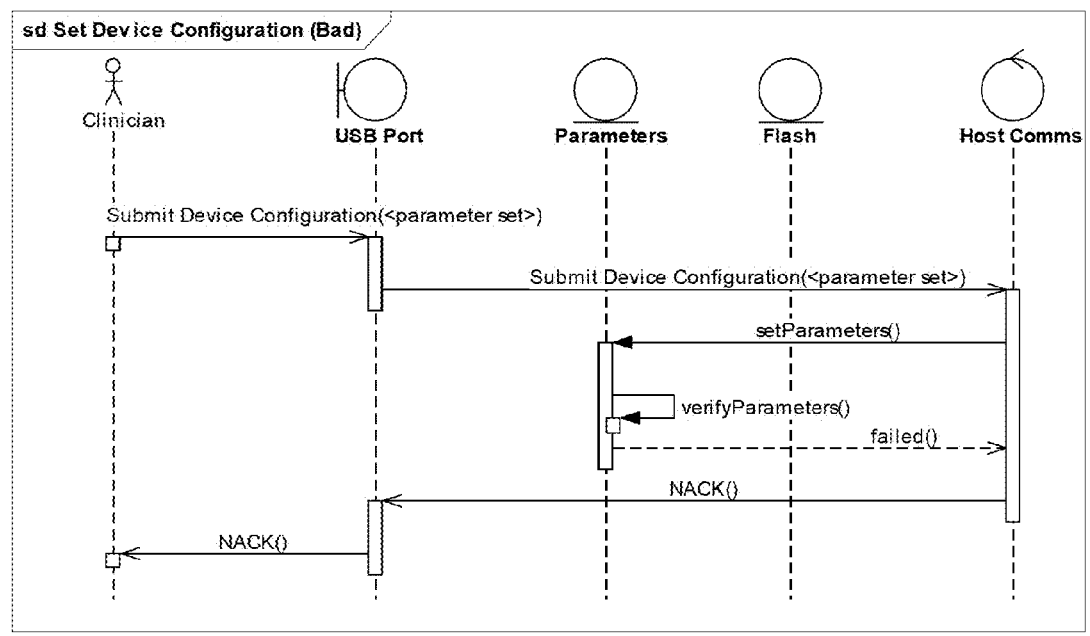

FIGS. 10a and 10b are sequence diagrams of the set device configuration sequences 1000 and 1050 for device firmware 400. Computing device 240 may write the entire configuration in a single transaction. Device 100 may accept this configuration as shown in FIG. 10a, or reject this configuration in its entirety as shown in FIG. 10b.

Figure 11:
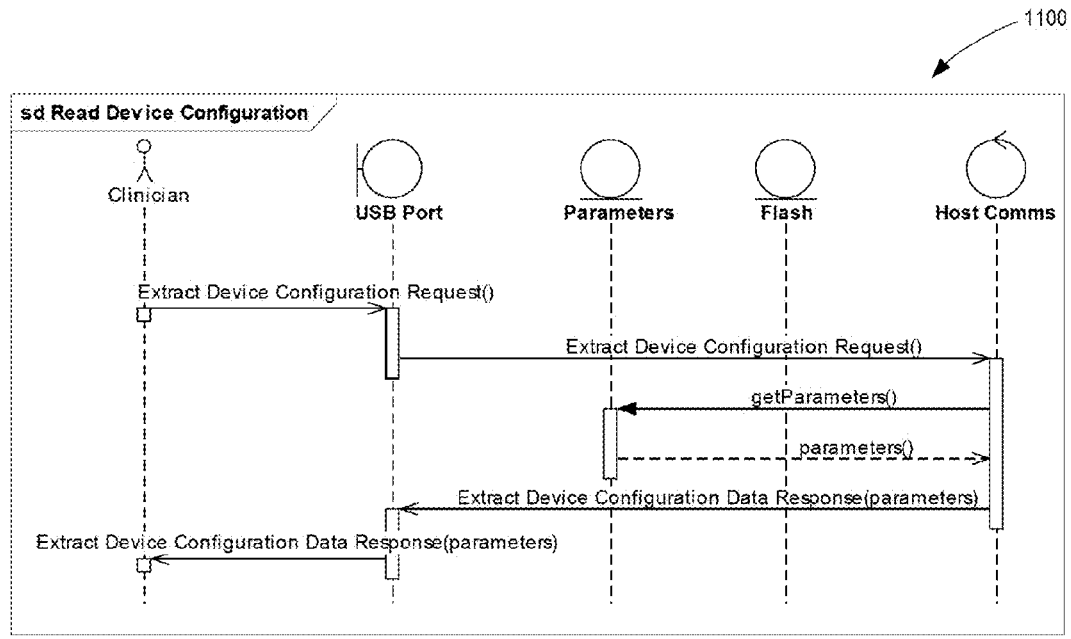
FIG. 11 is a sequence diagram of a read device configuration sequence for the firmware of the device of FIG. 1.

FIG. 11 is a sequence diagram of the read device configuration sequence 1100 for device firmware 400. Computing device 240 reads all configuration information from device 100 in a single transaction. In some embodiments, the active parameter values are held in RAM, so no Flash accesses are needed.

Figure 12:
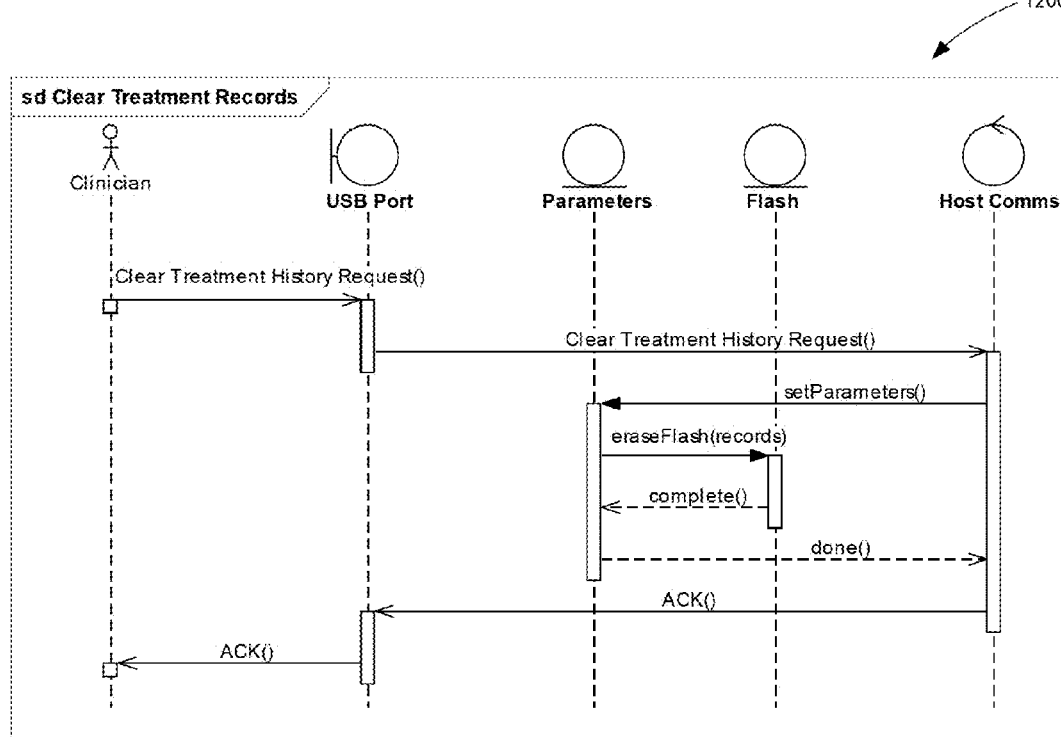
FIG. 12 is a sequence diagram of a clear treatment records sequence for the firmware of the device of FIG. 1.

FIG. 12 is a sequence diagram of the clear treatment records sequence 1200 for device firmware 400. Computing device 240 may have a single command to erase all treatment records. In some embodiments, partial erasure may not be supported.

Figure 13:
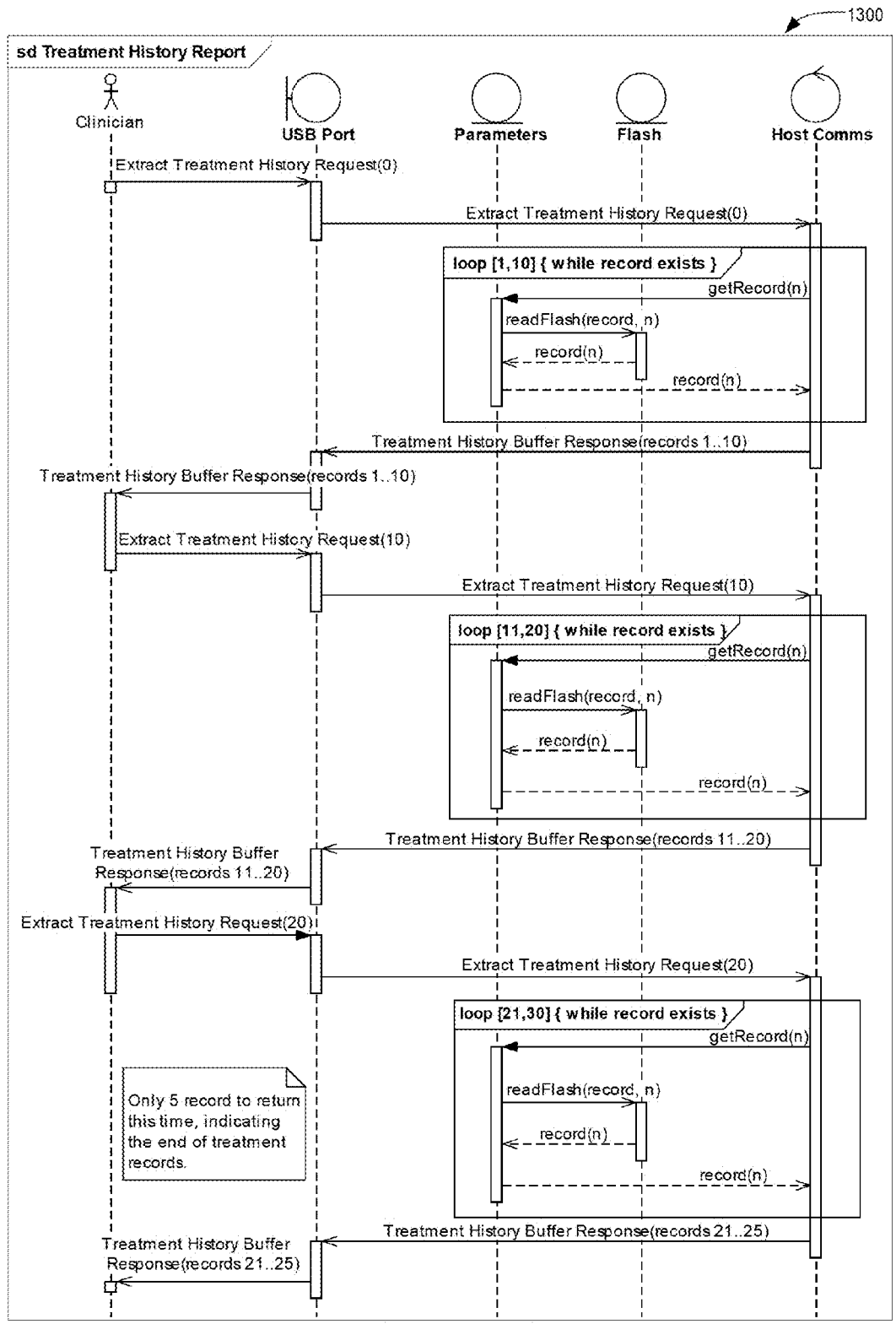
FIG. 13 is a sequence diagram of a treatment reporting sequence for the firmware of the device of FIG. 1.

FIG. 13 is a sequence diagram of the treatment reporting sequence 1300 for device firmware 400. Treatment reports may be built up within device 100 during treatment and may be over-written when memory runs out, or they may be deleted on command. A clinician may be able to read the treatment reports from device 100 using computing device 240 via the USB communications interface.

Figure 14:
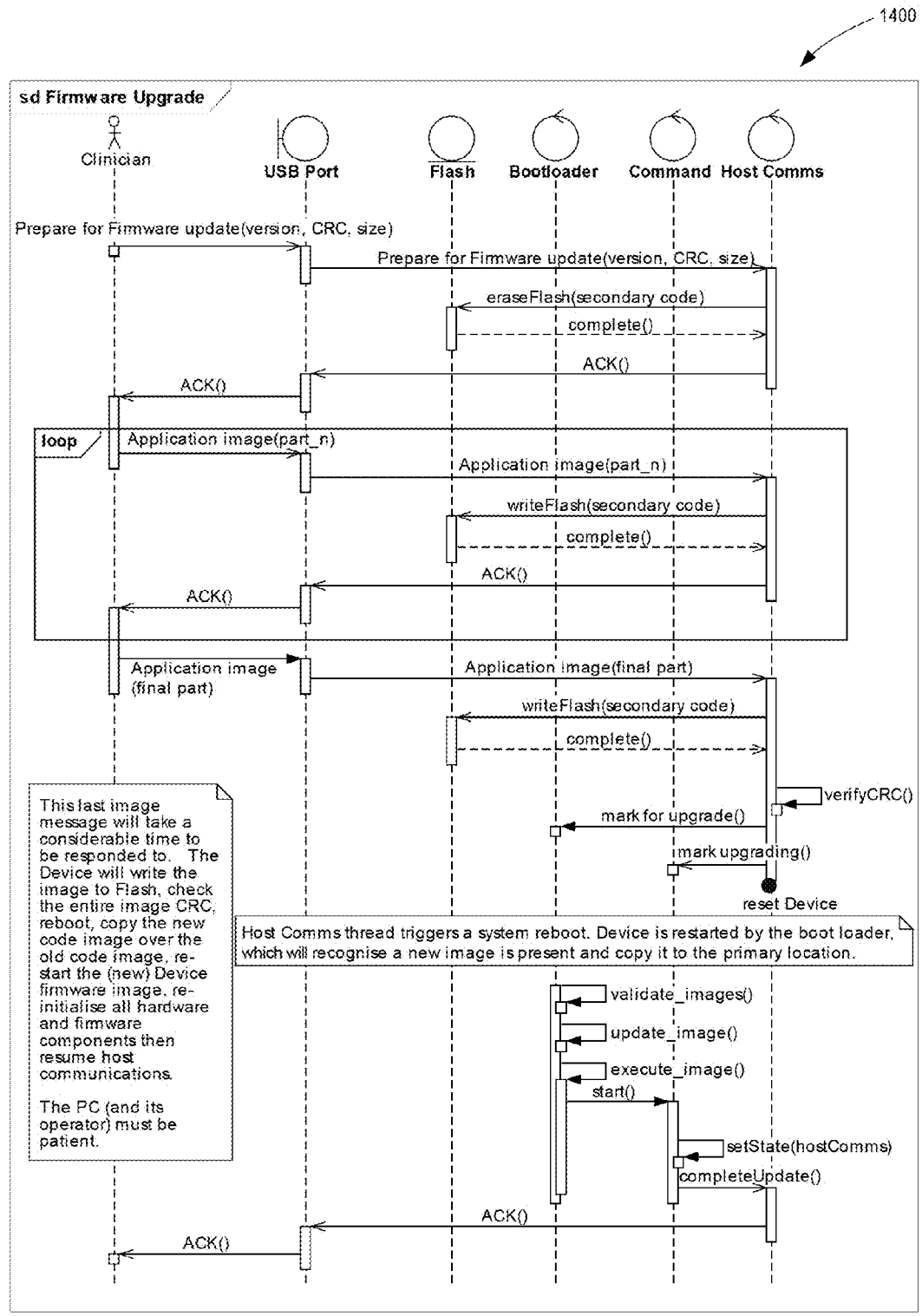
FIG. 14 is a sequence diagram of a firmware upgrade sequence for the firmware of the device of FIG. 1.

FIG. 14 is a sequence diagram of the firmware upgrade sequence 1400 for device firmware 400. Device 100 may allow computing device 240 to send it a new firmware image.

Figure 15:
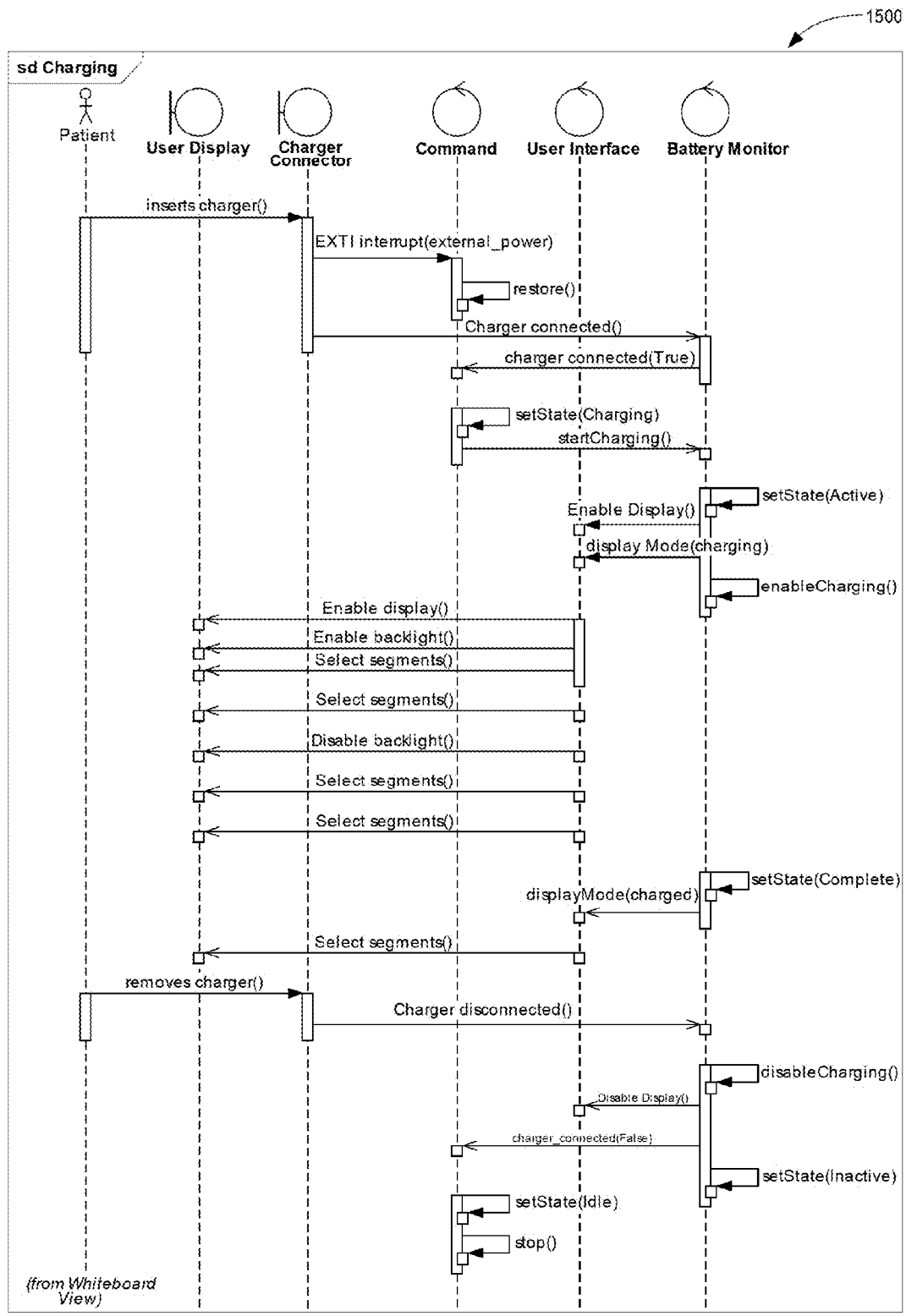
FIG. 15 is a sequence diagram of a charging sequence for the firmware of the device of FIG. 1.

FIG. 15 is a sequence diagram of the charging sequence 1500 for device firmware 400. When the user connects an AC/DC plug pack 260 to device 100 while it is not doing anything, device 100 may wake-up and start charging.

Figure 16:
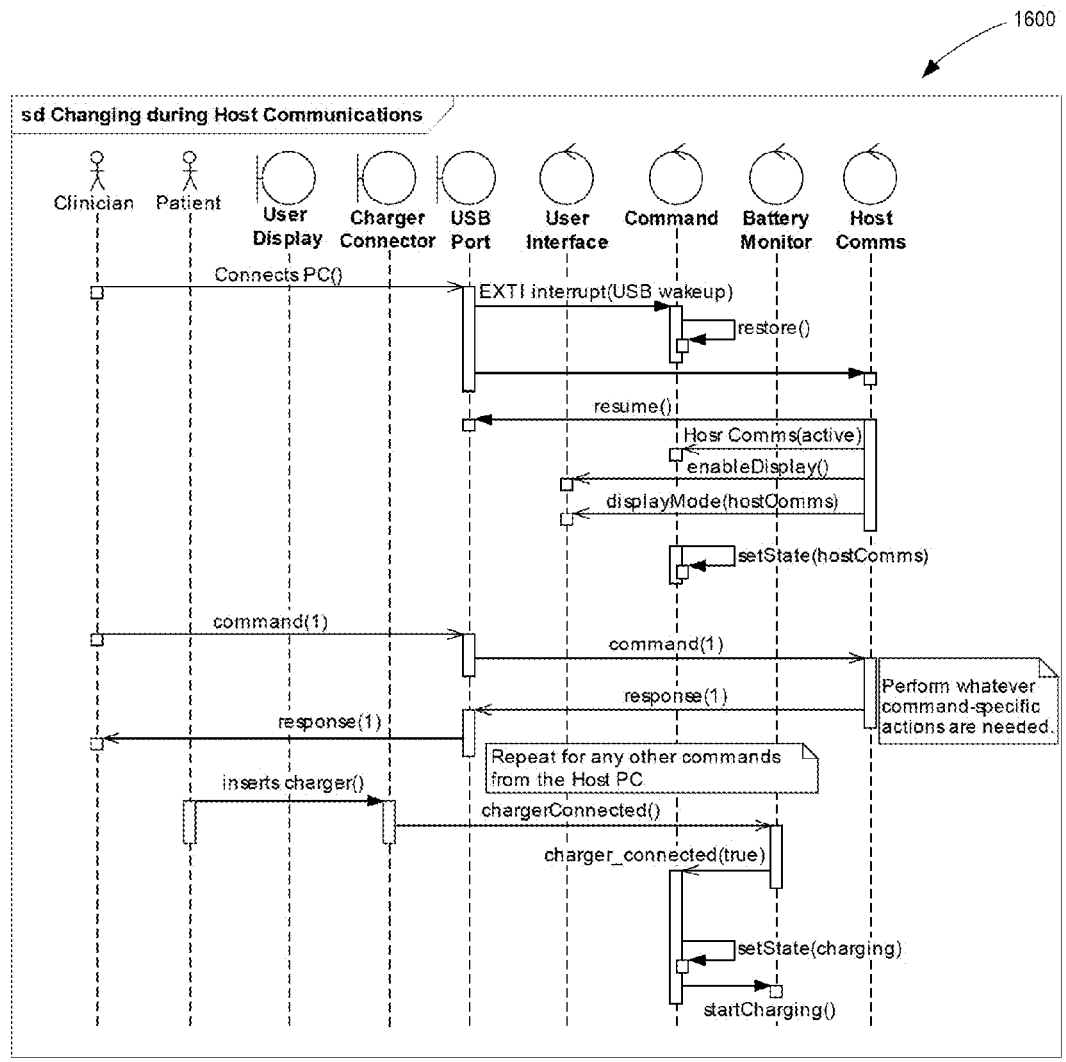
FIG. 16 is a sequence diagram of a charging in host communications mode sequence for the firmware of the device of FIG. 1.

FIG. 16 is a sequence diagram of the charging in host communications mode sequence 1600 for device firmware 400. If AC/DC plug pack 260 is connected during host communications, host communications may be terminated.

Figure 17:
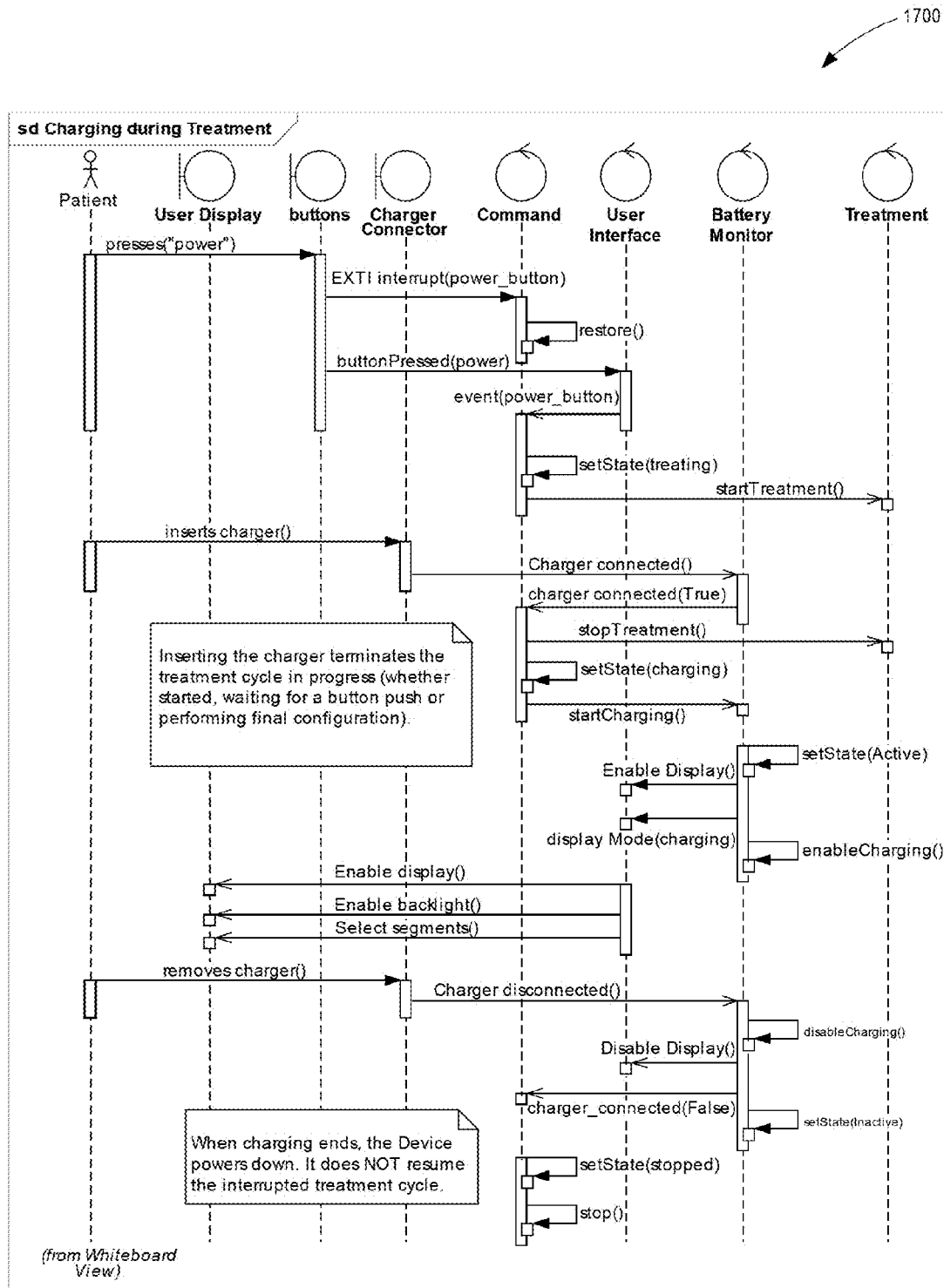
FIG. 17 is a sequence diagram of a charging during treatment sequence for the firmware of the device of FIG. 1.

FIG. 17 is a sequence diagram of the charging during treatment sequence 1700 for device firmware 400. If charging is started during treatment, treatment stops. When charging completes, device 100 becomes idle; it does not automatically restart the interrupted treatment cycle.

Figure 18:
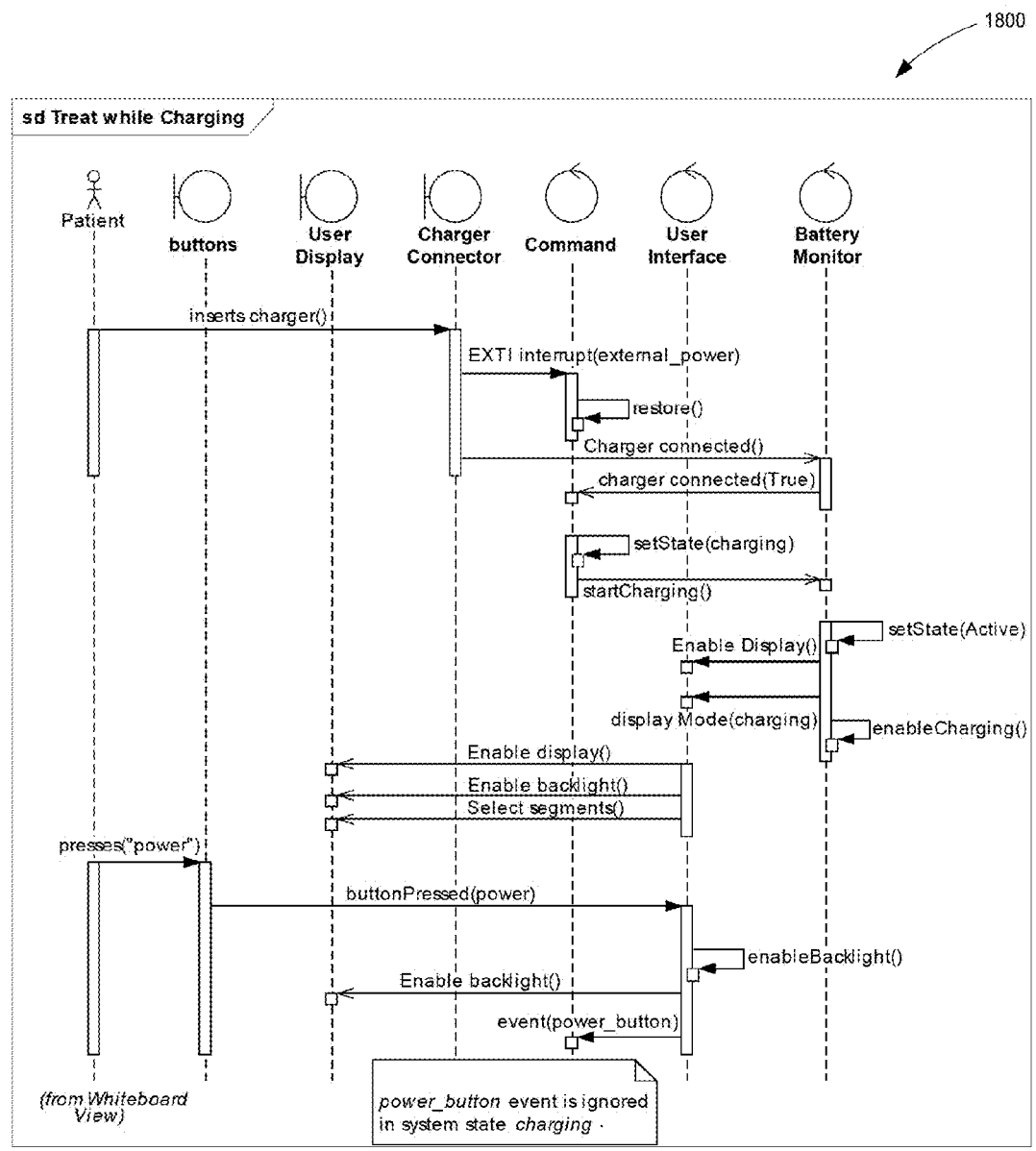
FIG. 18 is a sequence diagram of a treatment sequence while charging for the firmware of the device of FIG. 1.

FIG. 18 is a sequence diagram of the treatment while charging sequence 1800 for device firmware 400. If device 100 is busy charging when the user presses power button 170, device 100 will continue with its current operation. The only change the user will observe is that LCD display 130 will illuminate for a period of time.

Figure 19:
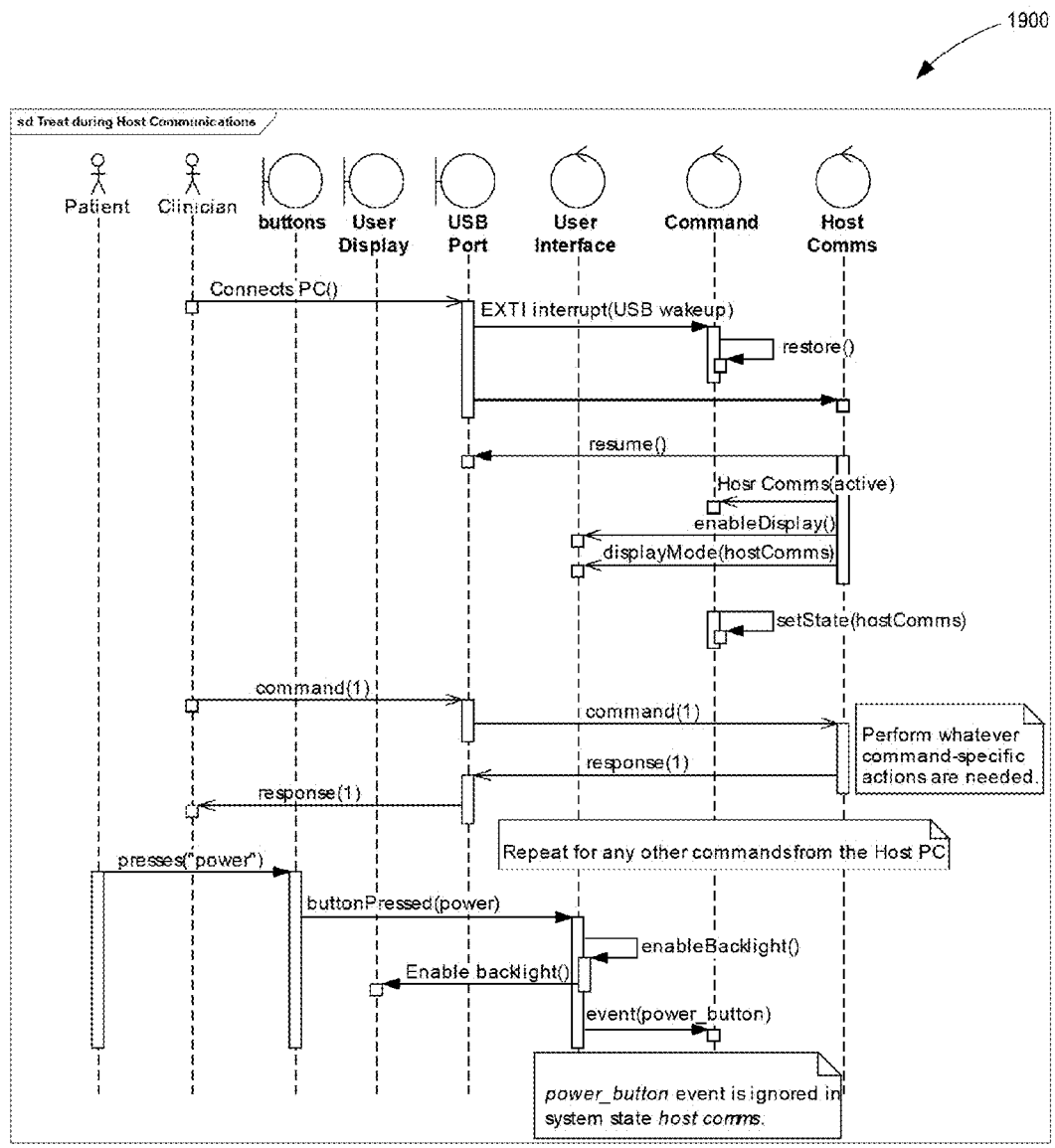
FIG. 19 is a sequence diagram of a treatment sequence during host communications for the firmware of the device of FIG. 1.

FIG. 19 is a sequence diagram of the treatment during host communications sequence 1900 for device firmware 400. If device 100 is busy talking to computing device 240 when the user presses power button 170, device 100 will continue with its current operation. The only change the user will observe is that LCD display 130 will illuminate for a period of time.

Figure 20:
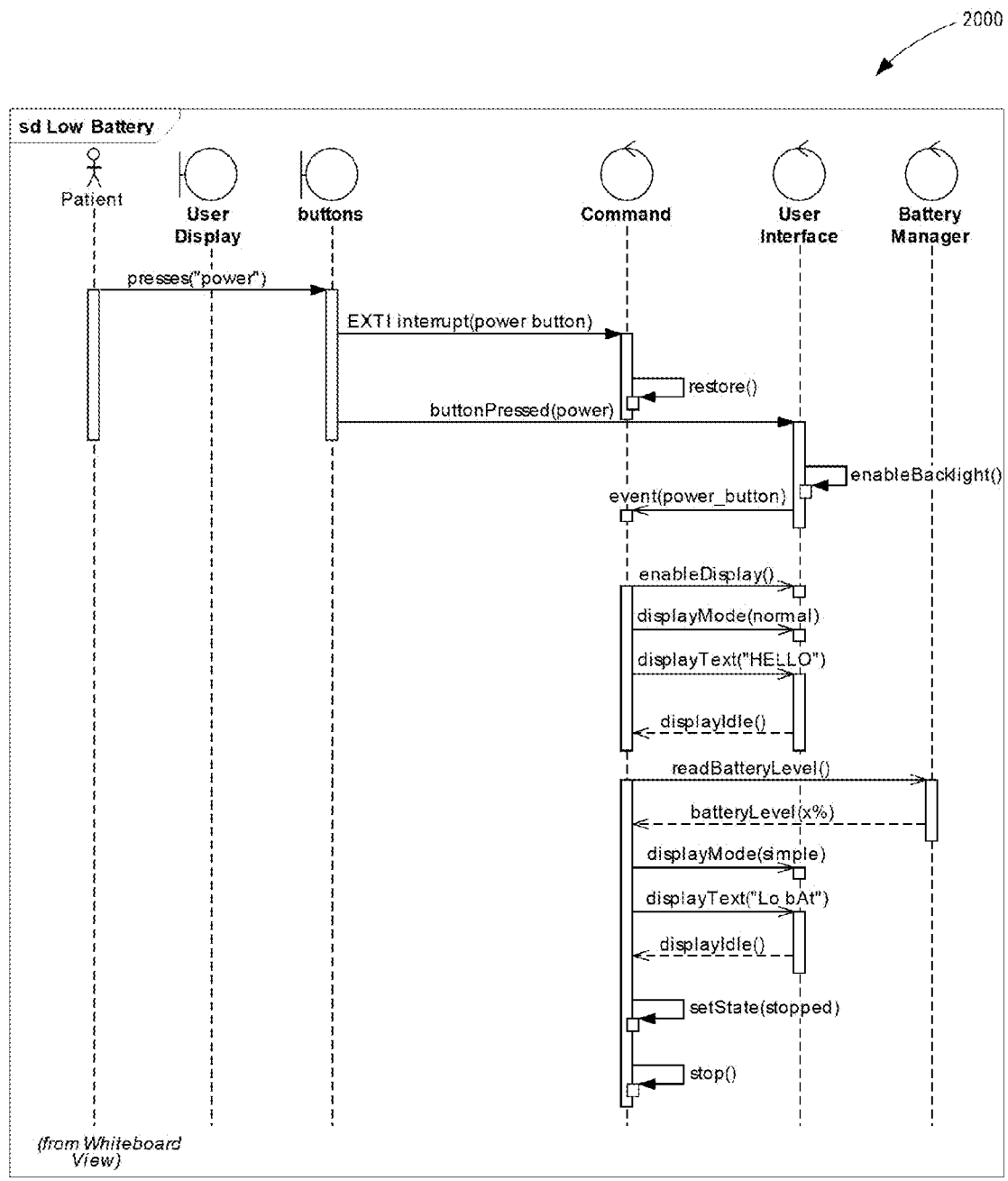
FIG. 20 is a sequence diagram of a low battery sequence for the firmware of the device of FIG. 1.

FIG. 20 is a sequence diagram of the low battery sequence 2000 for device firmware 400. If the user switches device 100 on while battery 330 has a low charge level, LCD display 130 will show a low battery warning message for a period of time and then turn off.

Figure 21:
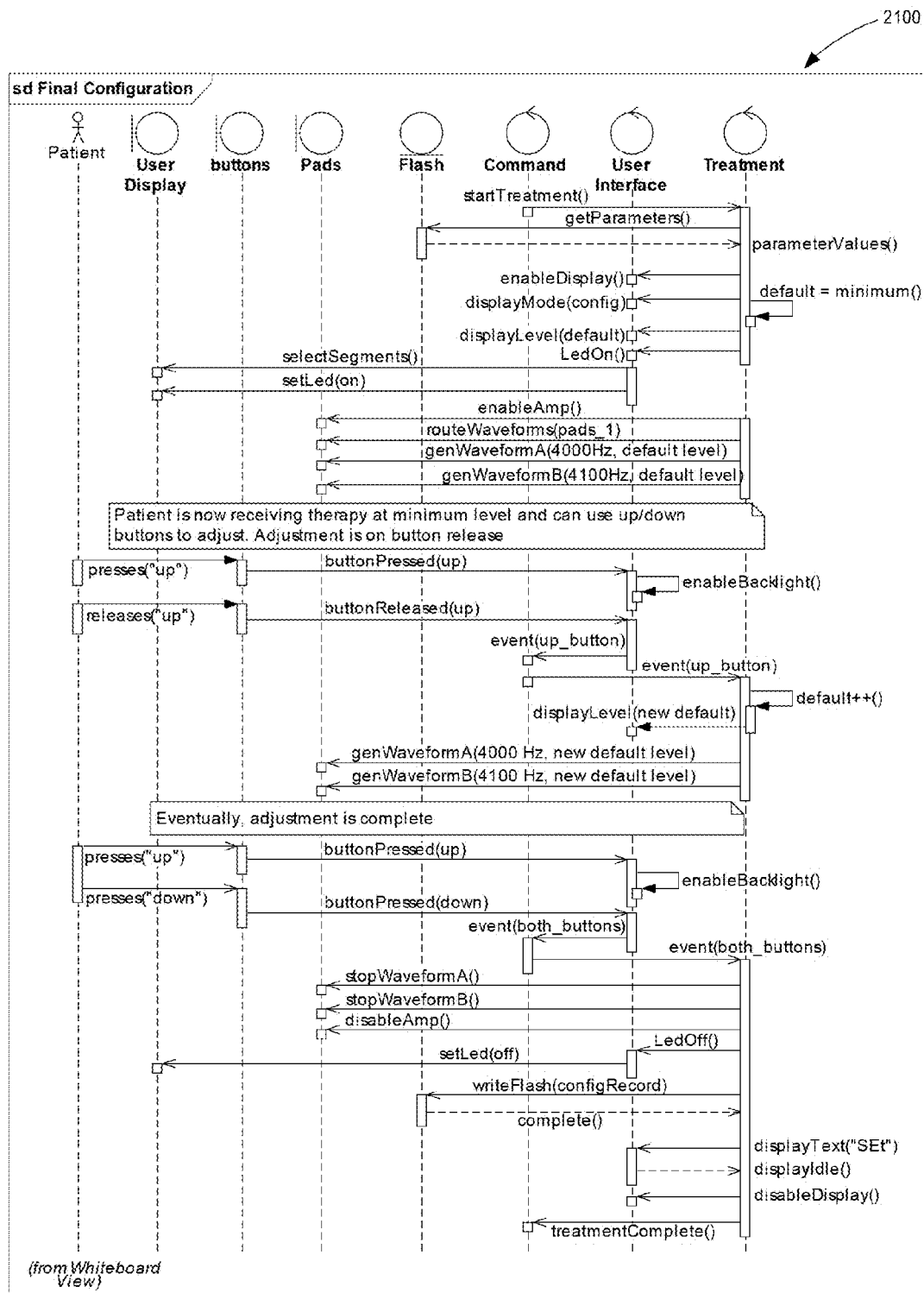
FIG. 21 is a sequence diagram of a final configuration sequence for the firmware of the device of FIG. 1.

FIG. 21 is a sequence diagram of the final configuration sequence 2100 for device firmware 400. The final part of configuration is to tune the default power level to suit the patient. If this hasn't been done by the clinician, it will occur when device 100 is switched on by the user (in the presence of a nurse). When device 100 is switched on by the user, device 100 checks if final configuration is required; if so, device 100 enters a final configuration state. In this state, continuous stimulation is provided to the patient, starting at minimum power level. The user can increase or decrease this value (within clinician set limits) using treatment level decrease button 180 and treatment level increase button 185 until the preferred level is found. The user then presses and holds both the treatment level decrease button 180 and treatment level increase button 185 for a few seconds to signify selection has been made. The default power level will then be saved, a "Set" message will be displayed on LCD 130 for a period of time and then LCD 130 will switch off.

Figure 22:
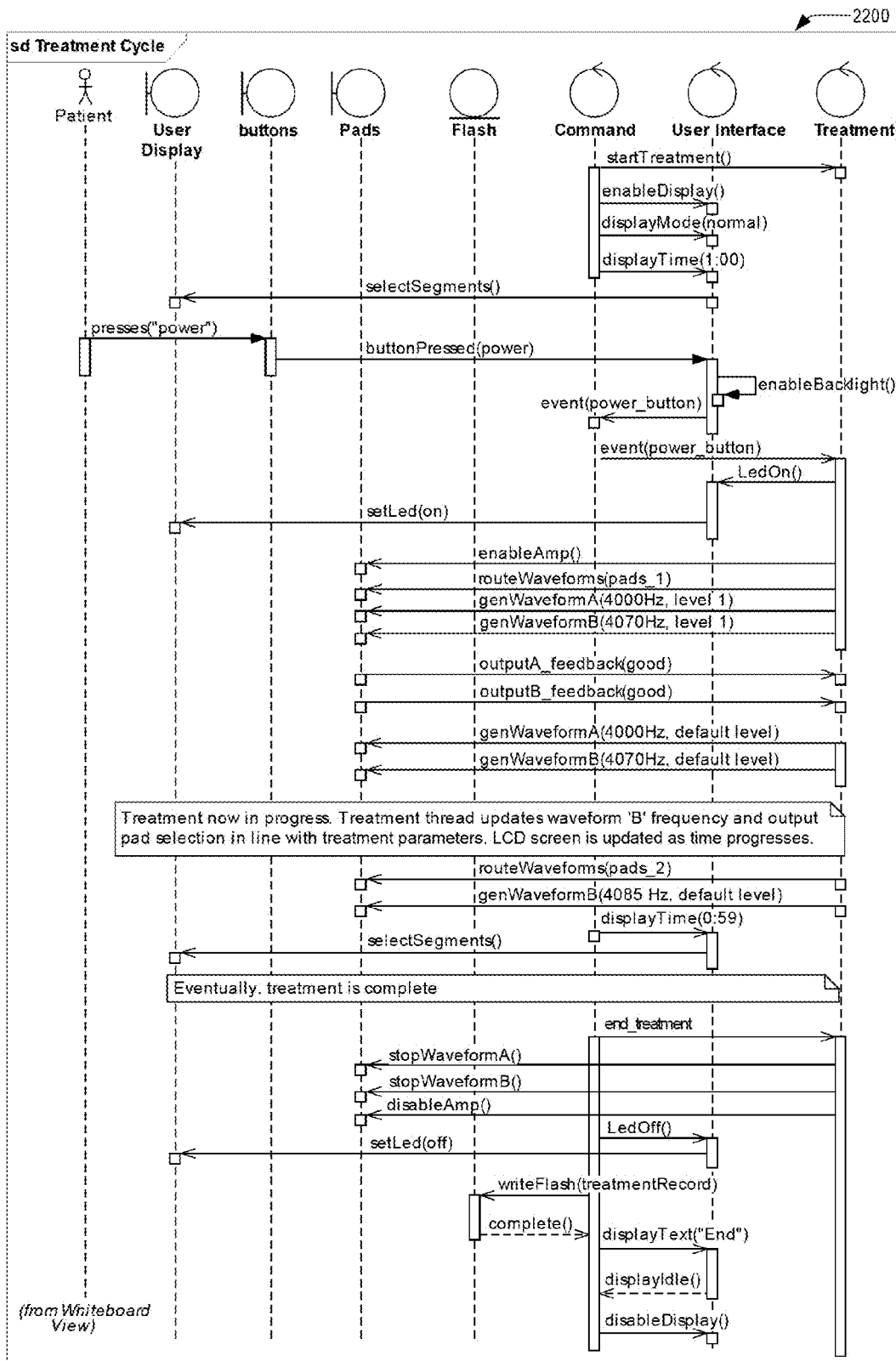
FIG. 22 is a sequence diagram of treatment cycle sequence for the firmware of the device of FIG. 1.

FIG. 22 is a sequence diagram of the treatment cycle sequence 2200 for device firmware 400. A treatment cycle is started by the user pressing power button 170 while device 100 is switched on, or pressing power button 170 twice when device 100 is in idle mode 640. A treatment cycle may only take place if a series of pre-conditions are met. Some of these pre-conditions may include: having sufficient power to complete the treatment cycle; having either enough time passed after the last cycle or some treatment remaining from the last cycle; and the pads being correctly positioned and connected to device 100.

Figure 23:
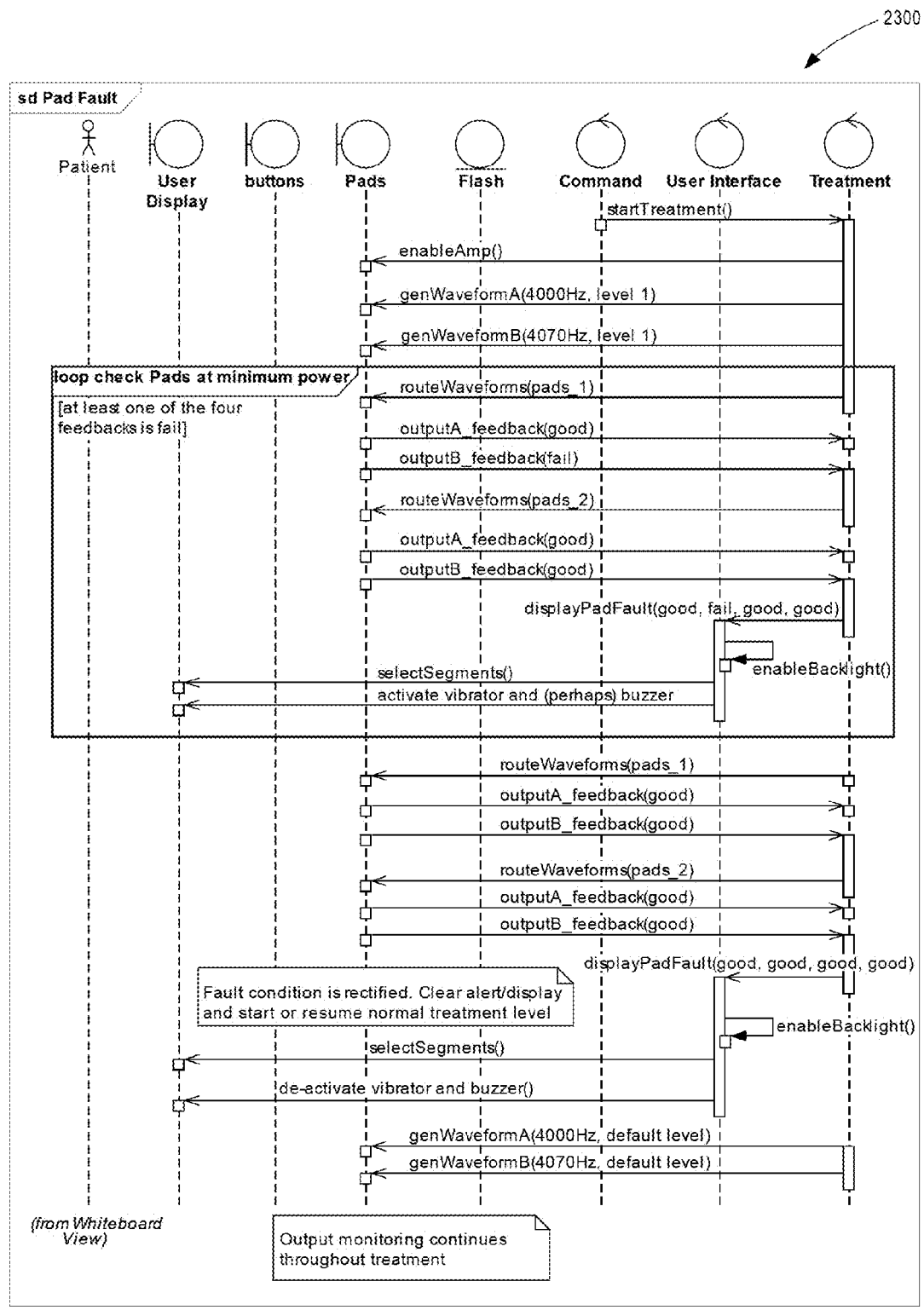
FIG. 23 is a sequence diagram of pad fault detection sequence for the firmware of the device of FIG. 1.

FIG. 23 is a sequence diagram of the pad fault detection sequence 2300 for device firmware 400. While therapy is being delivered (both actual treatment and final configuration), device 100 continuously monitors the output feedback signals to ensure there are no pad connection issues. If there are, the user is alerted and treatment is provided at minimum level (to allow pad testing) until proper connections are established. A pad fault may be detected by monitoring an RMS voltage based on the current on the primary side of the output transformers. When the measured voltage comes into a pre-determined range indicating that the impedance at the electrodes is near open-circuit (this may be around 2 kΩ, for example), a pad fault is detected. The pre-determined voltage range may be configured through firmware, and may vary depending on the treatment level being administered.

Figure 24:
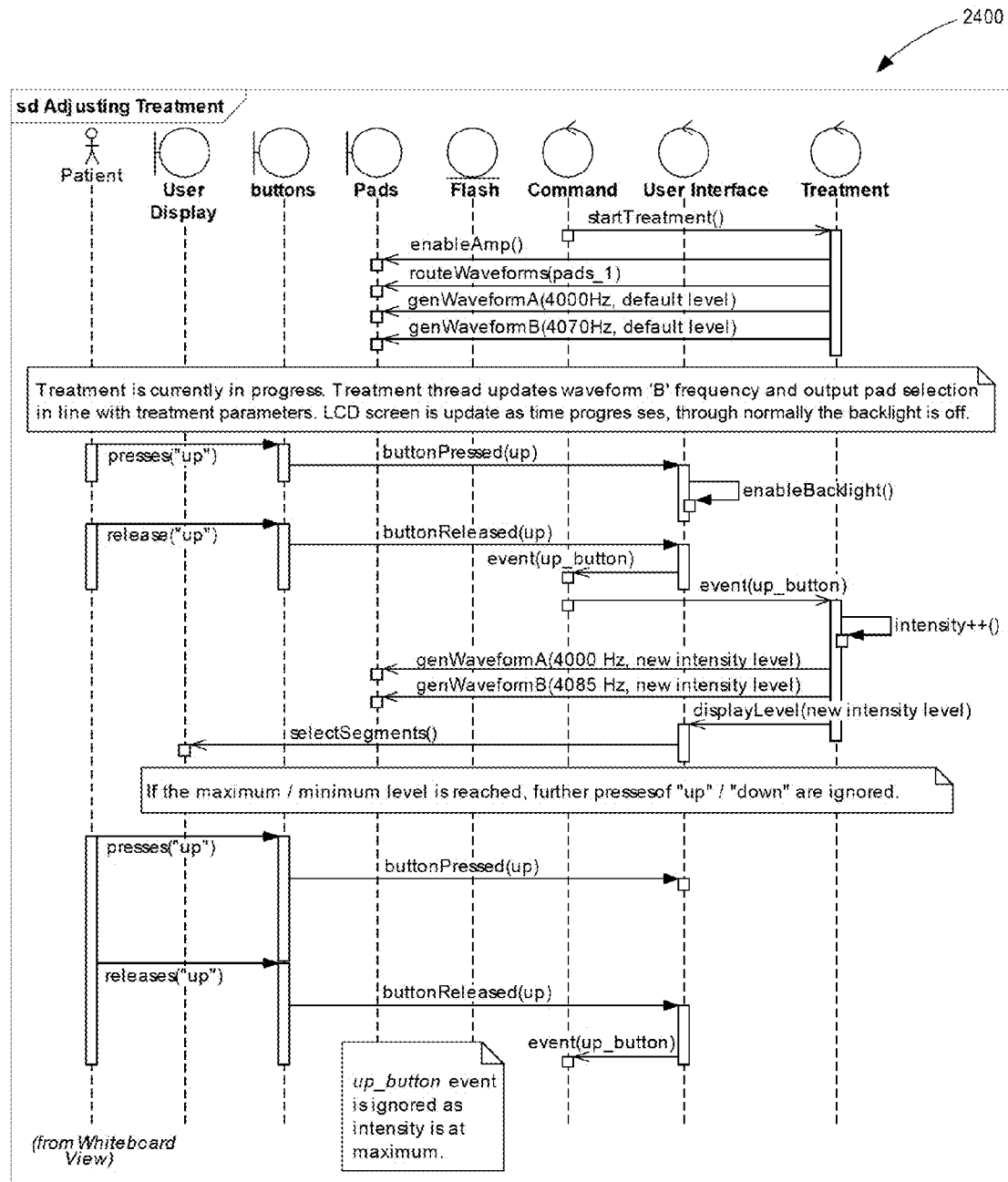
FIG. 24 is a sequence diagram of adjustment during treatment sequence for the firmware of the device of FIG. 1.

FIG. 24 is a sequence diagram of the adjustment during treatment sequence 2400 for device firmware 400. During a treatment cycle, the patient can adjust the intensity of treatment, within clinician set limits, using treatment level decrease button 180 and treatment level increase button 185; intensity is increased or decreased by one quantum each time one of these two buttons is released. If the appropriate limit is reached, further button operations in that direction are ignored.

Figure 25:
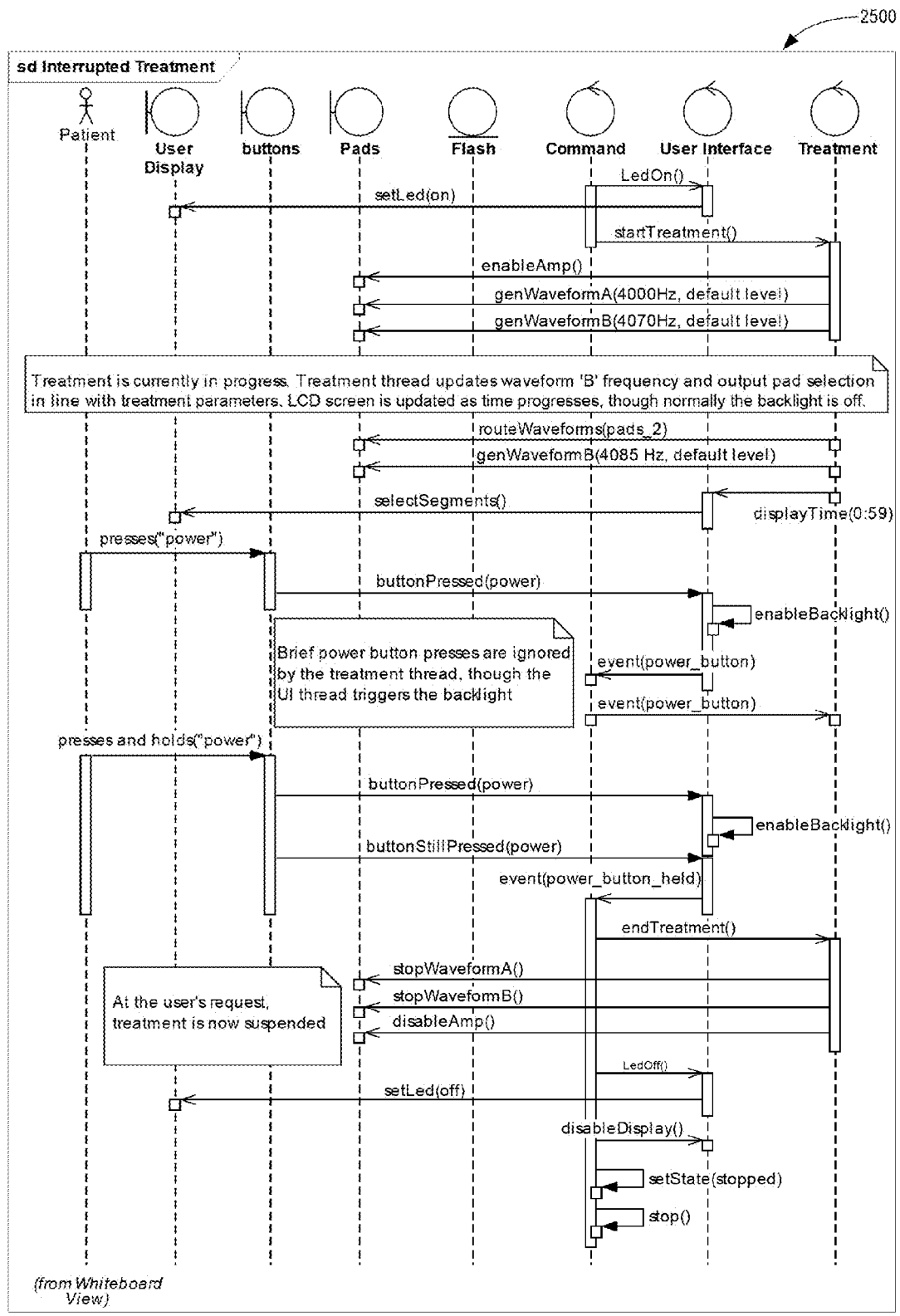
FIG. 25 is a sequence diagram of interrupted treatment sequence for the firmware of the device of FIG. 1.

FIG. 25 is a sequence diagram of the interrupted treatment sequence 2500 for device firmware 400. The patient can suspend a therapy session by turning device 100 off mid cycle; this may be achieved by holding power button 170 for a long period of time, which may be a period in the order of 3 seconds in some embodiments. This may cause device 100 to immediately power off. In some embodiments this does not trigger any alert for the patient, as patient request initiated the event. Interrupted treatments are either abandoned by firmware 400 after a period of time, which may be in the order of 12 hours from the original start of treatment in some embodiments, or are continued by the patient requesting a treatment cycle. Device 100 may be configured such that the initial "time remaining" display shows the remaining time instead of the whole treatment period.

Figure 26:
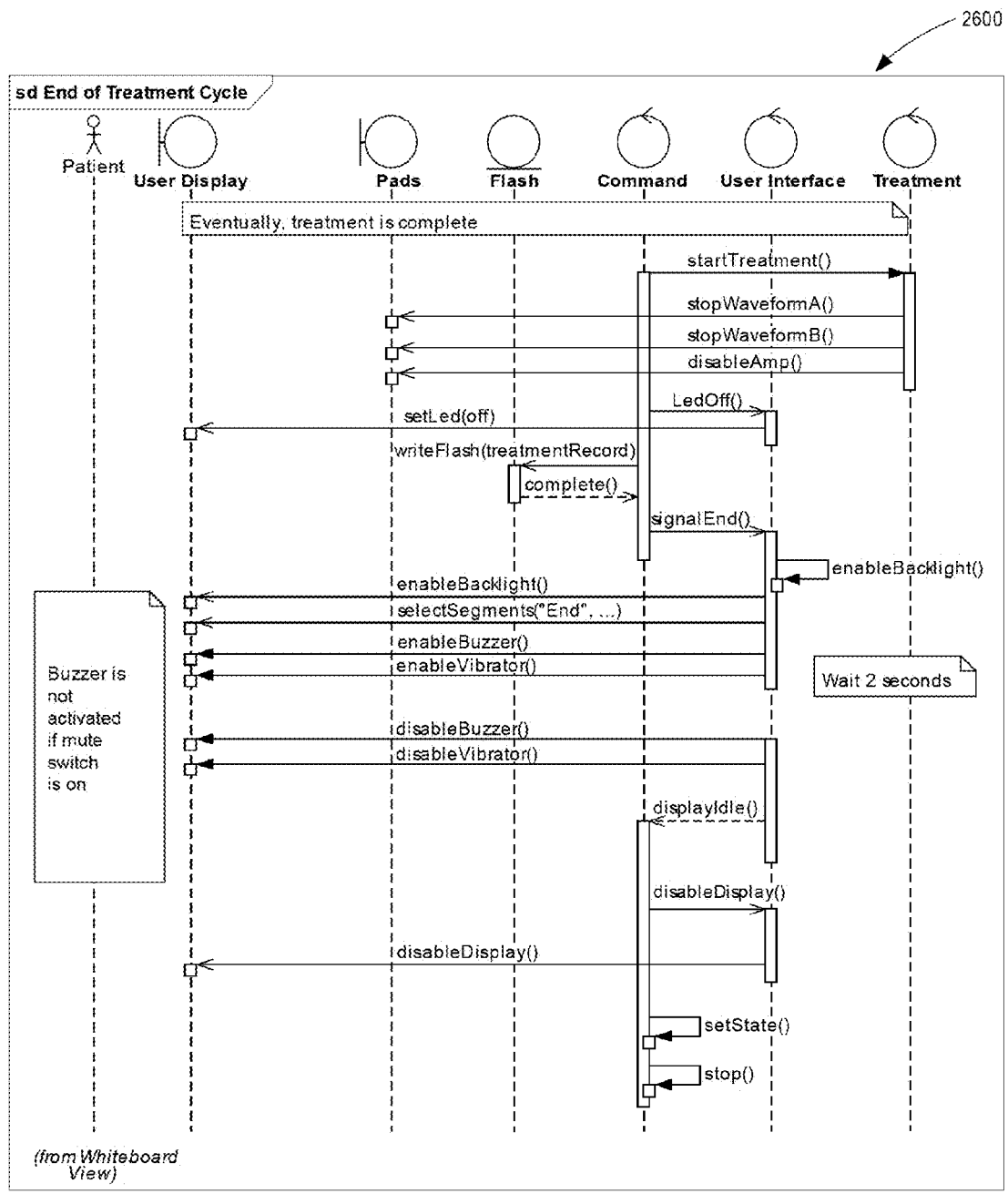
FIG. 26 is a sequence diagram of end of treatment indication sequence for the firmware of the device of FIG. 1.

FIG. 26 is a sequence diagram of the end of treatment indication sequence 2600 for device firmware 400. At the end of a treatment cycle, therapy ceases, a report of any treatment which has accumulated in RAM may be written to Flash, LCD display 130 may change to announce the end of cycle, and the vibrator 323 and (optionally) buzzer 322 may be used to alert the user. Device 100 may then power down.

Figure 27:
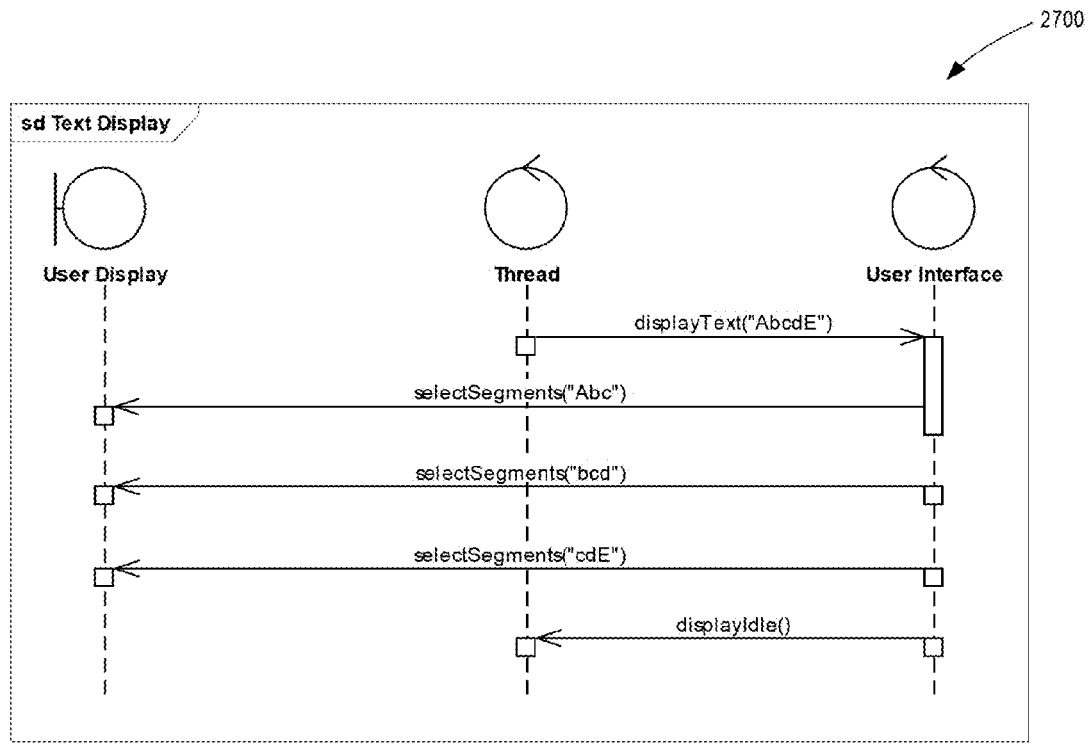
FIG. 27 is a sequence diagram of scrolling text message sequence for the firmware of the device of FIG. 1.

FIG. 27 is a sequence diagram of the scrolling text message sequence 2700 for device firmware 400. This sequence is used to display text messaged on LCD 130.

Figure 28:
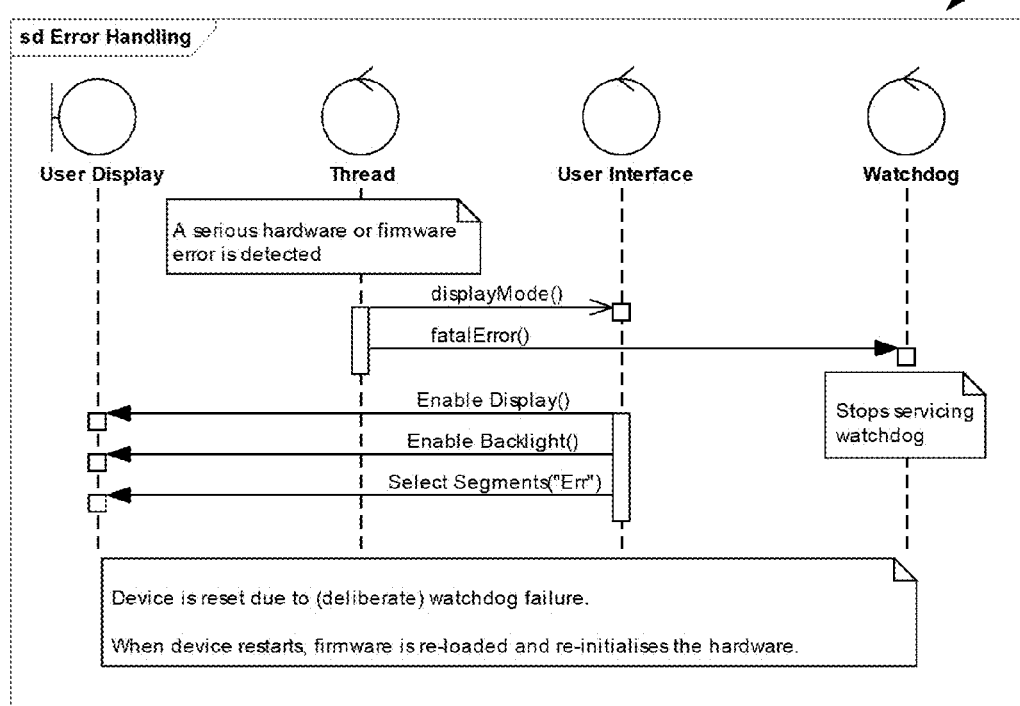
FIG. 28 is a sequence diagram of device fault detection sequence for the firmware of the device of FIG. 1.

FIG. 28 is a sequence diagram of the device fault sequence 2800 for device firmware 400. If device 100 detects a hardware or firmware failure, it may display an error message on LCD 130 and then may appear to switch itself off. To maximise the chances of recovering from the error, a system reset may be performed.

Figure 29:
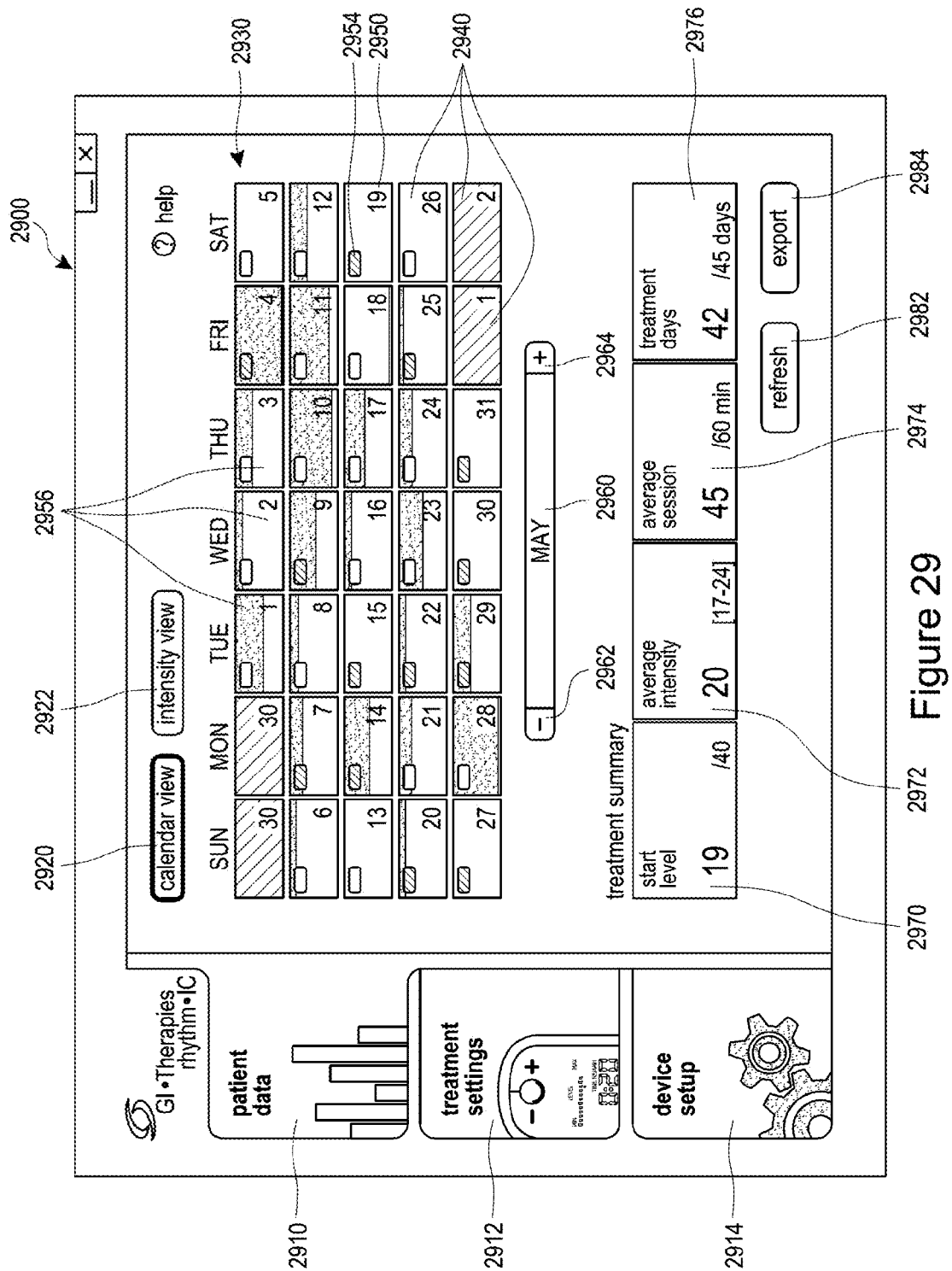
FIG. 29 is an example client-side display of a patient data calendar view page of an application running on the computing device of FIG. 2.

FIG. 29 is an example client-side display 2900 of a page of an application run on computing device 240. The application may allow settings on device 100 to be adjusted and for monitoring of treatment to occur. In some embodiments, the application may be able to assess device 100 settings and data logs when computing device 240 is communicatively connected to device 100 with a USB connection. Display 2900 has patient data tab 2910, treatment settings tab 2912 and device setup tab 2914. FIG. 29 shows patient data tab 2910 being open. Patient data tab 2910 allows the user to view patient data using calendar view or an intensity view, by selecting buttons 2920 or 2922, respectively. FIG. 29 shows calendar view 2920 selected, as indicated by the illumination around this button.

Selecting calendar view 2910 displays a monthly calendar 2930 made up of days 2940, with each day corresponding to a calendar year of a selected month as shown on label 2960. The selected month may be automatically loaded to the current month when the application loads, or may be changed by the user by scrolling through the months using buttons 2962 and 2964. The calendar 2930 may display logging details of a device that has already been used to administer treatment. Each day 2940 displays the date 2950 as well as the recorded amount of treatment that was delivered on that date. Each day further has indicator 2954, which the clinician can use to indicate the occurrence or non-occurrence of an event (i.e. bowl movement), as reported by the patient. Each of the treatment days in the calendar 2930 may include an indicator 2956 of a treatment proportion to indicate the relative duration of the treatment administered on the relevant day, compared to the scheduled, prescribed or intended treatment for that day. For example, if the treatment for a given day was actually only delivered for 15 minutes instead of a specified single 30 minute delivery period for that day, then the treatment proportion indicator 2956 would show that only half (50%) of the treatment was delivered in that day.

Display 2900 may further have panels of information about the treatment history. In the illustrated embodiment, display 2900 has start level panel 2970, average intensity panel 2972, average session panel 2974 and treatment days panel 2976. Start level panel 2970 may show the default intensity level which the stimulation delivered by device 100 ramps up to during treatment. In some embodiments, the maximum treatment level may also be shown. In the illustrated embodiment, the start level is shown to be level 19, out of a maximum of 40 treatment levels. Average intensity panel 2972 may show the average intensity of the stimulation signals delivered over the monitored treatment period. The panel may further show the maximum and minimum intensity levels delivered, as a range. In the illustrated embodiment, the average intensity is shown to be 20, with a range of between 17 and 24. Average session panel 2974 may show the average duration for which stimulation signals were delivered during each day of treatment. It may also show the maximum treatment time available. In the illustrated embodiment, an average session time of 45 minutes is shown, with the maximum treatment time being 60 minutes. Treatment days panel 1976 may show the number of days during the treatment period on which stimulation signals were actually administered, as well as the total number of days in the treatment period. In the illustrated embodiment, the number of treatment days is shown to be 42, out of a treatment period of 45 days.

Display 2900 may have a refresh button 2982 to allow the user to refresh the page, and an export button 2984 to allow the user to export the information to save to file or send to an email address. In some embodiments, display 2900 may further have a print button to allow the user to print the page for their record.

Figure 30:
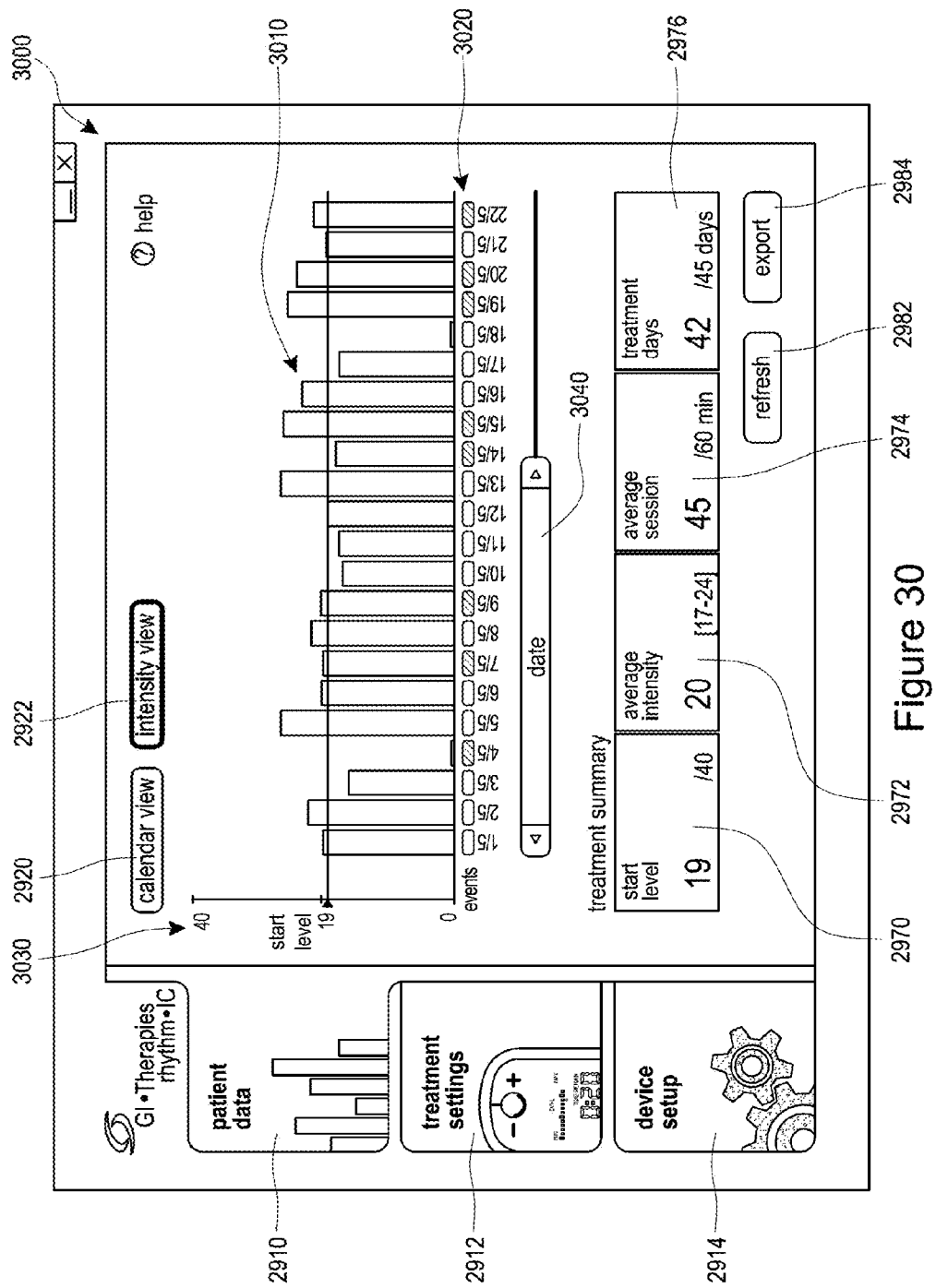
FIG. 30 is an example client-side display of a patient data graph view page of an application running the computing device of FIG. 2.

FIG. 30 is an example client-side display 3000 of a page of an application run on computing device 240, showing patient data tab 2910 selected and graph view option 2920 selected. Display 3000 may be very similar to display 2900, showing the panels 2970, 2972, 2974 and 2976, as well as buttons 2982 and 2984. Graph 3010 is displayed, showing days of treatment 3020 on the x-axis and intensity of treatment 3030 on the y-axis. The user may be able to change the days 3020 visible by moving slide 3040 to shift the portion of the x-axis that is visible.

Figure 31:
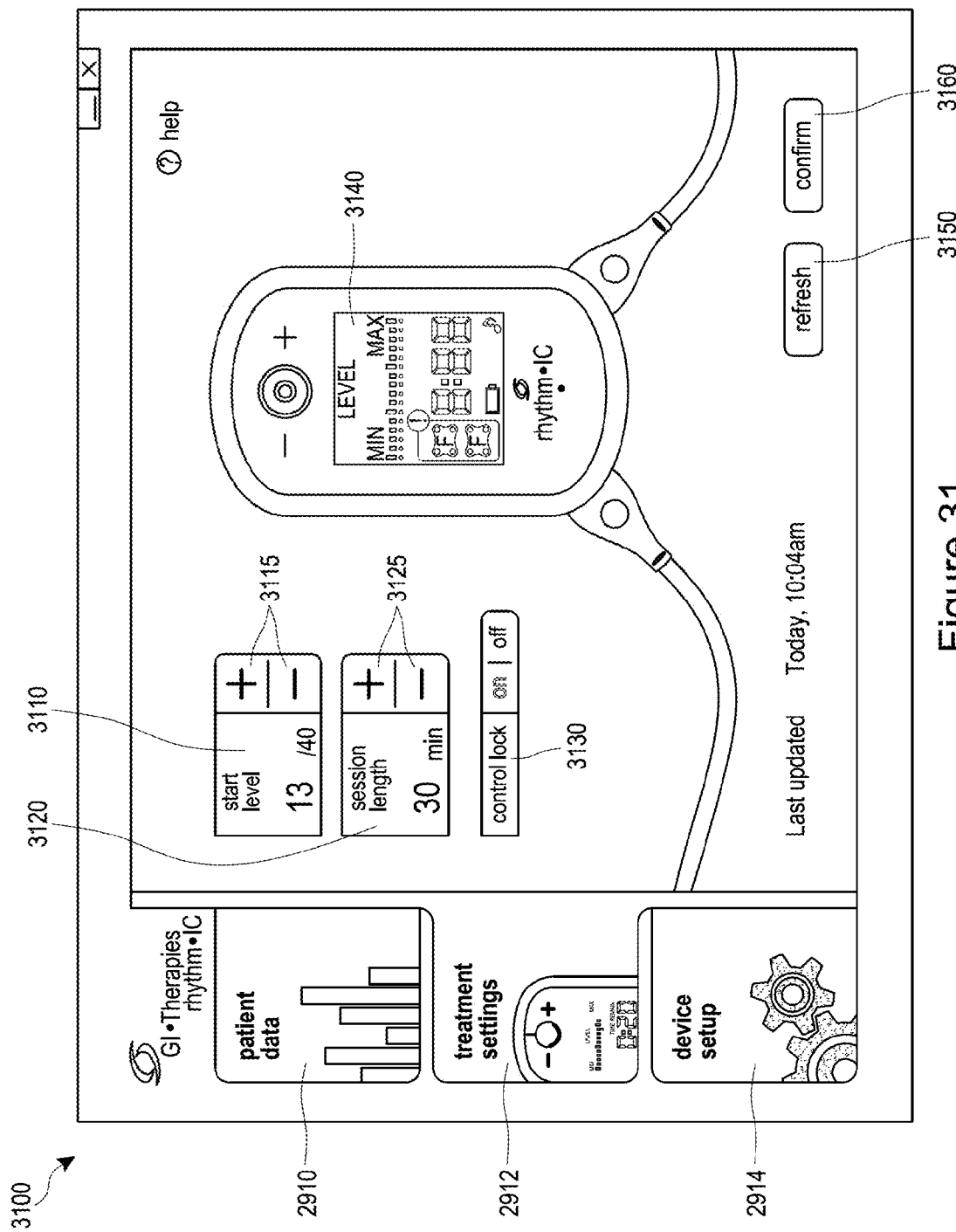
FIG. 31 is an example client-side display of a treatment settings page of an application running on the computing device of FIG. 2.

FIG. 31 is an example client-side display 3100 of a page of an application run on computing device 240, showing treatment settings tab 2912 selected. In some embodiments, display 3100 has start treatment level panel 3110 allowing the user to adjust the start treatment level using buttons 3115. Some embodiments have treatment length panel 3120, allowing the user to adjust the length of treatment using buttons 3125. Display 3100 may further include toggle 3130 to allow the user to put a safety lock or control lock on the device. This causes device 100 to operate in "control lock mode" and limits the maximum treatment level that can be reached, as discussed further above with reference to FIG. 7. Display 3100 may include a graphic representation 3140 of device 100, showing the treatment level and treatment length selected on the representation of LCD 130. Display 3100 may further include refresh button 3150 for refreshing the display, and save button 3160 for saving the setting to apply to device 100.

Figure 32:
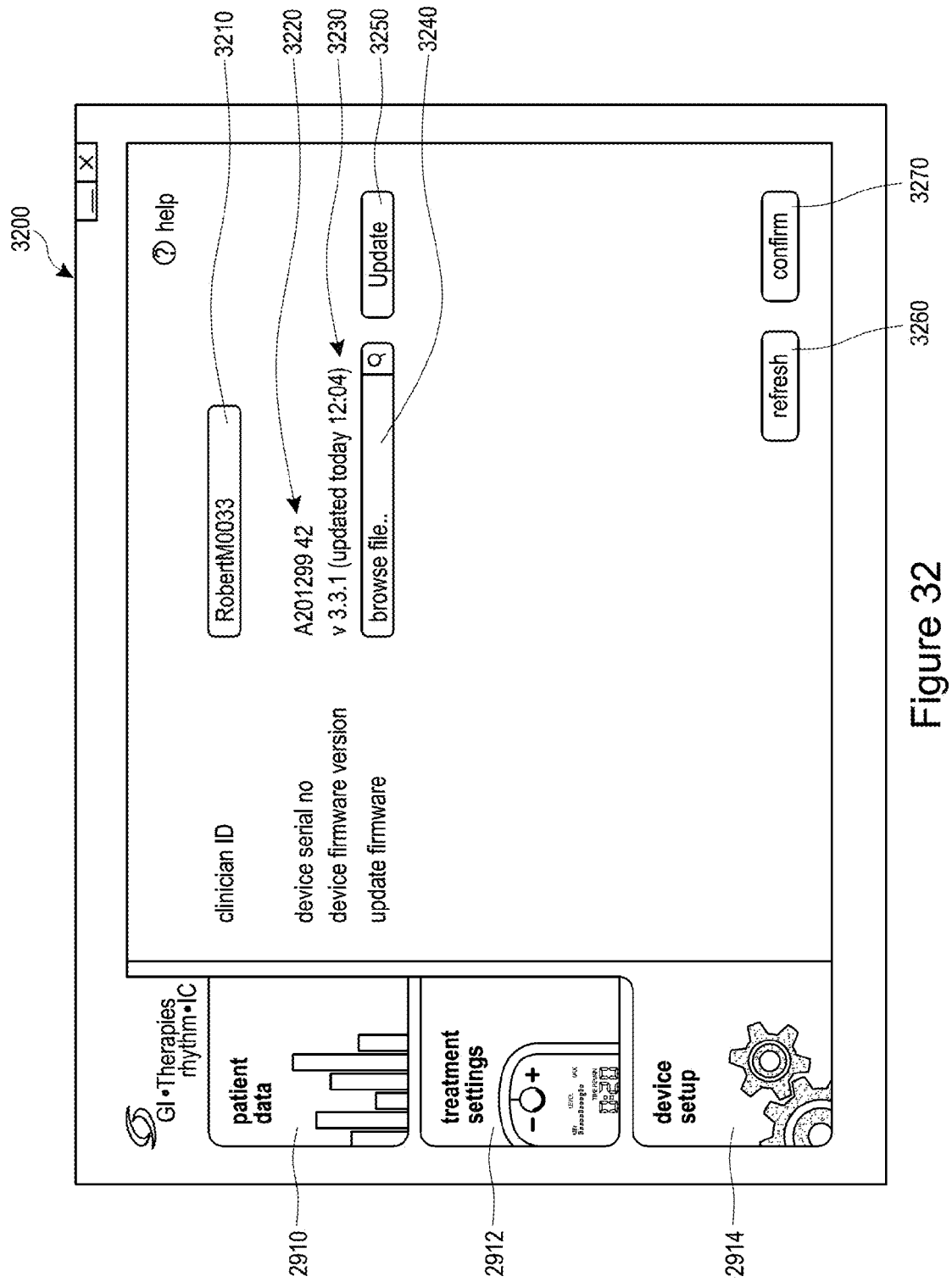
FIG. 32 is an example client-side display of a device setup page of an application run on the computing device of FIG. 2.

FIG. 32 is an example client-side display 3200 of a page of an application run on computing device 240, showing device setup tab 2914 selected. Display 3200 includes text box 3210 where a clinician can enter an identifier, such as their name, which may be used for authorisation and/or reporting purposes. The menu may also show a device serial number 3220 and firmware version 3230 of firmware 400 of device 100 that is plugged into the computing device 240 on which the application is being run. Firmware 400 may be updatable by uploading a new firmware file using file browser 3240. Once the desired file is selected, the firmware may be updated by selecting update button 3250. Display 3200 may also include refresh button 3260 to refresh the display, and save button 3270 to save the desired settings.

In some embodiments, the user of the application may be able to adjust aspects of the stimulation signals such as the duty period, duty cycle, sweep delta minimum, sweep delta maximum, sweep period, switching mode, and output switch over frequency values. This enables a wide variety of stimulation signals and electrode switching patterns to be set up through the application running on computing device 240 as required.

In some embodiments of system 200, electrode connectors 226 and 236 may be arranged in upper and lower banks of electrode connectors. For example, there may be two electrode connectors in the upper bank and two in the lower bank on each electrode connector assembly 220 and 230, such that when the device is worn, the upper electrode connectors sit against the patient's upper abdomen and the lower bank electrode connectors sit on the patient's lower abdomen. In this case, device 100 may be configured to enable the stimulation signals on the lower bank of electrodes for 15 minutes, then on the upper bank for 15 minutes, followed by 15 minutes on the lower bank and finishing with 15 minutes on the higher bank. These configurations can be changed to any other combination of stimulation patterns through firmware 400. For example, in some embodiments, device 100 may activate the upper bank of electrodes first for a first set period, and subsequently activate the lower bank for a second set period, which may be the same or different from the first set period. The stimulation periods can be adjusted to be longer or shorter in duration as required. In some embodiments, electrodes may alternatively be configured in left and right banks, such that device 100 may be configured to activate only the right bank of electrodes, only the left bank, or to switch between right and left banks.

In some alternative embodiments of system 200, there may only be a single bank of electrodes, and the device may be worn so that the electrodes are placed on either the upper or the lower abdomen of the patient.

Figures 33A, 33B:
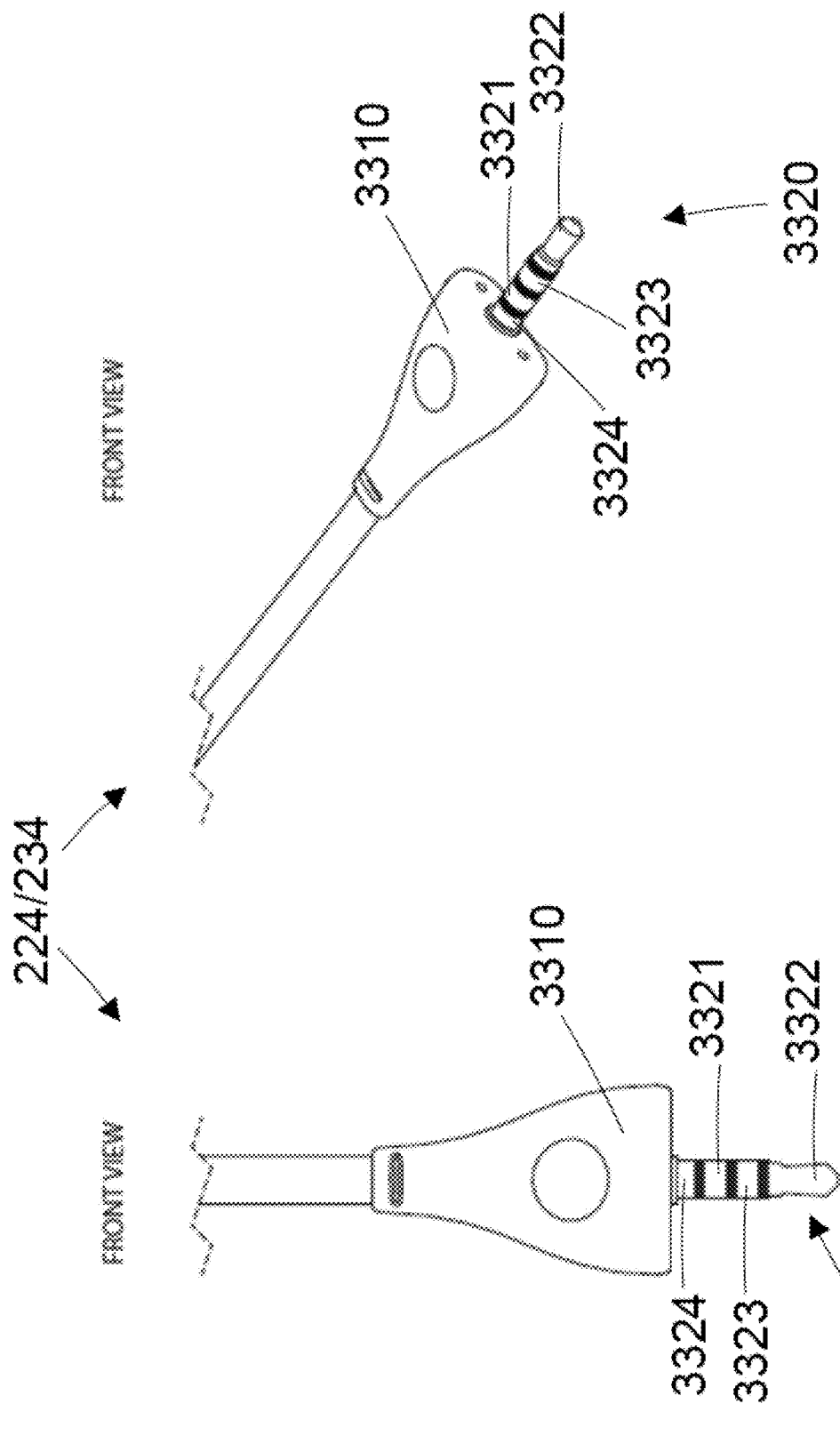
FIGS. 33a and 33b show top and perspective views of connectors that may plug into some embodiments of the device of FIG. 1.

FIG. 33a shows a top view of a cable connector 224 or 234. Although system 200 has a back cable connector 224 and front cable connector 234, only one cable connector is illustrated for simplicity. Back and front cable connectors 224 and 234 may each have a shaped gripping portion 3310 and connector pin 3320. Shaped gripping portion 3310 may be moulded of plastic or otherwise formed to a size and shape for easy manual handling. The shape may be designed to be fitted to the exterior of the external housing of device 100, such that when connectors 224 and 234 are inserted into connector inputs 160 and 165, gripping portion 3310 limits the degree of movement of connector 224 or 234 with respect to device 100 about the insertion axis of connector 224 or 234. Device 100 may have a recessed area around each connector input 160 and 165 to receive and couple with a part of the exterior of gripping portion 3310 that is adjacent the connector pin 3320. In some embodiments, back and front cable connectors 224 and 234 may be identical in shape, allowing either connector to be plugged into either connector input 160 or 165. In some embodiments, back and front cable connectors 224 and 234 may be mirror images of each other, or otherwise different in shape, with each recess on the housing of device 100 coupling only to one of connectors 224 or 234, to prevent each connector 224 or 234 from being plugged into the wrong connector input 160 or 165.

Connector pin 3320 may be an electrically conductive pin to be received and to electrically couple with connector input 160 or 165. In some embodiments, connector pin 3320 may have 4 separate electrically isolated signal channels. In some such embodiments, connector pin 3320 may be a 4-pole pin. In some embodiments, connector pin 3320 may have 2, 3, 5, 6, or another number of electrically isolated signal channels. Where connector pin 3320 is a 4-pole pin, it may have isolated conductive sections 3321, 3322, 3323 and 3324. These may be ordered along pin 3320 in a way designed to reduce the risk of danger through the accidental short circuiting of conductive sections. For example, the conductive sections may be arranged such that any two adjacent conductive sections will not be active simultaneously. This safety feature is further described in reference to FIG. 34.

Figure 34:
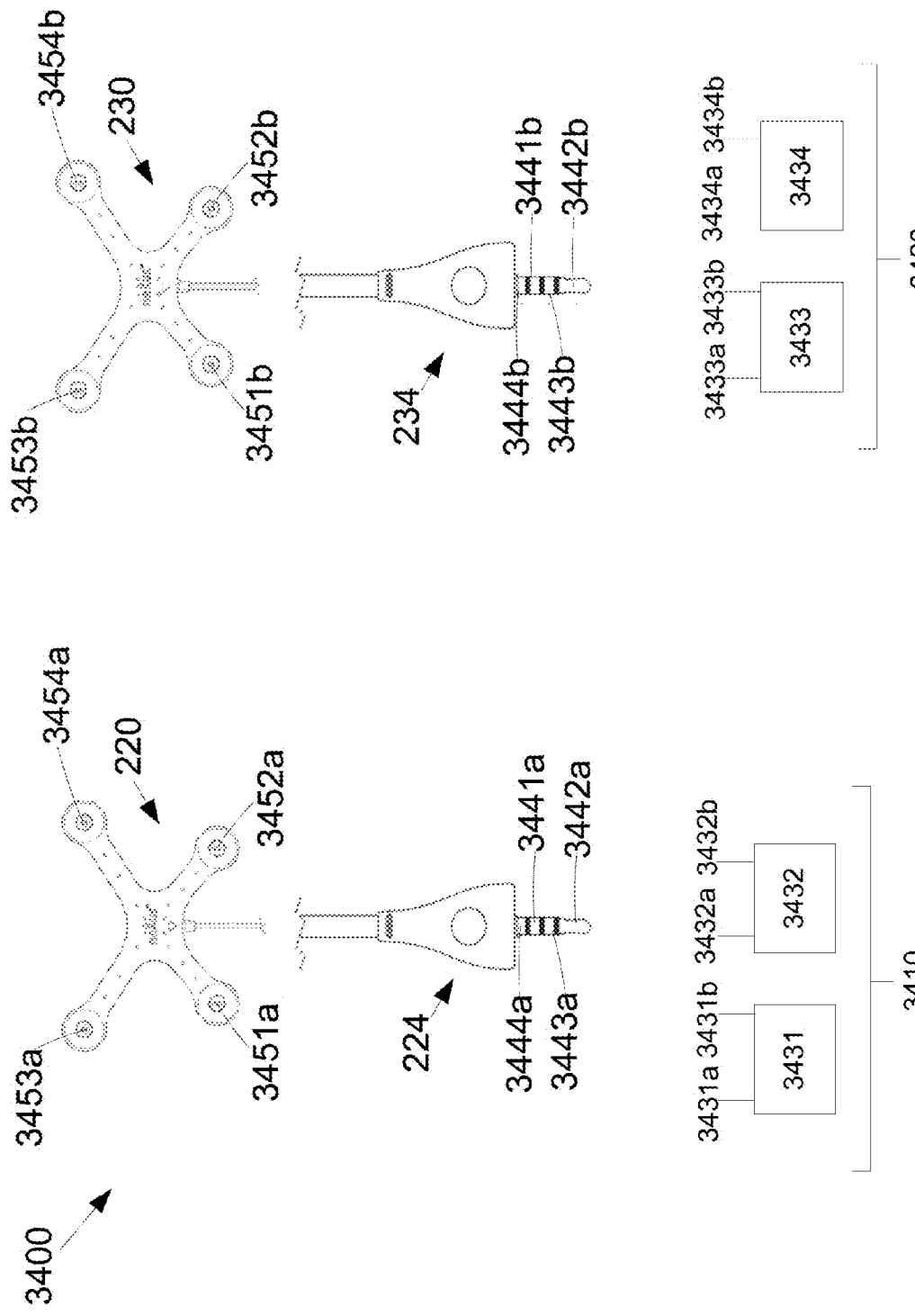
FIG. 34 is a diagram illustrating signal path channels of the device of FIG. 1.

FIG. 34 is a diagram of the signal path channels 3400 of the device of FIG. 1. As described with reference to FIG. 2 above, output stage 380 of device 100 drives output transformers that supply current to electrode connectors 226 and 236. In some embodiments, the transformers may include four transformers 3431, 3432, 3433 and 3434, one for each back/front electrode pair. These may be divided into lower transformer bank 3410, having transformers 3431 and 3432, and upper transformer bank 3420 having transformers 3433 and 3434. Each transformer output may be split into an "a" and "b" line. The output signals from each transformer may be passed through connectors 224 and 234 and onto electrode connector assemblies 220 and 230. In some embodiments, all "a" lines are passed to front connector 224, while all "b" lines are passed to back connector 234. Where connectors 224 and 234 are 4-pole pin connectors, the lines coming from transformers 3431, 3432, 3433 and 3434 may be arranged such that lines coming from lower transformer bank 3410 are not adjacent each other on the conductive pin portion.

In some embodiments, connector 224 may have conductive pin sections 3441a, 3442a, 3443a and 3444a, and connector 234 may have conductive pin sections 3441b, 3442b, 3443b and 3444b. These may be arranged as shown in FIG. 34, such that conductive pin sections 3441 and 3442 are not adjacent, and conductive pin sections 3443 and 3444 are not adjacent. Conductive pin section 3441a, 3442a, 3443a and 3444a may be electrically coupled to lines 3431a, 3432a, 3433a and 3434a, respectively. Conductive pin section 3441b, 3442b, 3443b and 3444b may be electrically coupled to lines 3431b, 3432b, 3433b and 3434b, respectively. In some embodiments, lower transformer bank 3410 and upper transformer bank 3420 are never active simultaneously. This results in a situation whereby as connectors 224 and 234 are inserted into connection inputs 160 and 165, there is a reduced chance of a short circuit across two active signal lines.

Connector 224 is electrically coupled with front electrode connector assembly 220, having electrode connector portions 3451a, 3452a, 3453a and 3454a. In some embodiments, conductive pin section 3441a, 3442a, 3443a and 3444a may be electrically coupled to electrode connector portions 3451a, 3452a, 3453a and 3454a, respectively. Connector 234 is electrically coupled with back electrode connector assembly 230, having electrode connector portions 3451b, 3452b, 3453b and 3454b. In some embodiments, conductive pin section 3441b, 3442b, 3443b and 3444b may be electrically coupled to electrode connector portions 3451b, 3452b, 3453b and 3454b, respectively.

For each electrode connector assembly 220 or 230, signals coming from lower transformer bank 3410 appear on electrodes placed in the lower section of electrode connector assembly 220 or 230, while signals coming from upper transformer bank 3420 appear on electrodes placed in the upper section of electrode connector assembly 220 or 230. Therefore, in some embodiments, when worn on the human body front and back electrode connector assemblies 220 and 230 provide stimulation to the upper section of the patient's abdomen or the lower section of the patient's abdomen at any given time, but cannot stimulate both simultaneously. As described above with reference to FIG. 32, device 100 may be configured to provide stimulation to both upper and lower electrode sets by switching the active transformer bank between activating lower bank 3410 and upper bank 3420. This switching may be done periodically (e.g. every 10 to 20 minutes), or after a programmed interval (e.g. after about 10, 15, 20, 25, 30, 35, 40, 45 or 50 minutes).

In some embodiments, microcontroller 355 of device 100 may be configured to control the generation and delivery of interferential current stimulation signals to different pairs of electrodes that include any electrode to which back electrode connector assembly 220 is connected in combination with any electrode to which front electrode connector assembly 230 is connected. For example, microcontroller 355 may be configured to control the generation and delivery of stimulation signals between an electrode electrically connected to the top left of back electrode connector assembly 220 and an electrode electrically connected to the bottom right of front electrode connector assembly 230. In another example, device 100 may be configured to deliver stimulation signals to an electrode electrically connected to the top left of back electrode connector assembly 220 and an electrode electrically connected to the bottom left of front electrode connector assembly 230 simultaneously. Alternatively, any other pair of electrodes, wherein one electrode is selected from each of the electrodes electrically connected to back electrode connector assembly 220 and front electrode connector assembly 230, may be controlled by microcontroller 355 to deliver stimulation signals based on stored configuration parameters in device 100. This may be done by providing stimulation signals to a pair of conductive pin sections, wherein one conductive pin section is selected from connector 224 and one conductive pin section is selected from connector 234. In use, two such selected electrode pairs may receive interferential current stimulation signals from the stimulation device 100 and apply these signals transcutaneously across parts of the lower abdomen/pelvis and lumbar/sacral region.

FIGS. 35a, 35b and 35c show top, perspective and end views of an alternative cable connector 3524 or 3534 for use in system 200. Although system 200 has a back cable connector 224 and front cable connector 234, only one cable connector 3524/3534 is illustrated in FIGS. 35a, 35b and 35c for simplicity. Back and front cable connectors 3524 and 3534 may each have a shaped gripping portion 3510 and connector plug portion 3520. Connector plug portion 3520 may be an electrically conductive plug portion to be received in and to electrically couple with a recess 3620 of socket 3610 (see FIG. 36a) within connector inputs 160 or 165. Socket 3610 may be configured to cooperate with the connector plug portion 3520 to electrically couple the electrode connector assembly 220, 230 to the stimulation generation device 100.

Shaped gripping portion 3510 may have a curved shoulder portion 3515 shaped to be received in a recessed portion 3615 of socket 3610 of device 100. In some embodiments, the gripping portion 3510 comprises a substantially flat base portion 3530 and a rounded or curved surface portion 3540 and is configured to cooperate with a correspondingly shaped recessed portion 3615 of socket 3610. Socket 3610 may be recessed into a corner of stimulation device 100.

Connector plug portion 3520 may extend out of the gripping portion 3510 and contain a series of hollow pin port plugs 3525. Each pin port plug may form part of a separate electrically isolated signal channel. In some embodiments, device 100 may have 2, 3, 4, 5, 6, or another number of electrically isolated signal channels, each corresponding to a pin port 3525.

In some embodiments, the connector plug portion 3520 may be a four pin port plug and each pin port 3525 may be associated with and arranged to electrically couple to a respective pin 3625 positioned within recess 3620 of socket 3610 of the stimulation generation device 100 to thereby allow transcutaneous electrical stimulation to be delivered to the electrode connector assembly 220, 230.

Pin ports 3525 may be arranged linearly along a latitudinal axis of the connector plug 3520. Alternatively, pin ports 3525 may be aligned along a longitudinal axis of the connector plug 3520. In other embodiments, pin ports 3525 may be arranged in any suitable configuration, for example, in a square or circular formation.

In some embodiments, the connector plug portion 3520 may comprise a front face 3550 and the pin ports 3525 may extend through the front face 3550. Connector plug portion 3520 may include a notch 3560 for aligning connector plug portion 3520 with a corresponding projection 3660 in recess 3620 of socket 3610. In this way, the connector plug portion 3520 may be received by the socket 3610 only when it is orientated correctly.

A successful treatment of a patient by administration of transcutaneous electrical stimulation treatment delivered using the device 100 of some of the described embodiments is one that may include at least one or more of the following features: (a) number of defecations have increased per week; (b) the number of soiling incidents decreased; (c) reduced use of laxatives; (d) changes in the consistency of the stool from hard to increased softness; and (e) increase in sensory awareness of urge to defecate. Studies involving some described embodiments are described by the following non-limiting prophetic example.

EXAMPLE 1

The Use of a System for Delivering Transcutaneous Electrical Stimulation in the Treatment of Individuals with a Faecal Waste Elimination Dysfunction Condition.

Patient Group: Includes individuals suffering from faecal waste elimination dysfunction of the gastrointestinal tract that have failed to respond significantly to medical treatments such as dietary modifications, oral and rectal laxatives. Given the diversity of human body shapes, individuals participating will be of a variety of body shapes and sizes associated with weight, age, ethnicity and gender.

Stimulation Regime a) The Setting of the Device by a Clinician or Trained Health Care Professional The device 100 forms part of system 200, which is designed to be set up for each patient by a health care professional or someone trained in its use. The device 100 has variable settings within the software that allow the clinician to select the length of treatment time (30 or 60 minutes standard settings). On the device 100, there are buttons to turn the device on/off, to change the current (mAs, level) delivered, and to choose between audible or non-audible alarms.

The clinician, or treating physician will determine the initial stimulation level for the patient; both children, and/or adults with faecal waste elimination dysfunction of the gastrointestinal tract. The stimulation device 100 can deliver current from 0 to 30 mAmps over a 1KΩ load and the level for initial use will be chosen with the stimulation system attached to the individual and turned on. The level will be turned up stepwise (incrementally) by the clinician and/or individual until the highest comfortable level is reached. The patient will feel tingling under the electrodes and can indicate when the tingling begins to become uncomfortable. The device has a function that allows the clinician to set this level, which is the individual's "start-level".

b) The Use of the Device by the Individual Patient for the Treatment of Faecal Waste Elimination Dysfunction On subsequent uses, when the device 100 is turned on and the electrodes are connected, the treatment level will rise from 0 to the "start level" at a comfortable rate. The patient can then use the device 100 on this level or increase or decrease the stimulation intensity by pressing buttons 180, 185.

The device 100 also has a control lock. With this activated, the patient can only turn the device up or down 3 levels, which may be 3 mA levels in some embodiments, depending on the patient impedance. This is for use with patients who would fiddle with the device and could turn it up too high or turn it off (young children, hyperactive children, adults with attention disorders etc).

Generation and transmission of stimulation signals will be controlled and monitored by the device 100. The stimulation parameters include a variety of times of stimulation: 30 or 60 minutes per day for at least three or at least four times a week (preferably every day) or greater for a minimum of 2 months. During the stimulation period, the participants will be encouraged to continue to perform "normal activities" of daily life which may include a range of movements from standing to sitting or gentle play activities. Patients can increase the current level at each sitting to the maximum tolerated (unless the control lock has been activated).

If stimulation is interrupted during the treatment session, the device 100 will recommence at the interrupted time and at the last level setting when reattached or turned back on and deliver the stimulation for the remaining part of the set stimulation period.

The device 100 connects via two cable leads 222, 232 to eight electrode pads 214, 218. The wires in cables 222, 232 leading to the electrodes of the accompanying delivery device 100 are separate and fixed within a silicon shell to ensure the arrangement of leads to deliver current to standard positions (upper front left, upper front right, lower front left, lower front right, upper back left, upper back right, lower back left and lower back right). The device 100 has sensor circuits to determine if the stimulation currents are flowing. If the current is not flowing, the device indicates a 'pad fault' and displays the site of the fault (8 pads, upper front left, upper front right, lower front left, lower front right, upper back left, upper back right, lower back left and lower back right). If a pad fault is detected, the device will reduce the current to a low level and emit a notification (audible and/or vibration) until the connection is established. Once all pads are connected to the leads and the connection to the skin is determined to be sufficient, the device 100 will ramp the current back up to the 'start level'.

The device 100 will automatically turn off after the set stimulation period has elapsed. The device 100 will give a notification (audible and/or vibration) just before it turns off. The device 100 will display a symbol to remind the patient to recharge the device 100. The device 100 has a rechargeable battery and this must be recharged between uses.

The device 100 records the amount of time it was run for, the date and the highest level used. The device records these measures for a predetermined period of time, which may be in the order of 90 days, 180 days, or 3 years in some embodiments. The clinician can download this data via a USB or wireless link to the computer. The data is displayed in calendar and graph form with a summary of the number of days used (out of days elapsed), to give the clinician data to assess compliance with the treatment schedule and the treatment levels used.

c) Treatment Assessment

As the purpose of this device 100 and system 200 is to treat individuals with faecal waste elimination dysfunction, to determine benefits of this device the patient is also provided with a continence diary to record: defecations (time and amount), whether the defecation was in response to an urge to defecate, occurred while sitting on the toilet at preset times, the consistency of the stool (hardness and softness) and soiling incidents, the amount of medication (laxatives) and number of incidents of soiling. The daily dairy can be filled in for each day during the period of transcutaneous electrical stimulation. The treating clinician/physician may during the treatment period or after the treatment period review the both the continence diary and the stimulation records which will include the actual length of time of stimulation and the number of times the stimulation was used and the days used.

A successful treatment is one that includes at least one or more of the following features (a) number of defecations have increased per week, (b) the number of soiling incidents decreased, (c) reduced use of laxatives, (d) changes in the consistency of the stool from hard to increased softness and (e) increase in sensory awareness of urge to defecate.

The level of stimulation as pre-set by the clinician at the initial consultation and a non-changeable parameter by the patient will also be noted. On review of the outcome, the stimulation program and the recorded results, the treating clinician may choose to alter parameters for further treatment.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A device to treat a waste evacuation dysfunction, the device comprising:
   circuitry configured to generate transcutaneous electrical stimulation signals;
   at least one first signal output component configured to electrically connect the circuitry to a first plurality of electrodes; and at least one second signal output component configured to electrically connect the circuitry to a second plurality of electrodes; and wherein the device is configured to:
deliver the generated transcutaneous electrical stimulation signals for a first period of time to a first bank of electrodes to create interferential current in a first region located between a front of a torso and a back of the torso of a user, the first bank of electrodes comprising four or more electrodes selected from the first and second pluralities of electrodes, and deliver the generated transcutaneous electrical stimulation signals for a second period of time to a second bank of electrodes to create interferential current in a second region located between the front and back of the torso that is different from the first region, the second bank of electrodes comprising four or more electrodes selected from the first and second pluralities of electrodes, wherein the first period of time and the second period of time begin at different points in time.

2. The device of claim 1, wherein the first bank of electrodes comprises two electrodes from the first plurality of electrodes and two electrodes from the second plurality of electrodes.

3. The device of claim 1, wherein the first bank of electrodes is configured to be positioned offset relative to the second bank of electrodes.

4. The device of claim 1, wherein the first period of time does not overlap with the second period of time.

5. The device of claim 1, wherein the first period of time at least partially overlaps the second period of time.

6. The device of claim 1, wherein the front of the torso of the user comprises a lower abdomen and a pelvic area of the user, and the back of the torso of the user comprises a lumbar and sacral area of the user.

7. The device of claim 1, wherein the device is configured to allow adjustment of an electrical stimulation parameter of the device to restrict the generated transcutaneous electrical stimulation signals to a current intensity that is less than a maximum possible current intensity of the device.

8. The device of claim 1, wherein the device is configured to allow adjustment of an electrical stimulation parameter of the device to restrict the generated transcutaneous electrical stimulation signals to a treatment session duration that is less than a maximum possible treatment session duration of the device.

9. The device of claim 1, wherein the device is configured to allow adjustment of an electrical stimulation parameter of the device to restrict the generated transcutaneous electrical stimulation signals to frequency of use of the device that is less than a maximum possible frequency of use of the device.

10. The device of claim 1, wherein the transcutaneous electrical stimulation signals comprise a constant frequency.

11. The device of claim 1, wherein the transcutaneous electrical stimulation signals comprise a sweeping frequency.

12. A device to treat a waste evacuation dysfunction, the device comprising:
circuitry configured to generate transcutaneous electrical stimulation signals to create interferential current between a front of a torso of a user and a back of the torso of the user;
at least one first signal output component for electrically connecting the circuitry to a first plurality of electrodes; and at least one second signal output component for electrically connecting the circuitry to a second plurality of electrodes; and wherein the device is configured to allow adjustment of one or more electrical stimulation parameters of the device to restrict the generated transcutaneous electrical stimulation signals to one or more of a current intensity, treatment session duration, and frequency of use of the device that are less than, respectively, a maximum possible current intensity, a maximum possible treatment session duration and a maximum possible frequency of use of the device.

13. The device of claim 12, wherein the device comprises communication circuitry configured to receive input from a remote computing device to adjust the one or more electrical stimulation parameters of the device.

14. The device of claim 12, wherein the device comprises an interface configured to receive input from a user to adjust the one or more electrical stimulation parameters of the device.

15. The device of claim 12, wherein the device is further configured to:
deliver the generated transcutaneous electrical stimulation signals to a first bank of electrodes to create the interferential current in a first region located between the front and back of the torso, the first bank of electrodes comprising four or more electrodes selected from the first and second pluralities of electrodes, and deliver the generated transcutaneous electrical stimulation signals to a second bank of electrodes to create the interferential current in a second region located between the front and back of the torso that is different from the first region, the second bank of electrodes comprising four or more electrodes selected from the first and second pluralities of electrodes.

16. The device of claim 15, wherein the device is further configured to:
deliver the generated transcutaneous electrical stimulation signals to the first bank of electrodes for a first period of time, and deliver the generated transcutaneous electrical stimulation signals to the second bank of electrodes for a second period of time, wherein the first period of time and the second period of time begin at different points in time.

17. A device to treat a waste evacuation dysfunction, the device comprising:
circuitry configured to generate transcutaneous electrical stimulation signals; and one or more signal output components configured to be electrically connected with a plurality of electrodes to deliver the transcutaneous electrical stimulation signals from the circuitry to a user, wherein the device is configured to:
deliver the generated transcutaneous electrical stimulation signals for a first period of time to create interferential current in a first region located between a front of a torso of the user and a back of the torso of the user, deliver the generated transcutaneous electrical stimulation signals for a second period of time to create interferential current in a second region located between the front and back of the torso that is different from the first region, and allow adjustment of one or more electrical stimulation parameters of the device to restrict the generated transcutaneous electrical stimulation signals to one or more of a current intensity, treatment session duration, and frequency of use of the device.

18. The device of claim 17, wherein the first period of time and the second period of time begin at different points in time.

19. The device of claim 17, wherein the restricted current intensity, treatment session duration, and frequency of use of the device are less than, respectively, a maximum possible current intensity, a maximum possible treatment session duration and a maximum possible frequency of use of the device.

20. The device of claim 17, wherein the device is further configured to:
   monitor output feedback signals for pad fault detection; and
   adjust the current intensity to a minimum current intensity in response to a pad fault detection.

* * * * *